(12) United States Patent
Hadden et al.

(10) Patent No.: US 9,492,519 B2
(45) Date of Patent: Nov. 15, 2016

(54) VACCINE IMMUNOTHERAPY

(71) Applicant: IRX Therapeutics, Inc., New York, NY (US)

(72) Inventors: John W. Hadden, Cold Spring Harbor, NY (US); Kathy L. Signorelli-Petrat, Springfield, VA (US); James E. Egan, Stony Brook, NY (US)

(73) Assignee: IRX Therapeutics, Inc., New York, NY (US)

( * ) Notice: Subject to any disclaimer, the term of this patent is extended or adjusted under 35 U.S.C. 154(b) by 612 days.

(21) Appl. No.: 13/940,635

(22) Filed: Jul. 12, 2013

(65) Prior Publication Data
US 2014/0030217 A1 Jan. 30, 2014

Related U.S. Application Data

(63) Continuation of application No. 12/374,732, filed as application No. PCT/US2007/074156 on Jul. 24, 2007, which is a continuation of application No. 11/492,418, filed on Jul. 25, 2006, now abandoned, (Continued)

(51) Int. Cl.
*A61K 38/00* (2006.01)
*A61K 39/00* (2006.01)
(Continued)

(52) U.S. Cl.
CPC ......... *A61K 39/0011* (2013.01); *A61K 38/191* (2013.01); *A61K 38/204* (2013.01);
(Continued)

(58) Field of Classification Search
CPC .............................. A61K 38/20; A61K 38/21
See application file for complete search history.

(56) References Cited

U.S. PATENT DOCUMENTS

| 4,079,127 A | 3/1978 | Goldstein et al. |
| 4,116,951 A | 9/1978 | Wang |

(Continued)

FOREIGN PATENT DOCUMENTS

| CN | 1106297 A | 8/1995 |
| EP | 0 041 189 A1 | 12/1981 |

(Continued)

OTHER PUBLICATIONS

Hadden (Int J Immunopharmacol. Feb. 1999;21(2):79-101).*

(Continued)

*Primary Examiner* — Cherie M Stanfield
(74) *Attorney, Agent, or Firm* — Wolf, Greenfield & Sacks, P.C.

(57) ABSTRACT

The present invention provides compositions and methods of immunotherapy to treat cancer or other antigen-producing diseases or lesions. According to one embodiment of the invention, a composition is provided for eliciting an immune response to at (east one antigen in a patient having an antigen-producing disease or lesion, the composition comprising an effective amount of a cytokine mixture, preferably comprising IL-1, IL-2, IL-6, IL-8, IFN γ (gamma) and TNF-α (alpha). The cytokine mixture acts as an adjuvant with the antigen associated with the antigen-producing disease or lesion to enhance the immune response of the patient to the antigen. Methods are therefore also provided for eliciting an immune response to at least one antigen in a patient having an antigen-producing disease or lesion utilizing the cytokine mixture of the invention. The compositions and methods are useful in the treatment of antigen-producing diseases such as cancer, infectious diseases or persistent lesions.

16 Claims, 26 Drawing Sheets

Related U.S. Application Data which is a continuation-in-part of application No. 10/637,869, filed on Aug. 8, 2003, now Pat. No. 7,182,942, which is a continuation-in-part of application No. 10/015,123, filed on Oct. 26, 2001, now Pat. No. 6,977,072.

(60) Provisional application No. 60/243,912, filed on Oct. 27, 2000.

(51) Int. Cl.
    A61K 38/21    (2006.01)
    A61K 38/19    (2006.01)
    A61K 38/20    (2006.01)

(52) U.S. Cl.
    CPC ....... *A61K38/2006* (2013.01); *A61K 38/2013* (2013.01); *A61K 38/2053* (2013.01); *A61K 38/217* (2013.01)

(56) References Cited

U.S. PATENT DOCUMENTS

| | | |
|---|---|---|
| 4,148,788 A | 4/1979 | Wang |
| 4,293,455 A | 10/1981 | Merrifield et al. |
| 4,353,821 A | 10/1982 | Birr et al. |
| 4,390,623 A | 6/1983 | Frabricius et al. |
| 4,406,830 A | 9/1983 | Fabricius et al. |
| 4,448,879 A | 5/1984 | Fabricius et al. |
| 4,464,355 A | 8/1984 | Fabricius et al. |
| 4,466,918 A | 8/1984 | Birr et al. |
| 4,470,926 A | 9/1984 | Birr et al. |
| 4,504,415 A | 3/1985 | Felix et al. |
| 4,612,365 A | 9/1986 | Birr et al. |
| 4,614,731 A | 9/1986 | Horecker |
| 4,659,694 A | 4/1987 | Horecker |
| 4,716,148 A | 12/1987 | Horecker |
| 4,910,296 A | 3/1990 | Birr et al. |
| 5,098,702 A | 3/1992 | Zimmerman et al. |
| 5,100,664 A | 3/1992 | Doyle et al. |
| 5,503,828 A | 4/1996 | Testa et al. |
| 5,503,841 A | 4/1996 | Doyle et al. |
| 5,632,983 A * | 5/1997 | Hadden .................. A61K 38/19 424/85.1 |
| 5,643,565 A | 7/1997 | Doyle et al. |
| 5,679,356 A | 10/1997 | Bonnem et al. |
| 5,698,194 A | 12/1997 | Hadden |
| 5,747,024 A | 5/1998 | Grabstein et al. |
| 5,788,963 A | 8/1998 | Murphy et al. |
| 5,800,810 A | 9/1998 | Doyle et al. |
| 5,849,307 A | 12/1998 | Metz et al. |
| 5,849,589 A | 12/1998 | Tedder et al. |
| 5,866,115 A | 2/1999 | Kanz et al. |
| 6,017,527 A | 1/2000 | Maraskovsky et al. |
| 6,060,068 A | 5/2000 | Doyle et al. |
| 6,274,378 B1 | 8/2001 | Steinman et al. |
| 6,350,589 B1 | 2/2002 | Morris et al. |
| 6,482,389 B1 | 11/2002 | Hadden |
| 6,759,239 B2 | 7/2004 | Suciu-Foca et al. |
| 6,896,879 B2 | 5/2005 | Talor |
| 6,977,072 B2 | 12/2005 | Hadden |
| 7,153,499 B2 | 12/2006 | Hadden |
| 7,182,942 B2 | 2/2007 | Hadden |
| 7,374,751 B1 | 5/2008 | Hancock |
| 7,731,945 B2 | 6/2010 | Hadden |
| 7,993,660 B2 | 8/2011 | Hadden et al. |
| 8,470,562 B2 | 6/2013 | Fennington, Jr. et al. |
| 8,591,956 B2 | 11/2013 | Hadden et al. |
| 8,784,796 B2 | 7/2014 | Hadden |
| 2001/0053361 A1 | 12/2001 | Thompson et al. |
| 2002/0034494 A1 | 3/2002 | Vicari et al. |
| 2002/0058019 A1 | 5/2002 | Berenson et al. |
| 2002/0146397 A1 | 10/2002 | Hadden |
| 2002/0159953 A1 | 10/2002 | Hadden |
| 2003/0007955 A1 | 1/2003 | Rees et al. |
| 2003/0206885 A1 | 11/2003 | Hadden |
| 2004/0001829 A1 | 1/2004 | June et al. |
| 2004/0071658 A1 | 4/2004 | Hadden et al. |
| 2004/0136952 A1 | 7/2004 | Bhaskaran et al. |
| 2005/0008614 A1 | 1/2005 | Nieland et al. |
| 2005/0124645 A1 | 6/2005 | Finkel |
| 2005/0152874 A1 | 7/2005 | Hadden |
| 2006/0120996 A1 | 6/2006 | Hadden |
| 2006/0140983 A1 | 6/2006 | Palucka et al. |
| 2006/0194242 A1 | 8/2006 | Hadden |
| 2007/0025958 A1 | 2/2007 | Hadden |
| 2007/0031372 A1 | 2/2007 | Hadden |
| 2007/0041956 A1 | 2/2007 | Hadden |
| 2007/0065415 A1 | 3/2007 | Kleinsek et al. |
| 2007/0128174 A1 | 6/2007 | Kleinsek et al. |
| 2007/0154399 A1 | 7/2007 | Hadden |
| 2007/0196335 A1 | 8/2007 | Pardoll et al. |
| 2007/0259330 A1 | 11/2007 | Goddard et al. |
| 2008/0138365 A1 | 6/2008 | Berinstein et al. |
| 2008/0220000 A1 | 9/2008 | Moore et al. |
| 2009/0041797 A1 | 2/2009 | Davis et al. |
| 2009/0180982 A1 | 7/2009 | Hadden, Sr. |
| 2009/0181078 A1 | 7/2009 | Reed et al. |
| 2009/0258395 A1 | 10/2009 | Fennington, Jr. et al. |
| 2010/0047182 A1 | 2/2010 | Hadden |
| 2010/0047205 A1 | 2/2010 | Hadden et al. |
| 2010/0310469 A1 | 12/2010 | Hadden |
| 2011/0044941 A1 | 2/2011 | Hadden |
| 2011/0076249 A1 | 3/2011 | Hadden et al. |
| 2011/0081313 A1 | 4/2011 | Hadden |
| 2011/0110884 A1 | 5/2011 | Hadden et al. |
| 2012/0064035 A1 | 3/2012 | Hadden et al. |
| 2012/0141512 A1 | 6/2012 | Hadden et al. |
| 2012/0244117 A1 | 9/2012 | Egan et al. |
| 2013/0164255 A1 | 6/2013 | Hadden et al. |
| 2013/0243723 A1 | 9/2013 | Hadden et al. |
| 2014/0010779 A1 | 1/2014 | Hadden |
| 2014/0010780 A1 | 1/2014 | Hadden |
| 2014/0023593 A1 | 1/2014 | Hadden |
| 2014/0348782 A1 | 11/2014 | Hadden |
| 2014/0348783 A1 | 11/2014 | Hadden |

FOREIGN PATENT DOCUMENTS

| | | |
|---|---|---|
| EP | 0 433 765 A1 | 6/1991 |
| EP | 0 974 357 A1 | 1/2000 |
| EP | 0 789 588 B1 | 1/2005 |
| EP | 0 787 008 B1 | 1/2009 |
| EP | 1 653 912 B1 | 10/2011 |
| EP | 1 998 811 B1 | 10/2012 |
| JP | 8-511166 A | 11/1996 |
| JP | 10-509955 | 9/1998 |
| JP | 11-504814 A | 5/1999 |
| JP | 2002-531521 A | 9/2002 |
| JP | 2008-502605 A | 1/2008 |
| JP | 2009-530308 A | 8/2009 |
| JP | 2009-197032 A | 9/2009 |
| WO | WO 87/06830 A1 | 11/1987 |
| WO | WO 89/09619 A1 | 10/1989 |
| WO | WO 94/13314 A1 | 6/1994 |
| WO | WO 95/04548 A1 | 2/1995 |
| WO | WO 96/15800 A1 | 5/1996 |
| WO | WO 96/15808 A1 | 5/1996 |
| WO | WO 96/34956 A1 | 11/1996 |
| WO | WO 97/31119 A1 | 8/1997 |
| WO | WO 99/20788 A1 | 4/1999 |
| WO | WO 99/40938 A2 | 8/1999 |
| WO | WO 00/06723 A1 | 2/2000 |
| WO | WO 00/33870 A2 | 6/2000 |
| WO | WO 01/24771 A1 | 4/2001 |
| WO | WO 02/34119 A2 | 5/2002 |
| WO | WO 03/035004 A2 | 5/2003 |
| WO | WO 03/061566 A2 | 7/2003 |
| WO | WO 2005/025494 A2 | 3/2005 |
| WO | WO 2005/120550 A2 | 12/2005 |
| WO | WO 2005/123120 A1 | 12/2005 |
| WO | WO 2007/067782 A2 | 6/2007 |
| WO | WO 2007/136910 A2 | 11/2007 |
| WO | WO 2008/014220 A2 | 1/2008 |

(56) References Cited

FOREIGN PATENT DOCUMENTS

| WO | WO 2008/101154 A2 | 8/2008 |
|---|---|---|
| WO | WO 2008/133983 A1 | 11/2008 |
| WO | WO 2009/070639 A1 | 6/2009 |
| WO | WO 2009/137238 A2 | 11/2009 |
| WO | WO 2009/146392 A1 | 12/2009 |
| WO | WO 2010/132867 A1 | 11/2010 |
| WO | WO 2011/072006 A1 | 6/2011 |
| WO | WO 2012/037551 A2 | 3/2012 |

OTHER PUBLICATIONS

Hadden et al., (Arch Otolaryngol Head Neck Surg. Apr. 1994;120(4):395-403).*
Tarle (Anticancer Res. May-Jun. 1993;13(3):769-77; abstract only).*
Cavaillon, Pro- versus Anti-Inflammatory Cytokines: Myth or Reality. Cell Mol Biol. 2001;47(4):695-702.
Heath et al., Cytokines as immunological adjuvants. Vaccine. 1992;10(7):427-34. Review.
Sano et al., CpG Oligodeoxynucleotides as a Future Vaccine for Allergic Diseases. Allergol Intl. 2005;54:17-23.
Simmons et al., GM-CSF as a systemic adjuvant in a phase II prostate cancer vaccine trial. Prostate. Jun. 1, 1999;39(4):291-7.
Chen et al., Serum and mucosal immune responses to an inactivated influenza virus vaccine induced by epidermal powder immunization. J Virol. Sep. 2001;75(17):7956-65.
Marschner et al., CpG Odn enhance antigen-specific NKT cell activation via plasmacytoid dendritic cells. Eur J Immunol. Aug. 2005;35(8):2347-57.
International Search Report and Written Opinion dated Jan. 11, 2008 for Application No. PCT/US07/74156.
International Preliminary Report on Patentability dated Jan. 27, 2009 for Application No. PCT/US07/74156.
Albert et al., Dendritic cells acquire antigen from apoptotic cells and induce class I-restricted CTLs. Nature. Mar. 5, 1998;392(6671):86-9.
Almand et al., Clinical significance of defective dendritic cell differentiation in cancer. Clin Cancer Res. May 2000;6(5):1755-66.
Alvarez et al., Human T cell growth factor. I. Optimal conditions for its production. J Immunol. Sep. 1979;123(3):977-83.
Bajénoff et al., Stromal cell networks regulate lymphocyte entry, migration, and territoriality in lymph nodes. Immunity. Dec. 1, 2006;25(6):989-1001.
Banchereau et al. Immunobiology of dendritic cells. Annu Rev Immunol. 2000;18:767-811.
Barrera et al., Clinical and pathological bio-responses induced with a cytokine mixture (IRX-2) in patients with oral cavity squamous cell carcinoma. Clinical and Applied Immunology Rev. 2001;1:181-5.
Barrera et al., Clinical and pathological responses induced by a neoadjuvant treatment with a cytokine mixture (IRX-2) in oral cavity squamous cell carcinoma of head and neck. Int J Immunorehab. 2000;2(3):29-32.
Barrera et al., Combination immunotherapy of squamous cell carcinoma of the head and neck: a phase 2 trial. Arch Otolaryngol Head Neck Surg. Mar. 2000;126(3):345-51.
Barrera et al., Neoadjuvant immunological treatment with IRX-2 in patients with advanced oral cavity squamous cell carinoma of the head and neck induces clinical and histological responses. First World Congress on Head and Neck Oncology. 1998:1017-20.
Barrera et al., Nursing care makes a difference. Application of the Omaha System. Outcomes Manag. Oct.-Dec. 2003;7(4):181-5.
Belldegrun et al., Adoptive immunotherapy of urologic tumors. Urologic Oncology. Cancer Treatment and Research. 1989;46:213-33.
Belldegrun et al., Human tumor infiltrating lymphocytes. Analysis of lymphokine mRNA expression and relevance to cancer immunotherapy. J Immunol. Jun. 15, 1989;142(12):4520-6.

Bellone et al., Cancer immunotherapy: synthetic and natural peptides in the balance. Immunol Today. Oct. 1999;20(10):457-62.
Bellone et al., Processing of engulfed apoptotic bodies yields T cell epitopes. J Immunol. Dec. 1, 1997;159(11):5391-9.
Bender et al., Improved methods for the generation of dendritic cells from nonproliferating progenitors in human blood. J Immunol Methods. Sep. 27, 1996;196(2):121-35.
Berd et al., Effect of low dose cyclophosphamide on the immune system of cancer patients: reduction of T-suppressor function without depletion of the CD8+ subset. Cancer Res. Jun. 15, 1987;47(12):3317-21.
Berd et al., Potentiation of human cell-mediated and humoral immunity by low-dose cyclophosphamide. Cancer Res. Nov. 1984;44(11):5439-43.
Berd, Low doses of chemotherapy to inhibit suppressor T cells. Immunity to Cancer II. 1989;288:449-58.
Beuth et al., Thymosin alpha(1) application augments immune response and down-regulates tumor weight and organ colonization in BALB/c-mice. Cancer Lett. Oct. 16, 2000;159(1):9-13.
Borden, Interferons: rationale for clinical trials in neoplastic disease. Ann Intern Med. Sep. 1979;91(3):472-9. Review.
Borysiewicz et al., A recombinant vaccinia virus encoding human papillomavirus types 16 and 18, E6 and E7 proteins as immunotherapy for cervical cancer. Lancet. Jun. 1, 1996;347(9014):1523-7.
Brandwein, IRX-2: a natural cytokine stimulant for cancer vaccines. Session V: Strategies for immunization. Cancer Immunol Immunotherapy. Mar. 2003;52:S17-18, 30.
Cella et al , Inflammatory stimuli induce accumulation of MHC class II complexes on dendritic cells. Nature. Aug. 21, 1997;388(6644):782-7.
Cella et al., Ligation of CD40 on dendritic cells triggers production of high levels of interleukin-12 and enhances T cell stimulatory capacity: T-T help via APC activation. J Exp Med. Aug. 1, 1996;184(2):747-52.
Chang et al., Overview of interleukin-2 as an immunotherapeutic agent. Semin Surg Oncol. 1989;5(6):385-90. Review.
Chaux et al , Inflammatory cells infiltrating human colorectal carcinomas express HLA class II but not B7-1 and B7-2 costimulatory molecules of the T-cell activation. Lab Invest. May 1996;74(5):975-83.
Chilson et al., Mitogenic lectins bind to the antigen receptor on human lymphocytes. Eur J Immunol. Feb. 1989;19(2):389-96.
Chirigos et al., Immunotherapeutic agents: their role in cellular immunity and their therapeutic potential. Springer Semin Immunopathol.1985;8(4):327-46.
Cirelli et al., Interferons in human papillomavirus infections. Antiviral Res. Jul. 1994;24(2-3):191-204.
Clerici et al., An Occam's razor approach to the immunopathogenesis of HIV infection. AIDS. 1995;9 Suppl A:S33-40.
Cohen et al., Pronounced acute immunosuppression in vivo mediated by HIV Tat challenge. Proc Natl Acad Sci U S A. Sep. 14, 1999;96(19):10842-7.
Coles et al., Adjuvant effect of aluminium monostearate paraffin gels on antitoxin response. J Pharm Pharmacol. 1965;17:87S-91S.
Cortesina et al., Interleukin-2 injected around tumor-draining lymph nodes in head and neck cancer. Head Neck. Mar.-Apr. 1991;13(2):125-31.
Cortesina et al., Temporary regression of recurrent squamous cell carcinoma of the head and neck is achieved with a low but not with a high dose of recombinant interleukin 2 injected perilymphatically. Br J Cancer. Mar. 1994;69(3):572-6.
Cortesina et al., Treatment of recurrent squamous cell carcinoma of the head and neck with low doses of interleukin-2 injected perilymphatically. Cancer. Dec. 15, 1988;62(12):2482-5.
Cowens et al , Inhibition of the development of suppressor cells in culture by 4-hydroperoxycyclophosphamide. J Immunol. 1984;132:95-100.
Cozzolino et al., Characterization of cells from invaded lymph nodes in patients with solid tumors. Lymphokine requirement for tumor-specific lymphoproliferative response. J Exp Med. Aug. 1, 1987;166(2):303-18.

(56) References Cited

OTHER PUBLICATIONS

Cross et al., Administration of a prostaglandin synthetase inhibitor associated with an increased immune cell infiltrate in squamous cell carcinoma of the head and neck. Arch Otolaryngol Head Neck Surg. May 1992;118(5):526-8.
Czystowska et al., Mechanisms of T-cell protection from death by IRX-2: a new immunotherapeutic. Cancer Immunol Immunother. Apr. 2011;60(4):495-506. doi: 10.1007/s00262-010-0951-9. Epub Dec. 23, 2010.
Dallal et al., The dendritic cell and human cancer vaccines. Curr Opin Immunol. Oct. 2000;12(5):583-8.
De Stefani et al., Improved survival with perilymphatic interleukin 2 in patients with resectable squamous cell carcinoma of the oral cavity and oropharynx. Cancer. Jul. 1, 2002;95(1):90-7.
De Vries et al., Effective migration of antigen-pulsed dendritic cells to lymph nodes in melanoma patients is determined by their maturation state. Cancer Res. Jan. 1, 2003;63(1):12-7.
Deans et al., CD45R as a primary signal transducer stimulating IL-2 and IL-2R mRNA synthesis by CD3-4-8-thymocytes. J Immunol. Oct. 15, 1989;143(8):2425-30.
Deepe et al., Pharmacological modulation of suppressor cell activity in mice with disseminated histoplasmosis. Infect Immun. Jul. 1983;41(1):114-20.
Den Otter et al., Local therapy of cancer with free IL-2. Cancer Immunol Immunother. Jul. 2008;57(7):931-50. doi: 10.1007/s00262-008-0455-z.
Dueñas-Gonzalez et al., A pilot study of perilymphatic leukocyte cytokine mixture (IRX-2) as neoadjuvant treatment for early stage cervical carcinoma. Int Immunopharmacol. Jun. 2002;2(7):1007-16.
Dunn et al., Dendritic cells and HNSCC: a potential treatment option? Oncol Rep. 2005;13:3-10.
Eby, Treatment of acute lymphocytic leukemia using zinc adjuvant with chemotherapy and radiation—a case history and hypothesis. Med Hypotheses. 2005;64(6):1124-6.
Egan et al., IRX-2, a novel in vivo immunotherapeutic, induces maturation and activation of human dendritic cells in vitro. J Immunother. 2007;30(6):624-33.
Ehrke, Immunomodulation in cancer therapeutics. Int Immunopharmacol. Aug. 2003;3(8):1105-19.
Favalli et al., Modulation of natural killer activity by thymosin alpha 1 and interferon. Cancer Immunol Immunother. 1985;20(3):189-92.
Ferraro et al., Co-delivery of PSA and PSMA DNA vaccines with electroporation induces potent immune responses. Hum Vaccin. Jan.-Feb. 2011;7 Suppl:120-7. Epub Jan. 1, 2011.
Forni et al., Interleukin 2 activated tumor inhibition in vivo depends on the systemic involvement of host immunoreactivity. J Immunol. Jun. 1, 1987;138(11):4033-41.
Frillingos et al., Appearance of thymosin alpha 1 in supernatants of monocytes incubated with prothymosin alpha. Arch Biochem Biophys.Jul. 1992;296(1):256-63.
Gabrilovich et al., Decreased antigen presentation by dendritic cells in patients with breast cancer. Clin Cancer Res. Mar. 1997;3(3):483-90.
Gabrilovich et al., Dendritic cells in antitumor immune responses. I. Defective antigen presentation in tumor-bearing hosts. Cell Immunol. May 25, 1996;170(1):101-10.
Gabrilovich et al., Production of vascular endothelial growth factor by human tumors inhibits the functional maturation of dendritic cells. Nat Med. Oct. 1996;2(10):1096-103.
Gabrilovich et al., Vascular endothelial growth factor inhibits the development of dendritic cells and dramatically affects the differentiation of multiple hematopoietic lineages in vivo. Blood. Dec. 1, 1998;92(11):4150-66.
Gallo et al., Cyclooxygenase-2 pathway correlates with VEGF expression in head and neck cancer. Implications for tumor angiogenesis and metastasis. Neoplasia. Jan.-Feb. 2001;3(1):53-61.
Galon et al., Type, density, and location of immune cells within human colorectal tumors predict clinical outcome. Science. Sep. 29, 2006;313(5795):1960-4.

Garaci et al., Thymosin alpha 1 in the treatment of cancer: from basic research to clinical application. Int J Immunopharmacol. Dec. 2000;22(12):1067-76. Review.
Garaci, Thymosin alphal: a historical overview. Ann N Y Acad Sci. Sep. 2007;1112:14-20. Epub Jun. 13, 2007.
Gearing et al., Production and assay of the interleukins. J Immunol Methods. Oct. 24, 1985;83(1):1-27.
Gillis et al., T cell growth factor: parameters of production and a quantitative microassay for activity. J Immunol. Jun. 1978;120(6):2027-32.
Goldstein et al., The role of interferon in cancer therapy: a current perspective. CA Cancer J Clin. Sep.-Oct. 1988;38(5):258-77.
Goldstein et al., Thymosin alphal: isolation and sequence analysis of an immunologically active thymic polypeptide. Proc Natl Acad Sci U S A. Feb. 1977;74(2):725-9.
Goldstein, Thymosin α1: chemistry, mechanism of action and clinical applications. Combination Therapies. Plenum Press. 1993;2:39-48.
Gollapudi et al, Effect of ciprofloxacin on mitogen-stimulated lymphocyte proliferation. Antimicrob Agents Chemother. Feb. 1986;29(2):337-8.
Hadden et al., A trial of IRX-2 in patients with squamous cell carcinomas of the head and neck. Int Immunopharmacol. Aug. 2003;3(8):1073-81.
Hadden et al., Immunopharmacologic bases of immunotherapy. Clin Physiol Biochem. 1985;3(2-3):111-9. Review.
Hadden et al., Immunopharmacology. Immunomodulation and immunotherapy. JAMA. Nov. 25, 1992;268(20):2964-9.
Hadden et al., Immunotherapy with natural interleukins and/or thymosin alpha 1 potently augments T-lymphocyte responses of hydrocortisone-treated aged mice. Int J Immunopharmacol. Oct. 1995;17(10):821-8.
Hadden et al., Interleukins and contrasuppression induce immune regression of head and neck cancer. Arch Otolaryngol Head Neck Surg. Apr. 1994;120(4):395-403.
Hadden et al., IRX-2 and thymosin alphal (Zadaxin) increase T lymphocytes in T lymphocytopenic mice and humans. Ann N Y Acad Sci. Sep. 2007;1112:245-55. Epub Jun. 28, 2007.
Hadden et al., Lymphocyte blast transformation. I. Demonstration of adrenergic receptors in human peripheral lymphocytes. Cell Immunol. Dec. 1970;1(6):583-95.
Hadden et al., Mixed interleukins and thymosin fraction V synergistically induce T lymphocyte development in hydrocortisone-treated aged mice. Cell Immunol. Oct. 1, 1992;144(1):228-36.
Hadden et al., Strategies of immune reconstitution: effects of lymphokines on murine T cell development in vitro and in vivo. Life Sci. 1989;44(13):v-xii.
Hadden et al., The characterization of immunotherapeutic agents. Immunopharmacol Rev. Plenum Press. New York. 1990;1:1-64.
Hadden, Aspects of the immunopharmacology of thymosin alpha-1. Clin Appl Rev. Mar. 2001;1(3-4):187-91.
Hadden, Combination immunotherapy. Intl Immunopharm. 2003;3:1049-50.
Hadden, Immunodeficiency and cancer: prospects for correction. Int Immunopharmacol. Aug. 2003;3(8):1061-71.
Hadden, Immunology of Head and Neck Cancer. Contemporary Issues in Oral Cancer. New York. Oxford University Press. 2000:72-95.
Hadden, Immunology of head and neck cancer: prospects for immunotherapy. Clin Immunotherapy. 1995;3:362-85.
Hadden, Immunopharmacology. Immunomodulation and immunotherapy. JAMA. Nov. 27, 1987;258(20):3005-10.
Hadden, Immunostimulants. Immunol Today. Jun. 1993;14(6):275-80. Review.
Hadden, Immunotherapy of human immunodeficiency virus infection. TIPS review. 1991;12:107-11.
Hadden, T-cell adjuvants. Int J Immunopharmacol. Sep. 1994;16(9):703-10.
Hadden, The immunology and immunotherapy of breast cancer: an update. Int J Immunopharmacol. Feb. 1999;21(2):79-101.
Hadden, The immunopharmacology of head and neck cancer: an update. Int J Immunopharmacol. Nov.-Dec. 1997;19(11-12):629-44.

(56) References Cited

OTHER PUBLICATIONS

Hadden, The treatment of zinc deficiency is an immunotherapy. Int J Immunopharmacol. Sep. 19995;17(9):697-701.
Hadden, Thymic endocrinology. Ann N Y Acad Sci. May 1, 1998;840:352-8.
Hadden, Thymic endocrinology. Int J Immunopharmacol. Apr. 1992;14(3):345-52. Review.
Hank et al., Monoclonal antibodies, cytokines and fusion proteins in the treatment of malignant disease. Cancer Chemother Biol Resp Modif. 1999;18:210-22.
Hart, Dendritic cells: unique leukocyte populations which control the primary immune response. Blood. Nov. 1, 1997;90(9):3245-87.
Hengst et al., Cooperation between cyclophosphamide tumoricidal activity and host antitumor immunity in the cure of mice bearing large MOPC-315 tumors. Cancer Res. Jun. 1981;41(6):2163-7.
Hengst et al., Importance of timing in cyclophosphamide therapy of MOPC-315 tumor-bearing mice. Cancer Res. Jul. 1980;40(7):2135-41.
Hillman et al., Systemic treatment with interleukin-4 induces regression of pulmonary metastases in a murine renal cell carcinoma model. Cell Immunol. Feb. 1995;160(2):257-63.
Hirsch et al., Immunostimulation of patients with head and neck cancer. In vitro and preliminary clinical experiences. Arch Otolaryngol. May 1983;109(5):298-301.
Hoffmann et al., Alterations in the frequency of dendritic cell subsets in the peripheral circulation of patients with squamous cell carcinomas of the head and neck. Clin Cancer Res. Jun. 2002;8(6):1787-93.
Holtl et al., Immunotherapy of metastatic renal cell carcinoma with tumor lysate-pulsed autologous dendritic cells. Clin Cancer Res. Nov. 2002;8(11):3369-76.
Hwu et al., The genetic modification of T cells for cancer therapy: an overview of laboratory and clinical trials. Cancer Detect Prev. 1994;18(1):43-50. Review.
Hwu et al., The use of gene-modified tumor-infiltrating lymphocytes for cancer therapy. Ann N Y Acad Sci. May 31, 1994;716:188-97; Discussion 197-203.Review.
Johnston-Early et al., Delayed hypersensitivity skin testing as a prognostic indicator in patients with small cell lung cancer. Cancer. Oct. 15, 1983;52(8):1395-400.
Jordan et al., Optimal analysis of composite cytokine responses during alloreactivity. J Immunol Methods. Feb. 1, 2002;260(1-2):1-14.
June et al., Evidence for the involvement of three distinct signals in the induction of IL-2 gene expression in human T lymphocytes. J Immunol. Jul. 1, 1989;143(1):153-61.
Kaech et al., Effector and memory T-cell differentiation: implications for vaccine development. Nat Rev Immunol. Apr. 2002;2(4):251-62.
Kalinski et al., Prostaglandin E(2) is a selective inducer of interleukin-12 p40 (IL-12p40) production and an inhibitor of bioactive IL-12p70 heterodimer. Blood. Jun. 1, 2001;97(11):3466-9.
Kameda et al., Mixed lymphokines in low dose prolong life in cyclophosphamide-treated melanoma-bearing mice. Int J Immunother. 1992;8:1-5.
Kaminuma et al., Interleukin-5 production by peripheral blood mononuclear cells of asthmatic patients is suppressed by T-440: relation to phosphodiesterase inhibition. J Pharmacol Exp Ther. Oct. 1996;279(1):240-6.
Katsuyuki et al., Clinical trials of immunotherapy for advanced prostate cancer. Urol Oncol. 2000;5:265-73.
Kavanaugh et al., Immunologic dysfunction in cancer. Hematol Oncol Clin North Am. Aug. 1996;10(4):927-51.
Kidd, Th1/Th2 balance: the hypothesis, its limitations, and implications for health and disease. Altern Med Rev. Aug. 2003;8(3):223-46.
Kleindienst et al., Endogenous dendritic cells are required for amplification of T cell responses induced by dendritic cell vaccines in vivo. J Immunol. Mar. 15, 2003;170(6):2817-23.

Koopman et al., Reversal of human papillomavirus immune escape using IRX-2 and a toll-like receptor 3 agonist. Jan. 1, 2011. scripties.umcg.eldoc.ub.rug.nl/root/geneeskunde/2010/KoopmanMaaike/ [last accessed Jan. 22, 2011].
Kovacs et al., Increases in CD4 T lymphocytes with intermittent courses of interleukin-2 in patients with human immunodeficiency virus infection. A preliminary study. N Engl J Med. Mar. 2, 1995;332(9):567-75.
Lafferty et al., Immunological induction of T lymphocytes: role of antigen and the lymphocyte costimulator. Blood Cells 1978;4(3):395-406.
Lahiri et al., Engagement of TLR signaling as adjuvant: towards smarter vaccine and beyond. Vaccine. Dec. 9, 2008;26(52):6777-83.
Langenkamp et al., Kinetics of dendritic cell activation: impact on priming of TH1, TH2 and nonpolarized T cells. Nat Immunol. Oct. 2000;1(4):311-6.
Lanzavecchia et al., Understanding the generation and function of memory T cell subsets. Curr Opin Immunol. Jun. 2005;17(3):326-32.
Lopez et al., Biochemotherapy with thymosin alpha 1, interleukin-2 and dacarbazine in patients with metastatic melanoma: clinical and immunological effects. Ann Oncol. Oct. 1994;5(8):741-6.
Lopez-Rodriguez et al., Interleukin-2 killer cells: in vitro evaluation of combination with prothymosin alpha. Lymphokine Cytokine Res. Jun. 1994;13(3):175-82.
Lou et al., Dendritic cells strongly boost the antitumor activity of adoptively transferred T cells in vivo. Cancer Res. Sep. 15, 2004;64(18):6783-90.
Maass et al., Priming of tumor-specific T cells in the draining lymph nodes after immunization with interleukin 2-secreting tumor cells: three consecutive stages may be required for successful tumor vaccination. Proc Natl Acad Sci U S A. Jun. 6, 1995;92(12):5540-4.
Mackall et al., Age, thymopoiesis, and CD4+ T-lymphocyte regeneration after intensive chemotherapy. N Engl J Med. Jan. 19, 1995;332(3):143-9.
Mackall, T-cell immunodeficiency following cytotoxic antineoplastic therapy: a review. Stem Cells. 2000;18(1):10-8.
Maclean et al., Enhancing the effect of THERATOPE STn-KLH cancer vaccine in patients with metastatic breast cancer by pretreatment with low-dose intravenous cyclophosphamide. J Immunother Emphasis Tumor Immunol. Jul. 1996;19(4):309-16.
Mantovani et al., Macrophage polarization: tumor-associated macrophages as a paradigm for polarized M2 mononuclear phagocytes. Trends Immunol. Nov. 2002;23(11):549-55. Review.
Maric et al., Immunostimulatory activity of prothymosin-alpha in senescence. Ann N Y Acad Sci. 1991;621:148-58.
Maric et al., In vivo effect of prothymosin-alpha 1 on humoral and cell-mediated immune responses in the young rat. Int J Neurosci.Jul. 1991;59(1-3):135-42.
Masek et al., Neuroendocrine immune interactions in health and disease. Int Immunopharmacol. Aug. 2003;3(8):1235-46.
Mastino et al., Combination therapy with thymosin alpha 1 potentiates the anti-tumor activity of interleukin-2 with cyclophosphamide in the treatment of the Lewis lung carcinoma in mice. Int J Cancer. Feb. 1, 1992;50(3):493-9.
Mastino et al., Thymosin alpha 1 potentiates interleukin 2-induced cytotoxic activity in mice. Cell Immunol. Mar. 1991;133(1):196-205.
Mastrangelo et al., Active specific immunization in the treatment of patients with melanoma. Semin Oncol. Dec. 1996;23(6):773-81.
Mattijssen et al., Clinical and immunopathological results of a phase II study of perilymphatically injected recombinant interleukin-2 in locally far advanced, nonpretreated head and neck squamous cell carcinoma. J Immunother (1991). Feb. 1991;10(1):63-8.
McLaughlin et al., Improved immunotherapy of a recombinant carcinoembryonic antigen vaccinia vaccine when given in combination with interleukin-2. Cancer Res. May 15, 1996;56(10):2361-7.
Mempel et al., Rulers over randomness: stroma cells guide lymphocyte migration in lymph nodes. Immunity. Dec. 2006;25(6):867-9.

(56) References Cited

OTHER PUBLICATIONS

Meneses et al., Histologic findings in patients with head and neck squamous cell carcinoma receiving perilymphatic natural cytokine mixture (IRX-2) prior to surgery. Arch Pathol Lab Med. May 1998;122(5):447-54.

Meneses et al., Lymph node histology in head and neck cancer: impact of immunotherapy with IRX-2. Int Immunopharmacol. Aug. 2003;3(8):1083-91.

Middel et al., Sinus histiocytosis with massive lymphadenopathy: evidence for its relationship to macrophages and for a cytokine-related disorder. Histopathology. Dec. 1999;35(6):525-33.

Mikysková et al., Local cytokine treatment of HPV16-associated tumors results in inhibition of their lung metastases. Clin Exp Metastasis. 2001;18(7):581-7.

Mitchell et al., Promotion of human T lymphocyte proliferation by IL-4. J Immunol. Mar. 1, 1989;142(5):1548-57.

Mokyr et al., Role of antitumor immunity in cyclophosphamide-induced rejection of subcutaneous nonpalpable MOPC-315 tumors. Cancer Res. Mar. 1982;42(3):974-9.

Moody et al., Thymosin alpha 1 down-regulates the growth of human non-small cell lung cancer cells in vitro and in vivo. Cancer Res. Nov. 1, 1993;53(21):5214-8.

Morgan et al., Selective in vitro growth of T lymphocytes from normal human bone marrows. Science. Sep. 10, 1976;193(4257):1007-8.

Mule, Mechanistic aspects of successful immunotherapy of established pulmonary metastases by the systemic administration of high-dose recombinant interleukin-2. Prog Clin Biol Res. 1987;244:79-91.

Murphy et al., Infusion of dendritic cells pulsed with HLA-A2-specific prostate-specific membrane antigen peptides: a phase II prostate cancer vaccine trial involving patients with hormone-refractory metastatic disease. Prostate. Jan. 1, 1999;38(1):73-8.

Musiani et al., Effect of low doses of interleukin-2 injected perilymphatically and peritumorally in patients with advanced primary head and neck squamous cell carcinoma. J Biol Response Mod. Dec. 1989;8(6):571-8.

Naylor et al., Preclinical and clinical studies on immunogenicity and safety of the HIV-1 p17-based synthetic peptide AIDS vaccine—HGP-30-KLH. Int J Immunopharmacol. 1991;13 Suppl 1:117-27.

Naylor et al., Enhancement of Peptide Specific DTH with Combination Cytokines. Presented CSHL Meeting Dec. 4-7, 2003. Molecular Approaches to Vaccine Design. p. 28.

Naylor et al., Immunopharmacology of thymosin alpha1 and cytokine synergy. Ann N Y Acad Sci. Sep. 2007;1112:235-44. Epub Jun. 13, 2007.

Naylor et al., IRX-2 increases the T cell-specific immune response to protein/peptide vaccines. Vaccine. Oct. 8, 2010;28(43):7054-62. Epub Aug. 13, 2010.

Naylor et al., Preclinical studies with an IRX-2 enhanced prostate vaccine. J Urology. 2008;179(4):45.

Naylor et al., Preclinical studies with IRX-2 and thymosin alpha1 in combination therapy. Ann N Y Acad Sci. Apr. 2010;1194:162-8.

Naylor et al., T cell targeted immune enhancement yields effective T cell adjuvants. Int Immunopharmacol. Aug. 2003;3(8):1205-15.

Nohria et al., Cytokines as potential vaccine adjuvants. Biotherapy. 1994;7(3-4):261-9.

O'Hagan et al., Recent developments in adjuvants for vaccines against infectious diseases. Biomol Eng. Oct. 15, 2001;18(3):69-85.

Overwijk et al., Creating therapeutic cancer vaccines: notes from the battlefield. Trends Immunol. Jan. 2001;22(1):5-7.

Paetkeau et al., Proliferation of murine thymic lymphocytes in vitro is mediated by the concanavalin A-induced release of a lymphokine (costimulator). J Immunol. Oct. 1976;117(4):1320-4.

Panje, Regression of head and neck carcinoma with a prostaglandin-synthesis inhibitor. Arch Otolaryngol. Nov. 1981;107(11):658-63.

Pulley et al., Intravenous, intralesional and endolymphatic administration of lymphokines in human cancer. Lymphokine Res. 1986;5 Suppl 1:S157-63.

Qin et al., Isolation and identification of a new thymic peptide from calf thymus. Biochem (Mosc). Aug. 2004;69(8):921-5.

Randolph, Dendritic cell migration to lymph nodes: cytokines, chemokines, and lipid mediators. Semin Immunol. Oct. 2001;13(5):267-74.

Rapidis et al., Immunotherapy of head and neck cancer: current and future considerations. J Oncol. 2009;2009:346345. doi: 10.1155/2009/346345. Epub Aug. 9, 2009. 11 pages.

Rasi et al., Anti-tumor effect of combined treatment with thymosin alpha 1 and interleukin-2 after 5-fluorouracil in liver metastases from colorectal cancer in rats. Int J Cancer. Jun. 1, 1994;57(5):701-5.

Rasi et al., Combined treatment with thymosin-alpha1 and low dose interferon-alpha after dacarbazine in advanced melanoma. Melanoma Res. Apr. 2000;10(2):189-92.

Ridgway, The first 1000 dendritic cell vaccinees. Cancer Invest. 2003;21(6):873-86.

Riesbeck et al., Limited effects of temafloxacin compared with ciprofloxacin on T-lymphocyte function. Antimicrob Agents Chemother. Apr. 1994;38(4):879-82.

Riesenbeck et al., Superinduction of cytokine gene transcription by ciprofloxacin. J Immunol. Jul. 1, 1994;153(1):343-52.

Rogers et al., CD28, Ox-40, LFA-1, and CD4 modulation of Th1/Th2 differentiation is directly dependent on the dose of antigen. J Immunol. Mar. 15, 2000;164(6):2955-63.

Romani et al., Generation of mature dendritic cells from human blood. An improved method with special regard to clinical applicability. J Immunol Methods. Sep. 27, 1996;196(2):137-51.

Rosenberg et al., A progress report on the treatment of 157 patients with advanced cancer using lymphokine-activated killer cells and interleukin-2 or high-dose interleukin-2 alone. N Engl J Med. Apr. 9, 1987;316(15):889-97.

Rosenberg et al., Cancer immunotherapy: moving beyond current vaccines. Nat Med. Sep. 2004;10(9):909-15.

Rosenberg et al., Observations on the systemic administration of autologous lymphokine-activated killer cells and recombinant interleukin-2 to patients with metastatic cancer. N Engl J Med. Dec. 5, 1985;313(23):1485-92.

Rosenberg, Immunotherapy of cancer by systemic administration of lymphoid cells plus interleukin-2. J Biol Response Mod. Oct. 1984;3(5):501-11.

Rosenberg, The development of new immunotherapies for the treatment of cancer using interleukin-2. A review. Ann Surg. Aug. 1988;208(2):121-35. Review.

Saha et al., Zinc induces thymulin secretion from human thymic epithelial cells in vitro and augments splenocyte and thymocyte responses in vivo. Int J Immunopharmacol. Sep. 1995;17(9):729-33.

Saito et al., Spontaneous ex vivo apoptosis of peripheral blood mononuclear cells in patients with head and neck cancer. Clin Cancer Res. Jun. 1999;5(6):1263-73.

Sallusto et al., Dendritic cells use macropinocytosis and the mannose receptor to concentrate macromolecules in the major histocompatibility complex class II compartment: downregulation by cytokines and bacterial products. J Exp Med. Aug. 1, 1995;182(2):389-400.

Sallusto et al., Efficient presentation of soluble antigen by cultured human dendritic cells is maintained by granulocyte/macrophage colony-stimulating factor plus interleukin 4 and downregulated by tumor necrosis factor alpha. J Exp Med. Apr. 1, 1994;179(4):1109-18.

Schuler-Thurner et al., Rapid induction of tumor-specific type 1 T helper cells in metastatic melanoma patients by vaccination with mature, cryopreserved, peptide-loaded monocyte-derived dendritic cells. J Exp Med. May 20, 2002;195(10):1279-88.

Schuloff, Thymic peptide hormones: basic properties and clinical applications in cancer. Crit Rev Oncol Hematol. 1985;3(4):309-76. Review.

Scott et al., Cell-mediated immune response to human papillomavirus infection. Clin Diagn Lab Immunol. Mar. 2001;8(2):209-20.

(56) References Cited

OTHER PUBLICATIONS

Scott et al., Th1 Cytokine Patterns in Cervical Human Papillomavirus Infection. Clin Diagn Lab Immunol. Sep. 1999; 6(5): 751-5.
Silecchia et al., Efficacy of repeated cycles of chemo-immunotherapy with thymosin alpha1 and interleukin-2 after intraperitoneal 5-fluorouracil delivery. Cancer Immunol Immunother. Jul. 1999;48(4):172-8.
Sozzani et al., Differential regulation of chemokine receptors during dendritic cell maturation: a model for their trafficking properties. J Immunol. Aug. 1, 1998;161(3):1083-6.
Steinman et al., Avoiding horror autotoxicus: the importance of dendritic cells in peripheral T cell tolerance. Proc Natl Acad Sci U S A. Jan. 8, 2002;99(1):351-8. Epub Jan. 2, 2002.
Steinman, The dendritic cell system and its role in immunogenicity. Annu Rev Immunol. 1991;9:271-96.
Syrjanen, Human papillomavirus (HPV) in head and neck cancer. J Clin Virol. Mar. 2005;32 Suppl 1:S59-66.
Tagawa, Cytokine therapy for cancer. Curr Pharm Des. Apr. 2000;6(6):681-99.
Talmage et al., Activation of cytotoxic T cells by nonstimulating tumor cells and spleen cell factor(s). Proc Natl Acad Sci U S A. Oct. 1977;74(10):4610-4.
Tas et al., Depressed monocyte polarization and clustering of dendritic cells in patients with head and neck cancer: in vitro restoration of this immunosuppression by thymic hormones. Cancer Immunol Immunother. 1993;36(2):108-14.
Thurman et al., Comparative evaluation of multiple lymphoid and recombinant human interleukin-2 preparations. J Biol Response Mod. Feb. 1986;5(1):85-107.
Tjoa et al., Development of dendritic-cell based prostate cancer vaccine. Immunol Lett. Sep. 15, 2000;74(1):87-93.
Tjoa et al., Evaluation of phase I/II clinical trials in prostate cancer with dendritic cells and PSMA peptides. Prostate. Jun. 15, 1998;36(1):39-44.
Tzehoval et al., Thymosins alpha 1 and beta 4 potentiate the antigen-presenting capacity of macrophages. Immunopharmacol. Sep.-Oct. 1989;18(2):107-13.
Valente et al., Infiltrating leukocyte populations and T-lymphocyte subsets in head and neck squamous cell carcinomas from patients receiving perilymphatic injections of recombinant interleukin 2. A pathologic and immunophenotypic study. Mod Pathol. Nov. 1990;3(6):702-8.
Van Den Eynde et al., T cell defined tumor antigens. Curr Opin Immunol. Oct. 1997;9(5):684-93.
Van Lier et al, Immobilized anti-CD3 monoclonal antibodies induce accessory cell-independent lymphokine production, proliferation and helper activity in human T lymphocytes. Immunol. Sep. 1989;68(1):45-50.
Verastegui et al. Immunological approach in the evaluation of regional lymph nodes of patients with squamous cell carcinoma of the head and neck. Clin Immunol. Jan. 2002;102(1):37-47.
Verastegui et al., A natural cytokine mixture (IRX-2) and interference with immune suppression induce immune mobilization and regression of head and neck cancer. Int J Immunopharmacol. Nov.-Dec. 1997;19(11-12):619-27.
Verastegui et al., Long-term immune dysfunction after radiotherapy to the head and neck area. Int Immunopharmacol. Aug. 2003;3(8):1093-1104.
Verwilghen et al., Differences in the stimulating capacity of immobilized anti-CD3 monoclonal antibodies: variable dependence on interleukin-1 as a helper signal for T-cell activation. Immunol. Feb. 1991;72(2):269-76.
Vine et al., T4 cell activation by immobilized phytohemagglutinin: differential capacity to induce IL-2 responsiveness and IL-2 production. J Immunol. Oct. 15, 1988;141(8):2593-600.
Wang et al., Human tumor antigens for cancer vaccine development. Immunol Rev. Aug. 1999;170:85-100.
Webb et al., Mitogen-induced human lymphocyte activation in serum-free medium. Clin Immunol Immunopathol. Apr. 1973;1(3):304-10.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Whiteside et al., Antigen-processing machinery in human dendritic cells: up-regulation by maturation and down-regulation by tumor cells. J Immunol. Aug. 1, 2004;173(3):1526-34.
Whiteside et al., Evidence for local and systemic activation of immune cells by peritumoral injections of interleukin 2 in patients with advanced squamous cell carcinoma of the head and neck. Cancer Res. Dec. 1, 1993;53(23):5654-62.
Whiteside, Immunobiology and immunotherapy of head and neck cancer. Curr Oncol Rep. Jan. 2001;3(1):46-55.
Yang et al., The use of polyethylene glycol-modified interleukin-2 (PEG-IL-2) in the treatment of patients with metastatic renal cell carcinoma and melanoma. A phase I study and a randomized prospective study comparing IL-2 alone versus IL-2 combined with PEG-IL-2. Cancer. Aug. 15, 1995;76(4):687-94.
Dubey et al., Costimulatory requirements of naive CD4+ T cells. ICAM-1 or B7-1 can costimulate naive CD4 T cell activation but both are required for optimum response. J Immunol. Jul. 1, 1995;155(1):45-57.
Hodge et al., A triad of costimulatory molecules synergize to amplify T-cell activation. Cancer Res. Nov. 15, 1999;59(22):5800-7.
Krishnan et al., Toll-like receptor signal transduction. Exp Mol Med. Aug. 31, 2007;39(4):421-38.
Mellstedt et al., The challenge of biosimilars. Ann Oncol. Mar. 2008;19(3):411-9. Epub Sep. 14, 2007.
Müller et al., The advent of biosimilars: challenges and risks. Swiss Med Wkly. Jul. 1, 2014;144:w13980. doi: 10.4414/smw.2014.13980. eCollection 2014.

* cited by examiner

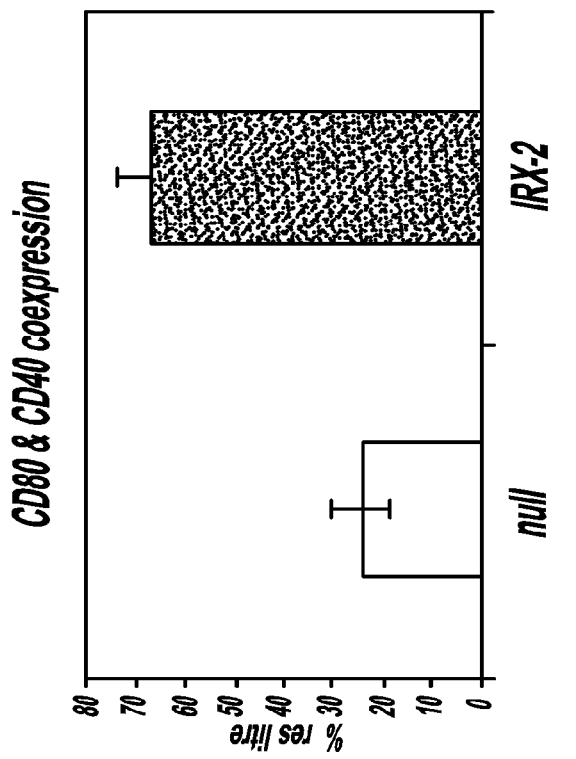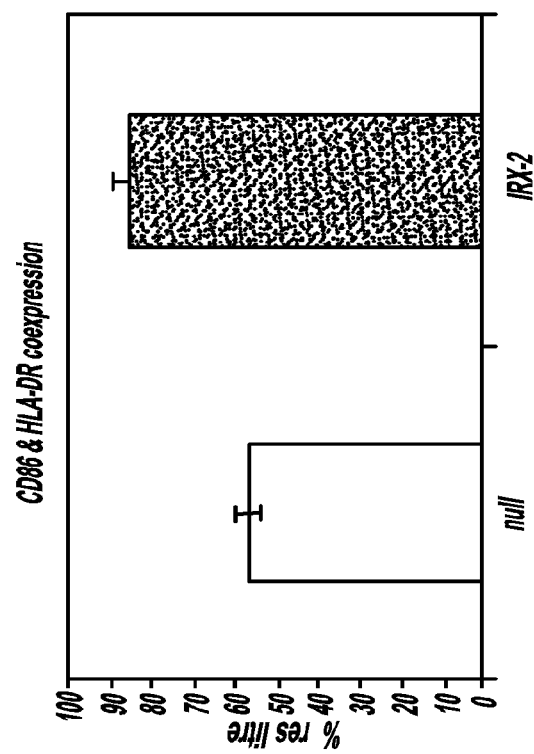
FIG - 19A

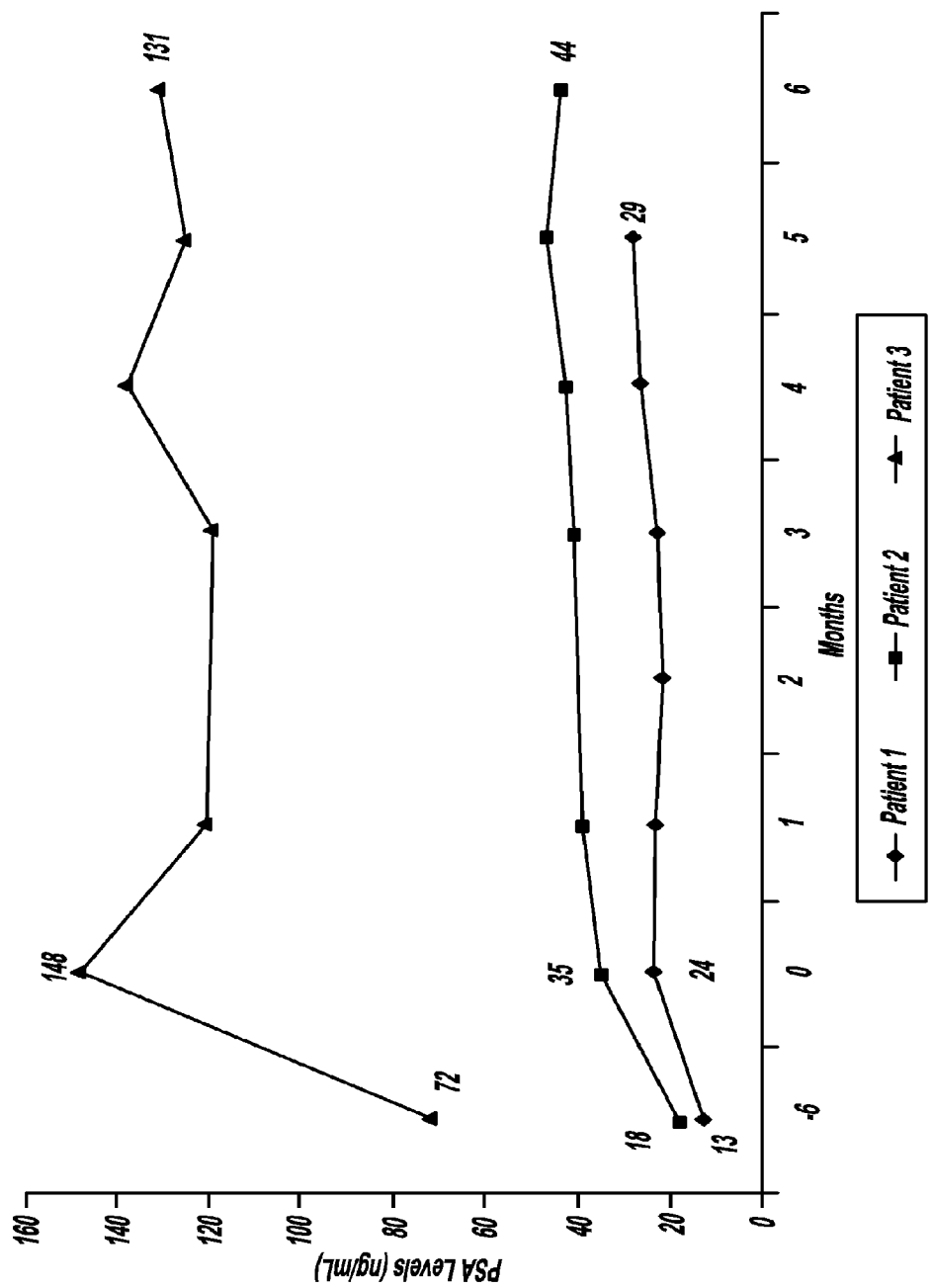

VACCINE IMMUNOTHERAPY

CROSS-REFERENCE TO RELATED APPLICATIONS

This application is a continuation which claims the benefit under 35 U.S.C. §120 of U.S. application Ser. No. 12/374,732, entitled "VACCINE IMMUNOTHERAPY" filed on Oct. 8, 2009, which is herein incorporated by reference in its entirety. Application Ser. No. 12/374,732 is a national stage filing under 35 U.S.C. § 371 of international application PCT/US2007/074156, entitled "VACCINE IMMUNOTHERAPY" filed on Jul. 24, 2007. Application PCT/US2007/074156 is a continuation which claims the benefit under 35 U.S.C. §120 of U.S. application Ser. No. 11/492,418, entitled "VACCINE IMMUNOTHERAPY" filed on Jul. 25, 2006, now abandoned, which is herein incorporated by reference in its entirety. Application Ser. No. 11/492,418 is a continuation-in-part which claims the benefit under 35 U.S.C. §120 of U.S. application Ser. No. 10/637,869, now U.S. Pat. No. 7,182,942, granted Feb. 7, 2007, entitled "VACCINE IMMUNOTHERAPY FOR IMMUNE SUPPRESSED PATIENTS" filed on Aug. 8, 2003, which is herein incorporated by reference in its entirety. Application Ser. No. 10/637,869 is a continuation-in-part which claims the benefit under 35 U.S.C. §120 of U.S. application Ser. No. 10/015,123, now U.S. Pat. No. 6,977,072, granted Dec. 20, 2005, entitled "VACCINE IMMUNOTHERAPY FOR IMMUNE SUPPRESSED PATIENTS" filed on Oct. 26, 2001, which is herein incorporated by reference in its entirety. Application Ser. No. 10/015,123 claims priority under 35 U.S.C. §119(e) to U.S. Provisional Application Ser. No. 60/243,912, entitled "VACCINE IMMUNOTHERAPY FOR IMMUNIZING CANCER PATIENTS TO CANCER ANTIGENS" filed on Oct. 27, 2000, which is herein incorporated by reference in its entirety.

BACKGROUND OF THE INVENTION

1. Technical Field

The present invention relates to vaccine immunotherapy. More specifically, the present invention relates to compositions and methods for eliciting an immune response to endogenous or exogenous peptide or protein antigens in patients having cancer or other antigen-producing disease states or lesions.

2. Background Art

It has become increasingly apparent that human cancers possess antigens, which, if acted upon by the host's immune system, can result in tumor regression. These antigens have been defined by both serological and cellular immune approaches, which have led to the definition of both B and T cell epitopes (Sahin, 1997; Van der Eynde, 1997; Wang, 1999). Based upon these results, it has become a goal of cancer immunotherapists to induce the regression of tumors. However, historically, successful efforts have been sporadic and generally minor in frequency and magnitude.

A fundamental problem in the effort to immunize cancer patients, i.e., against tumor antigens, is that the tumor-bearing state is associated with immunosuppressive mechanisms derived from both the tumor and the host's disturbed immune system (Kavanaugh, 1996), thereby making immunization difficult and until now impossible on a consistent basis. Immune suppression or depletion involves a reduced capacity of the immune system to respond. Such suppression can be drug-induced, i.e., by drug treatment, virus-induced, e.g., as in AIDS, or induced by a disease state such as cancer. The immune system in this condition is effectively turned off. In the case of a disease state such as cancer, the body is not able to protect itself against tumor antigens, thus allowing a tumor to grow and possibly metastasize.

A variety of tumor immunization strategies have been developed. All of these strategies are complex and deviate significantly from the conventional immunization strategies used for infectious diseases (see, e.g., Weber, 2000). One such tumor immunization strategy involves Theratope®, a sialyl Tn polysaccharide mucin antigen conjugated with keyhole limpet hemocyanin (KLH) and administered with Detox® mycobacterium adjuvant and low dose cyclophosphamide (Maclean, 1996). Use of this vaccine in patients with metastatic breast and ovarian cancer has yielded major clinical responses (i.e., greater than 50% tumor reduction) in only a low percentage of patients.

Gene therapy has also been attempted using viral constructs as expression vectors for genes expressing tumor antigens. For example, a recombinant vaccinia virus construct encoding modified forms of human papilloma virus (HPV) E6 and E7 protein sequences has been used for immunization of patients with cervical cancer. Vaccination with this construct yielded questionable clinical responses (Borysiewickz, 1996). See also, Sanda, 1999 wherein a recombinant vaccinia-PSA (prostate-specific antigen) construct was used as a vaccine in prostate cancer patients.

Another approach has been dendritic cell-mediated therapy, e.g., wherein dendritic cells were pulsed with oligopeptide fragments of prostate-specific membrane antigens (PSMA). The dendritic cells (with or without the priming PSMA antigens) were then administered to patients with metastatic prostate cancer. Major clinical responses were obtained in only a low percentage of patients (Murphy, 1999; see also, Tjoa, 2000).

Additionally, autologous tumors have been used with low dose cyclophosphamide and BCG (Bacillus Calmette-Guerin) to immunize cancer patients with malignant melanoma. However, few clinical responses were reported (Mastrangelo, 1996). Another strategy included using MAGE antigens with a variety of vaccine adjuvants. Again, this has yielded few, if any, responses in patients with malignant melanoma (personal communication, Thierry Boon).

Several patents to Doyle et al (U.S. Pat. Nos. 5,503,841; 5,800,810; 6,060,068; 5,643,565; and 5,100,664) disclose methods of enhancing the immune response in patients using interleukin 2 (IL-2). This method is disclosed for use in response to infectious diseases and primarily functions using antigens known to be immunogenic. Limited applicability was demonstrated. As disclosed above, the treatment of cancer is known to require different approaches. To date, treatment with IL-2 has shown minor effects in two cancers, renal cell and malignant melanoma (response rates less than 20%). It is generally considered ineffective in squamous cell head and neck and cervical cancer and in prostate cancer. Hence, it is not approved for these uses.

It is important to contrast prevention using known "classic" antigens of complex structure and high molecular weights in healthy patients vs. treatment (generally unsuccessful) with tumor antigens or peptides (general unsuccessful) in immunosuppressed patients (generally unsuccessful). The first is easy and our current viral vaccines attest to their efficacy. The latter is nearly impossible on a routine basis despite thirty years of intense effort.

Moreover, effective cancer vaccines require stimulation of cell-mediated immunity, perhaps even in preference to antibody production. As noted, despite numerous studies with various antigens, adjuvants and vaccine constructs, the clinical trial data to date have been disappointing. The critical events for a T cell mediated anti-cancer immune response are antigen presentation to T cells, primarily in the lymph nodes draining the site of the tumor or immunization, followed by T cell activation and migration to the peripheral sites. In fact, the uptake of the antigen by tissue macrophages, neutrophils and/or dendritic cells and presentation of processed peptides in combination with MHC class I and class II antigens to the T cells in the lymph node are crucial to a complete immune response. Key to a successful T cell immune activation is the generation of the appropriate cytokine environment to drive the immune response to a vaccine, at both the site of immunization and draining lymph nodes.

The kinetics of the immune response includes two phases. The first is the draining of the antigen and soluble proteins to the lymph nodes, where an initial immune activation occurs. Twenty four to forty eight hours later, antigen-presenting cells (APCs), most particularly dendritic cells, migrate from the site of immunization via the draining lymphatic ducts to the lymph node, where a second wave of presentation of antigen and activation occurs. More specifically, the APCs interact in the lymph node with precursor T helper cells via engagement of co-stimulatory receptors as well as T cell receptors to yield T helper 1 (Th1) cells and/or T helper 2 (Th2) cells. The ratio of these subsets controls subsequent development of either cell-mediated or humoral (antibody) immune responses (Th1 biasing towards DTH/cytotoxicity, whereas Th2 biases towards antibody production). Following the induction of these activated T cells, the immune response subsides, leaving predominately memory T cells, which are capable of responding upon re-exposure to antigen.

The critical events in this pathway are mediated by cytokines that bias the response in the direction of humoral or cellular immunity. Locally produced cytokines, such as IL-1, IL-2, IFN γγ, GM-CSF, IL6, TNF-α, IL-12 and IL-8, are associated with the recruitment of immune system cells, antigen uptake, dendritic cell maturation, dampening of T regulatory cell activity, T cell education and proliferation, and the development of Th1 cells (Naylor, 2003). The interdependence of the response means that the activity of any given cytokine depends on the occurrence of precursor events such that the simultaneous presence of multiple cytokines can have different effects at both the injection site and the draining lymph nodes, depending on the kinetics of cell responses to different cytokines.

The present invention utilizes the natural cytokine mixture (NCM) as disclosed in U.S. Pat. Nos. 5,632,983 and 5,698,194, issued to Applicant, to immunize patients, such as cancer patients or other patients with other antigen-producing lesions or disease states. More specifically, NCM (also referred to herein as IRX-2) has been previously shown in U.S. Pat. No. 5,698,194 to be effective in promoting T cell development and function in aged, immunosuppressed mice. NCM was shown to decrease the proportion of immature T cells and increase the proportion of mature T cells in the thymus. The NCM included IL-1, IL-2, IL-6, IL-8, IL-12, IFN-γ, TNF-α, GM-CSF, G-CSF, and IL-3, IL4, IL-7 in trace amounts.

It will be apparent from the disclosure detailed herein that the cytokine compositions of the invention and the methods that utilize them are applicable to the stimulation of an immune response to any antigen of interest, e.g., cancer or tumor antigens, as well as antigens produced by other persistent disease states or lesions. As detailed herein, the cytokine mixture of the invention acts as an adjuvant preferably to stimulate T cell immunity in vivo.

Moreover, the present invention relates to, but not exclusively to, eliciting an immune response to either endogenous antigens, i.e., proteins or peptides that are located in vivo and are processed and presented by APCs (such as dendritic cells) in vivo, or to exogenous antigens, i.e., proteins or peptides that have been isolated or generated in vitro and then administered in vivo to an environment (e.g., a lymph node) where dendritic cells are present and can effectively present the antigens, e.g., to T cells. In particular as it relates to peptide antigens, this goal is considered by many immunologists to be insurmountable. Peptides are generally considered to be much too small to be effective immunogens, their half life is short, and they are often non-mutated self antigens to which the patient is immunologically tolerant. Thus, gaining an immune response to such antigens is tantamount to inducing auto-immunity.

As described herein, the present invention is useful to develop a consistent and effective method of vaccine immunotherapy, wherein immune responses are elicited in patients, such as cancer patients, using the cytokine compositions of the present invention in combination with endogenous and/or exogenous disease-associated antigens, including tumor antigens and peptides.

SUMMARY OF THE INVENTION

The present invention relates to compositions and methods of immunotherapy to treat cancer or other antigen-producing diseases or lesions. According to one embodiment of the invention, a composition is provided for eliciting an immune response to at least one antigen in a patient having an antigen-producing disease or lesion, the composition comprising an effective amount of a cytokine mixture, preferably comprising the cytokines IL-1, IL-2, IL-6, IL-8, IFN-γ (gamma) and TNF-α (alpha). According to a preferred embodiment, the cytokine mixture is the natural cytokine mixture, NCM, as disclosed in U.S. Pat. Nos. 5,632,983 and 5,698,194. The cytokine mixture acts as an adjuvant with the antigen associated with the antigen-producing disease or lesion to enhance the immune response of the patient to the antigen.

The cytokine mixture of the invention comprising IL-1, IL-2, IL-6, IL-8, IFN-γ and TNF-α can include natural, recombinant or pegylated cytokines or a mixture of natural, recombinant or pegylated cytokines. According to another embodiment of the invention, the cytokine mixture can further include other natural, recombinant or pegylated cytokines such as IL-12, GM-CSF, and G-CSF.

The present invention also relates to methods of eliciting an immune response to at least one antigen in a patient having an antigen-producing disease or lesion comprising administering an effective amount of a cytokine mixture comprising IL-1, IL-2, IL-6, IL-8, IFN-γ, and TNF-α, wherein the cytokines act as an adjuvant with the antigen and stimulate an immune response to the antigen in the patient.

Moreover, according to the present invention, the antigen can be an endogenous and/or exogenous antigen. In the embodiment of the invention wherein the antigen is an endogenous antigen, i.e., present in vivo, the cytokine mixture is administered to the patient, and the cytokines act as an adjuvant with the endogenous antigen to stimulate an immune response in the patient. In the embodiment wherein the antigen is an exogenous antigen, i.e., isolated or generated in vitro and administered to the patient in vivo, the cytokine mixture is administered in combination with the exogenous antigen (either in the same preparation or in a separate preparation either at the same time or at a different time). The cytokine mixture acts as an adjuvant with the exogenous antigen to stimulate an immune response to the antigen.

According to preferred embodiments of the compositions and methods of the invention, the antigen is a tumor antigen and the antigen-producing disease is cancer, such as squamous cell carcinoma of the head and neck (H&N SCC), prostate cancer, melanoma, breast cancer, lymphoma, cervical cancer or hepatoma. Alternatively, the antigen can be one associated with infectious diseases, such as hepatitis, tuberculosis or HIV, or with persistent lesions such as cutaneous or systemic candidiasis, papilloma virus-associated venereal warts or cervical dysplasia.

BRIEF DESCRIPTION OF THE DRAWINGS

Other advantages of the present invention are readily appreciated as the same becomes better understood by reference to the following detailed description when considered in connection with the accompanying drawings wherein:

FIG. 19A contains two bar graphs depicting the increase in percentage of monocytes/macrophages staining positive for the combination of activation markers, CD86, HLA-DR, CD80 and CD40, after treatment of adherent PBMCs with NCM, as determined by flow cytometry.

FIG. 29A depicts the serum antibody response to the OVA carrier in mice immunized with the OVA-PSMA conjugate and NCM (IRX), alum or CpG. Data are presented as mean and standard error of the mean for 5-10 mice per group. FIG. 29B depicts the serum antibody response to the PSMA peptides in mice immunized with the OVA-PSMA conjugate and NCM (IRX), alum or CpG. FIG. 29C depicts the serum antibody response to the PSMA peptides in mice immunized with the KLH-PSMA conjugate in combination with NCM (IRX), alum or PBS. The results were determined by ELISA assay and are presented as optical density.

FIG. 30 depicts the stabilization of PSA levels over a 6 month period in three prostate cancer patients treated with the NCM of the invention in combination with PSMA peptide antigens.

DETAILED DESCRIPTION OF THE INVENTION

Figure 1:
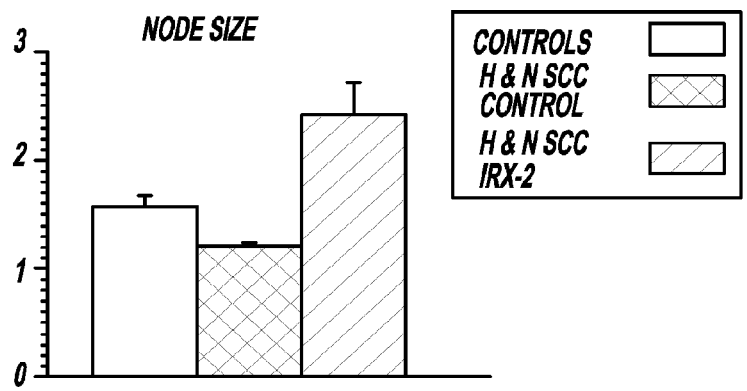
FIG. 1 is a bar graph showing lymph node size in normal controls, cancer controls or NCM-treated populations with H&NSCC.
Figure 2A:
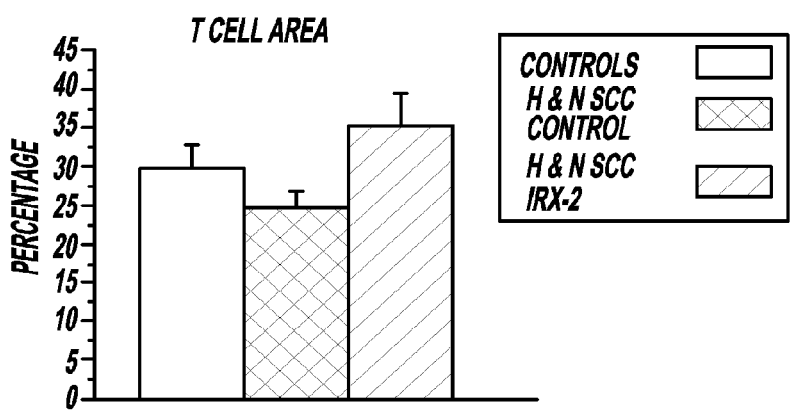
FIG. 2A is a bar graph showing T cell area and FIG. 2B shows density in normal controls, H&NSCC controls and H&NSCC patients treated with NCM.
Figure 2B:
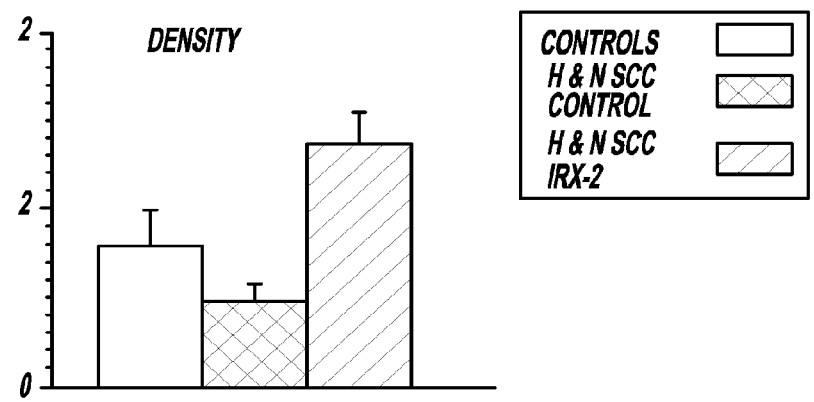
Figure 3A:
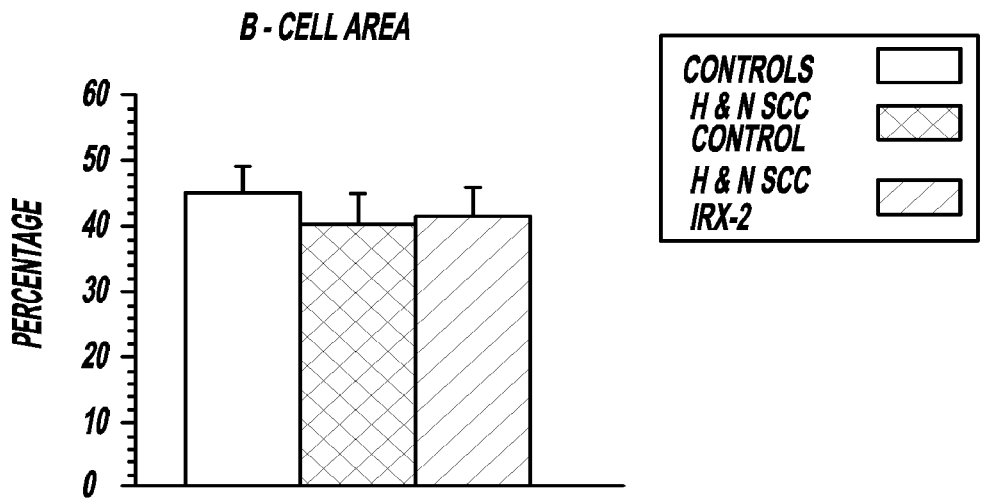
FIG. 3A is a bar graph comparing B cell area and FIG. 3B is a bar graph comparing follicles in the three treatment groups.
Figure 3B:
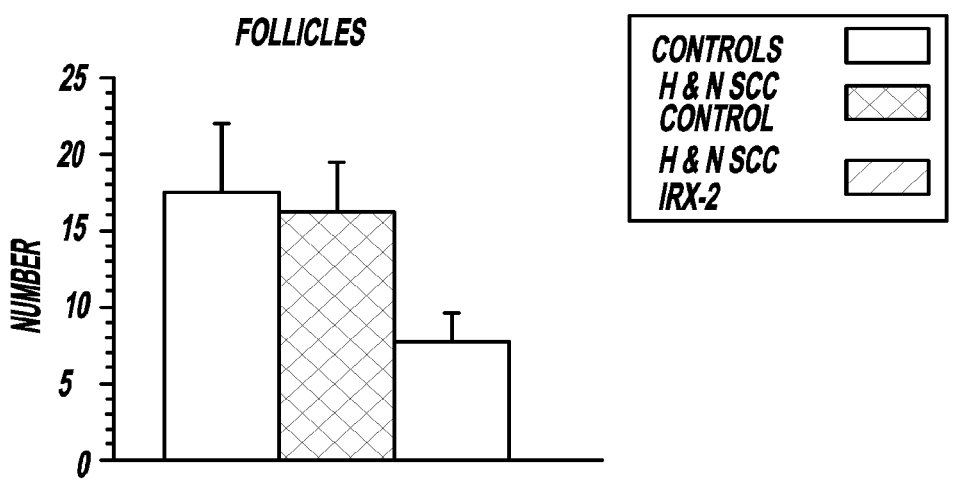
Figure 4A:
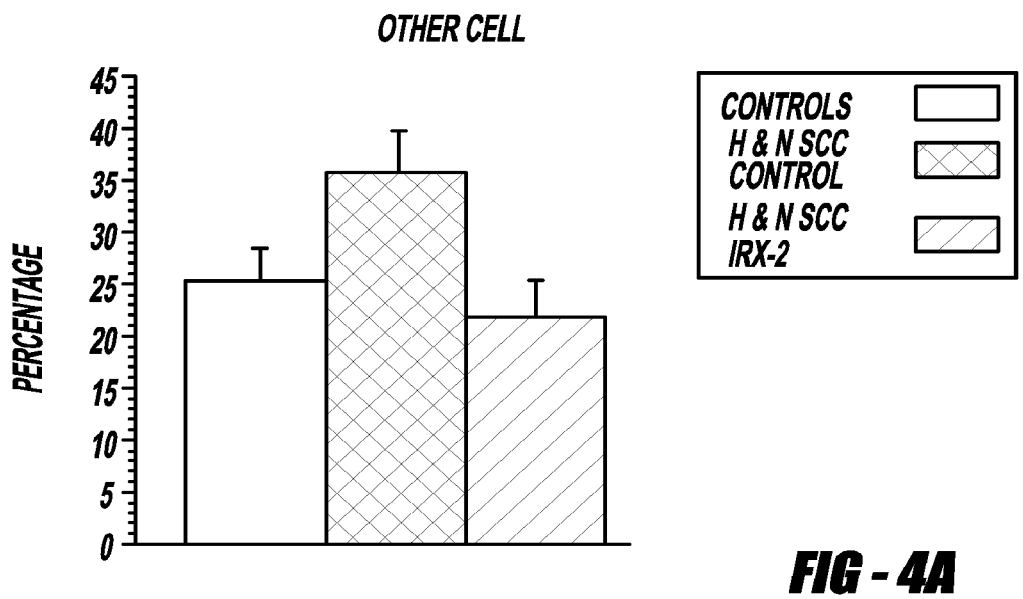
FIG. 4A shows a comparison of other cells and FIG. 4B shows a comparison of sinus histiocytosis (SH) in the three treatment groups.
Figure 4B:
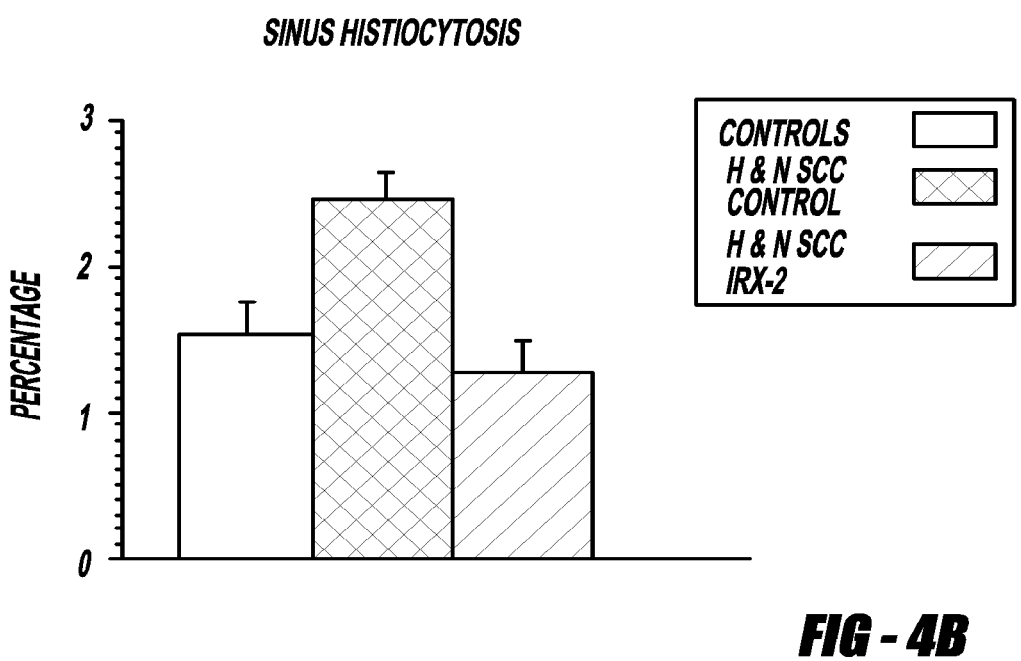

The present invention relates to compositions and methods of immunotherapy to treat cancer or other antigen-producing persistent lesions or disease states. More specifically, the invention relates to compositions and methods for eliciting an immune response to an antigen associated with a cancer or other antigen-producing disease or lesion, wherein a cytokine mixture comprising IL-1, IL-2, IL-6, IL-8, IFN-γ, and TNF-α is administered to a patient in an amount effective to stimulate an immune response to the antigen in the patient. According to the present invention, the antigen can be an endogenous and/or exogenous antigen and the cytokine mixture acts as an adjuvant with the antigen to stimulate an immune response to the antigen in a patient.

As used herein, the term "adjuvant" denotes a composition with the ability to enhance the immune response to a particular antigen. Such ability is manifested by a significant increase in immune-mediated protection. To be effective, an adjuvant must be delivered at or near the site of antigen. Enhancement of immunity is typically manifested by either a significant increase (usually greater than 10 fold) in the titer of antibody raised to the antigen and/or enhancement of cellular immunity, which can be measured by a positive skin test, cytotoxic T cell assay, ELISPOT assay for IFN-γ or IL-2, or T cell infiltration into the tumor. The cytokine compositions of the present invention are particularly suited to enhance T cell-mediated immune responses. The adjuvant effects of the cytokine compositions of the invention include the generation of naive T cells, the promotion of dendritic cell differentiation and maturation, the stimulation of monocytes and macrophages, and in the case of cancer patients, increased lymphocyte infiltration into tumors, tumor fragmentation, tumor regression, and reduction of sinus histiocytosis in the lymph nodes.

As used herein, the term "tumor associated antigen" denotes a protein or peptide or other molecule capable of inducing an immune response to a tumor. This can include, but is not limited to, PSMA peptides, MAGE peptides (Sahin, 1997; Wang, 1999), Papilloma virus peptides (E6 and E7), MAGE fragments, NY ESO-1 or other similar antigens. Previously, these antigens were not considered to be effective in treating patients based either on their size, i.e., they were considered too small, or they were previously thought to lack immunogenic properties (i.e., they were considered to be self antigens).

As used herein, "NCM" denotes a natural cytokine mixture as defined and set forth in U.S. Pat. Nos. 5,632,983 and 5,698,194. Briefly, NCM is prepared in the continuous presence of a 4-aminoquinolone antibiotic and with the continuous or pulsed presence of a mitogen, which in the preferred embodiment is PHA. In addition to naturally-occurring cytokines, the NCM can include recombinant and/or pegylated cytokines, the production of which is well known in the art (see, e.g., U.S. Pat. Nos. 4,738,927, 4,992,367, United States Patent Application Publication No. US 2004/0136952 A1 and Mehvar, 2000).

As used herein, the term "endogenous antigen" denotes an antigen that is produced and situated in vivo, i.e., within an organism such as a patient, such that, after the administration of the cytokine composition of the invention in vivo, the cytokines act as an adjuvant with the antigen within the patient to stimulate an immune response to the antigen.

As used herein, the term "exogenous antigen" denotes an antigen that is produced, i.e., isolated or generated, in vitro, i.e., outside of an organism to be treated, and is administered to the organism (i.e., a patient) in vivo, such that, after the administration of the cytokine composition of the invention in vivo, the cytokines act as an adjuvant with the antigen within the patient to stimulate an immune response to the antigen. The exogenous antigen can be a chemically synthesized or genetically engineered compound or molecule or can be an endogenous antigen that has been extracted from its in vivo environment and isolated in vitro. The extracted antigen can be processed or otherwise modified for re-introduction in vivo. The exogenous antigen can be administered either in a separate pharmacological preparation from the cytokine composition of the invention or in the same preparation.

As defined above, the cytokine mixture of the invention acts as an adjuvant, i.e., stimulates or enhances the immune response of a patient to a particular antigen. Moreover, the cytokine compositions and methods of the invention are particularly suited to stimulate T cell-mediated immune responses. Immune responses promoted by the compositions and methods of the invention include the induction or generation of naive T cells, the differentiation and maturation of dendritic cells, allowing for proper presentation of antigen to T cells (e.g., in the lymph nodes), and the activation of monocytes and macrophages. Specifically, in cancer patients, immune responses promoted by the compositions and methods of the invention include tumor infiltration by lymphocytes, tumor fragmentation and regression as well as a reduction in sinus histiocytosis (when present).

More specifically, the compositions and methods of the present invention aid in overcoming immune depression/suppression in patients by inducing the production of naive T cells. The term "naive" T cells, as defined herein, denotes newly produced T cells, which T cells have not yet been exposed to antigen. Such T cells are non-specific, yet are capable of becoming specific upon presentation of antigen by a mature dendritic cell having antigen, such as tumor peptides, exposed thereon. Thus, the compositions and methods of the invention replenish or generate new T cells (see Examples 2 and 8 below).

In addition, particularly in cancer patients having tumors, the present compositions and methods allow for lymphocyte infiltration into the tumors with significant tumor fragmentation and regression. See, e.g., Examples 2-7 below. Such infiltration is important in order to maximize clinical response and for the greatest increase in survival rate. For example, lymphocyte:granulocyte or macrophage infiltration of a 90:10 ratio is optimal and T and/or B cell infiltration is preferably diffuse and intense and not peripheral. Tumor reduction and fragmentation in histological samples reflects a good immune response and is indicative of an adjuvant effect by the compositions of the invention.

Moreover, specific lymph node changes also indicate an effective immune response, such as lymph node enlargement, i.e., not just reversal of tumor-induced reduction of size but overall increase in size compared to the normal node size, as well as increased T and B cell areas. In addition, the lymph nodes of cancer patients often contain an intrasinusoidal accumulation of large histiocytes, also termed sinus histiocytosis (SH). SH is believed to be the accumulation of immature dendritic cells, which have ingested and processed tumor antigens but are unable to mature and present these tumor peptides to naive T cells. Without the proper presentation of antigen to T cells, these T cells are incapable of stimulating Th1 and Th2 effector cells, which stimulation normally leads to cell-mediated and antibody-mediated immunity, respectively, in the body. As indicated in Examples 2-7 below, the cytokine compositions and methods of this invention reduced SH in the lymph nodes of cancer patients and produced the various lymph changes described above, again indicating an adjuvant effect by the compositions of the invention.

Because dendritic cells are known to play such a key role in antigen presentation in the production of an appropriate immune response in vivo, an agent having a stimulatory effect on dendritic cell maturation will act as an adjuvant in eliciting a good immune response to an antigen. As demonstrated in Example 9 below, the cytokine compositions of the present invention promote dendritic cell maturation. Furthermore, the data of Example 2 demonstrate that the cytokine compositions of the invention also unblock the dendritic cell defect that leads to SH, i.e., by promoting DC maturation, and thus specifically, in cancer patients, the compositions of the invention provide multiple adjuvant effects, i.e., in unblocking DCs in SH in the lymph nodes and in promoting DC maturation generally.

The cytokine compositions of the invention also provide a further adjuvant effect by acting as potent activators of monocytes/macrophages. Monocytes are precursors to both DCs and macrophages in the body and thus an agent that promotes monocyte/macrophage activation has an adjuvant effect on immune responses in vivo. See Example 10 below.

In view of the above, the compositions and methods of the present invention stimulate the immune system via multiple effects, including the in vivo maturation of dendritic cells resulting in effective peptide antigen presentation as well as activation of monocytes and macrophages and the production of naive uncommitted T cells. The proper presentation of antigen leads to T and B cell clonal expansion, creating immunity in the patient. In the case of cancer patients, the effects noted above result in the infiltration, e.g., of lymphocytes, into tumors (e.g., via hematogenous spread) and tumor reduction and/or destruction. The result, as indicated by the data below, is increased survival due to immunologic memory (see, e.g., Example 3 below).

More specifically then, the present invention provides compositions comprising a cytokine mixture comprising the cytokines IL-1, IL-2, IL-6, IL-8, IFN-γ, and TNF-α. According to a preferred embodiment, the cytokine mixture contains a concentration of IL-1 that ranges from 60-6,000 pcg/ml, more preferably, from 150-1,200 pcg/ml; a concentration of IL-2 that ranges from 600-60,000 pcg/ml, more preferably, from 1,000-12,000 pcg/ml; and more preferably, from 4,000-8,000 pcg/ml; a concentration of IL-6 that ranges from 60-6,000 pcg/ml, more preferably, from 300-2,000 pcg/ml; a concentration of IL-8 that ranges from 6,000-600,000 pcg/ml, more preferably, from 20,000-180,000 pcg/ml; and concentrations of IFN-γ and TNF-α, respectively, that range from 200-20,000 pcg/ml, more preferably, from 1,000-4,000 pcg/ml.

According to another embodiment of the invention, the cytokine mixture further includes the cytokines IL-12, GM-CSF, and/or G-CSF. According to yet another embodiment, the cytokines of the cytokine mixture can be natural, recombinant, pegylated or mixtures of natural, recombinant or pegylated cytokines. Cytokines may be pegylated in order to increase the half-life of the cytokine in vivo and/or to reduce the immunogenicity or toxicity of the cytokine protein in vivo (see, e.g., United States Patent Application Publication US 2004/0136952 A1). Methods for pegylating proteins, including cytokines, are well known in the art (see, e.g., Mehvar, 2000) and a number of pegylated cytokines have been approved by the FDA for use in treating patients (e.g., IFN-α and G-CSF).

Also encompassed by the present invention are derivatives, fragments and peptides related to the cytokines disclosed herein, wherein such derivatives, fragments and peptides retain the biological activity of their respective cytokines. According to a preferred embodiment, the cytokine mixture is the natural cytokine mixture, NCM, as disclosed in U.S. Pat. Nos. 5,632,983 and 5,698,194.

The cytokine mixture of the invention acts as an adjuvant with a disease- or lesion-associated antigen to stimulate an immune response to the antigen in a patient. Moreover, the antigen can be either an endogenous antigen or peptide (e.g., in the case of cancer, the antigen or peptide may be present in regional lymph nodes or at the tumor site) or an exogenous antigen or peptide preparation, i.e., isolated or generated in vitro and then administered to the patient in combination with the cytokine mixture of the invention at a site in vivo (e.g., in the case of cancer, in or near a lymph node regional to a tumor).

According to the embodiment of the invention wherein the antigen is endogenous, the compositions and methods of the invention comprise the cytokine mixture of the invention without the addition of any external antigen. According to the embodiment of the invention wherein the antigen is exogenous, the compositions and methods of the invention comprise the cytokine mixture of the invention in combination with an exogenous antigen. According to the latter embodiment, the cytokine mixture and exogenous antigen can be administered at the same time, either in a single pharmacological preparation or in separate preparations, or they can be administered in separate preparations at different times.

According to a preferred embodiment, the endogenous or exogenous antigen is a tumor antigen and the tumor antigen may be a full-length antigen or immunogenic peptides or fragments of the tumor antigen. Moreover, because the present invention is directed towards affecting antigen processing generally, it is therefore useful to stimulate an immune response to any antigen. Moreover, the present invention is applicable to all forms of antigens and haptens including peptides, lipids and/or carbohydrates.

The present invention also provides methods of eliciting an immune response to at least one endogenous or exogenous antigen in a patient having an antigen-producing disease or lesion. More specifically, the methods of the invention comprise the step of administering an effective amount of a cytokine mixture comprising IL-1, IL-2, IL-6, IL-8, IFN-γ, and TNF-α, wherein the cytokine mixture acts as an adjuvant with the antigen and stimulates an immune response to the antigen in the patient. According to one embodiment, the antigen-producing disease from which the patient is suffering is cancer. Such cancers can include H&N SCC, prostate cancer, melanoma, breast cancer, lymphoma, cervical cancer or hepatoma.

Alternatively, the antigen-producing disease can include any infectious disease that produces an antigen in vivo, e.g., hepatitis, tuberculosis or HIV. Thus, the present invention can extend to areas of applicability such as the use of the cytokine compositions and methods of the invention in combination with AIDS virus vaccine therapy in HIV+ patients or other situations where adjuvant therapy is appropriate, i.e., to boost the immune system such as renal transplants, in aged individuals, and the like.

In addition, the compositions and methods of the invention can be used to treat non-cancerous persistent lesions such as infectious lesions that produce an antigen in vivo, e.g., cutaneous or systemic candidiasis, papilloma virus-associated venereal warts or cervical dysplasia.

According to one embodiment of the method of the invention, at least one exogenous antigen is administered to the patient in combination with the cytokine mixture, wherein the cytokine mixture acts with the exogenous antigen to stimulate an immune response in the patient. According to this embodiment, the method of the invention comprises administering an effective amount of the cytokine mixture comprising IL-1, IL-2, IL-6, IL-8, IFN-γ, and TNF-α in combination with an effective amount of at least one exogenous antigen. According to a preferred embodiment, the antigen is a tumor antigen. The exogenous antigen can be administered in the same pharmacological preparation as the cytokine mixture and therefore simultaneously with the cytokine mixture or the antigen can be administered in a separate pharmacological preparation, either at the same time as the cytokine mixture is administered or at a time prior to or after administration of the cytokine mixture. As demonstrated by the data of Example 11 below, the NCM composition of the invention is effective in combination with exogenous prostate-specific membrane antigens (PSMA) in promoting immune responses in both mice and humans.

An alternative embodiment of the method of the invention encompasses administrating the cytokine composition of the invention to a patient, wherein the antigen to which the cytokines act as adjuvants is one or more endogenous antigens, i.e., already located in vivo; therefore it is not necessary to administer any external antigen to the patient. According to this embodiment then, there is no need for the administration of an exogenous antigen preparation but only the cytokine composition of the invention is administered to the patient.

The present invention also encompasses the use of both an endogenous antigen and an exogenous antigen, i.e., wherein the cytokine composition of the invention is administered in combination with an exogenous antigen to a patient having an endogenous antigen in vivo and wherein the cytokines act as an adjuvant with both antigens to stimulate immune responses in the patient.

The methods of the invention also include methods of immunotherapy to treat cancer, such as H&N SCC, prostate cancer, melanoma, breast cancer, lymphoma, cervical cancer and hepatoma, wherein the cytokine mixture of the invention is administered to a patient to stimulate an immune response. As noted, the cytokine mixture acts as an adjuvant with tumor antigens (either endogenous and/or exogenous) to stimulate an immune response to the antigen in the patient.

For any of the above embodiments, the following administration details and/or protocols for treatment are used:

Preferably, the cytokine composition of the present invention is injected around lymphatics that drain into lymph nodes regional to a lesion, such as a tumor or other persistent lesions being treated. More specifically, local perilymphatic injections or other injections that are known to those of skill in the art are administered to provide sufficient localization of the immunotherapy preparation. In the case of head and neck cancer, the injections are given in the neck, but can be applied in other locations as required by the disease to be treated. Such treatment induced clinical regressions in a high percentage of head and neck cancer patients, who also showed improved, recurrence-free survival (Hadden, 1994; Meneses, 1998; Barrera, 2000; Whiteside, 1993). In contrast, intratumoral injection of recombinant interleukin-2 in head and neck cancer patients (Whiteside, et al (Cancer Res. 53:5654-5662, 1993)) produced a T cell lymphocyte infiltrate, but no significant clinical responses. Similarly, peritumoral injection of Multikine (Celsci Website) in combination with perilymphatic injection resulted in significant tumor responses (i.e., greater than 50% tumor reduction) in only 11 patients, making their response rate less than 10%. Furthermore, peritumoral and intratumoral injection can be associated with progression of disease, even in patients who initially have had a positive response to the cytokine protocol, thus undoing its benefit. Peritumoral or intratumoral injection is thus contraindicated.

A ten (10) day injection scheme for administration of the compositions of the invention is preferred, but a twenty (20) day injection protocol can be used. Bilateral injections are effective. Where radical neck dissection has occurred, contralateral injection is effective.

In the embodiment wherein an exogenous antigen is to be utilized, exogenously provided synthetic or extracted antigens such as tumor antigen and peptides (see Bellone, 1998) can be administered into the pre-primed or co-primed regional or distal lymph node, either in a separate preparation or as part of the cytokine composition of the invention.

According to one embodiment of the invention, endogenous suppression of T cells, which can be caused by, e.g., cancer or other immunosuppressive diseases, may be blocked by the co-administration of low dose cyclophosphamide (CY) and a non-steroidal anti-inflammatory drug (NSAID) (i.e., in combination with the cytokine compositions of the invention). The NSAID is preferably indomethacin (INDO) but ibuprofen or Coxil inhibitors such as celecoxib (Celebrex®) or rofecoxib (Vioxx®) or combinations thereof can also be used. Side effects of NSAIDS can be aggressively treated with proton inhibitors and prostaglandin E analogs Zinc and multi-vitamins, possibly including the addition of selenium, can also be added as agents to help restore T cell immunity. Preferably, the dose of zinc is 15 to 75 mg. A standard multivitamin can be administered. The zinc can be an available gluconate.

The cytokine compositions of the invention can be administered prior to or after surgery, radiotherapy, chemotherapy, or combinations thereof. The compositions of the invention can be administered during the recurrence of tumors, i.e., during a period where tumor growth is occurring again after a period where tumors were thought to have disappeared or were in remission.

The cytokine compositions of the present invention are administered and dosed to promote optimal immunization either to exogenous or endogenous antigen, taking into account the clinical condition of the individual patient, the site and method of administration, scheduling of administration, patient age, sex, and body weight. The pharmaceutically "effective amount" for purposes herein is thus determined by such considerations as are known in the art. The amount must be effective to promote immunization, leading to, e.g., tumor reduction, tumor fragmentation and leukocyte infiltration, delayed recurrence or improved survival rate, or improvement or elimination of symptoms, including increased T cell counts.

In the methods of the present invention, the compositions of the present invention can be administered in various ways. It should be noted that the cytokines or exogenous antigens used in the compositions of the invention can be administered in their standard forms or as pharmaceutically acceptable derivatives and can be administered alone or as active ingredients in combination with pharmaceutically acceptable carriers, diluents, adjuvants and vehicles. Furthermore, the compositions of the invention can be administered intra- or subcutaneously, or peri- or intralymphatically, intranodally or intrasplenically or intramuscularly, intraperitoneally, and intrathorasically. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. When administering the compositions of the present invention, they are generally formulated in a unit dosage injectable form (e.g., solution, suspension, or emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, or vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for the compositions of the invention. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent or additive used would have to be compatible with the cytokines or exogenous antigens of the invention.

Sterile injectable solutions can be prepared by incorporating the cytokines or exogenous antigens utilized in practicing the present invention in the required amount of the appropriate solvent with several of the other ingredients, as desired.

A pharmacological formulation of the present invention can be administered to the patient in an injectable formulation containing any compatible carrier, such as various vehicles, additives, and diluents; or the cytokines and/or exogenous antigens utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

It should be apparent that the compositions and methods of the invention are useful for the treatment of antigen-producing diseases such as cancer, infectious diseases or persistent lesions, as discussed above. The compositions and methods promote immunization against the antigens produced by these diseases by stimulating immune responses in patients in vivo, which immune responses help to alleviate or eliminate the symptoms and effects of the disease in the patient.

The above discussion provides a factual basis for the use of the present invention. The compositions and methods of the invention for use in the utilities disclosed herein can be shown by the following non-limiting examples and accompanying Figures.

The examples set forth below describe the preparation of NCM, a cytokine mixture in accordance with this invention, data from clinical trials demonstrating the use of NCM as an adjuvant with endogenous tumor antigens to stimulate immune responses in cancer patients as well as experiments in mice and humans demonstrating the use of the cytokine mixture of the invention with exogenous antigens to stimulate immune responses in vivo.

More specifically, Example 1 below describes the production of NCM, a cytokine composition in accordance with the present invention. The production of NCM is fully disclosed in U.S. Pat. Nos. 5,632,983 and 5,698,194, which are incorporated herein by reference.

Example 2 below discloses clinical trial data wherein H&N SCC patients treated with NCM (in combination with low dose cyclophosphamide (CY), indomethacin (INDO) and zinc) displayed significant clinical and pathological responses including nodal changes indicating immunization (e.g., increases in node size and decreases in sinus histiocytosis), tumor infiltration with lymphocytes, and tumor reduction and fragmentation. Examples 4-7 relate to additional cancer patients, i.e., with lymphoma, cervical cancer, liver cancer, and squamous cell carcinoma of the penis (human papilloma-virus associated), all of whom were treated with the NCM of the invention and who showed significant clinical responses to the treatment. Example 3 provides data regarding the increased survival (up to 2 years) of the cancer patients of these studies.

As demonstrated in Example 2, treatment with NCM also produced marked increases in T lymphocyte counts in T lymphocytopenic patients and a corresponding increase in naive T cells (newly-produced T cells unexposed to antigen). Furthermore, as indicated by the data of Example 8 below, the increases in T cells observed in these studies was specifically due to treatment with the cytokine composition of the invention. More specifically, Example 8 provides data of the treatment of lymphocytopenic, H&N SCC cancer patients with only NCM (without the accompanying administration of CY and/or INDO), wherein significant increases in overall lymphocyte counts as well as specific CD3+ and CD4+ T cell subset populations were obtained.

Similarly, the data of Example 9 demonstrate that NCM promotes the differentiation and maturation of dendritic cells as measured by morphologic, phenotypic and functional criteria. As noted above, dendritic cells (DCs) are known to play a critical role in the immunization of patients to antigens, i.e., by presenting antigen to the appropriate T cell. More specifically, Example 9 demonstrates that NCM promotes morphologic changes in DCs indicative of maturation. NCM also was shown to down-regulate CD1a antigen expression on the DC cell surface, to upregulate CD83 and MHC II antigen expression on the DC cell surface, and to increase the expression of T cell co-stimulatory and adhesion molecules, e.g., CD86, CD40, and CD54 (ICAM-1), on the DC cell surface. In addition, NCM was shown to down-regulate the endocytic activity of DCs (which is consistent with maturation of the DCs), to enhance the T cell stimulatory activity of DCs (as demonstrated by increased MLR activity) and to increase the production of IL-12 from DCs, IL-12 itself being an essential factor in the differentiation of naive CD4+ helper T cells (into Th1 cells) and the activation and proliferation of cellular and phagocytic components of the immune system. Finally, NCM was shown to reduce VEGF-induced apoptosis of DCs. This anti-apoptotic effect of NCM may play a crucial role in maintaining the survival of mature DCs within a tumor setting, allowing for prolonged antigen presentation and activation of tumor antigen-specific cytotoxic T lymphocytes.

The data of Example 10 below demonstrate further that NCM is a potent activator of monocytes and macrophages. For example, NCM significantly increases activation markers of monocytes/macrophages, i.e., HLA-DR, CD86, CD40 and CD80. In addition, the NCM was shown to be a stronger activator of monocytes/macrophages than TNF-α or LPS and the NCM was able to continue activating the cells even in the presence of the immunosuppressing cytokine IL-10.

Example 11 below demonstrates the ability of NCM to elicit immune responses, i.e., in the form of DTH responses as well as antibody responses, in mice following administration of the cytokine composition in combination with exogenous prostate-specific membrane (PSMA) peptide antigen conjugates. The NCM was also effective in stimulating DTH responses to unconjugated PSMA peptides in humans with advanced prostate cancer.

EXAMPLES

All steps relating to cell culture are performed under sterile conditions. General methods of cellular immunology not described herein are performed as described in general references for cellular immunology techniques such as Mishell and Shiigi (Selected Methods in Cellular Immunology, 1981) and are well known to those of skill in the art.

Example 1

Preparation of Natural Cytokine Mixture (NCM)

NCM (also referred to herein as IRX-2) is a defined mixture of cytokines produced under GMP conditions over a 24 hour period following stimulation of human peripheral blood mononuclear cells (PBMCS) by phytohemagglutinin (PHA) and ciprofloxacin. The source of the PBMCs is screened and tested buffy coats purchased from FDA licensed blood banks. After PHA stimulation, the mitogen is removed through centrifugation and washing. All cellular elements are removed by centrifugation, and DNA is removed by anion exchange chromatography. The cell-free supernatant is filter sterilized and nanofiltered to permit viral removal and is designated IRX-2. Stringent QC testing that includes both bioassay and ELISA determination of cytokine levels assures the consistency of the IRX-2. Safety testing with respect to sterility, DNA, mycoplasma, endotoxin and virus testing for CMV and EBV are also part of the GMP process. IRX-2 has been given safely to over 150 patients in various clinical trials and is currently in Phase I/II testing under an FDA approved IND.

More specifically, the NCM can be prepared as follows:

The buffy coat white cells of human blood from multiple HIV-negative hepatitis virus-negative donors are collected. In an alternative embodiment, animals could be the cell source for veterinary uses. The cells from the donors are pooled and layered on ficoll hypaque gradients (Pharmacia) to yield lymphocytes free of neutrophils and erythrocytes. Alternative methods could be used that would result in the same starting lymphocyte population as are known in the art.

The lymphocytes are washed and distributed in X-VIVO 10 media (Whittaker Bioproducts) in surface-activated cell culture flasks for selection of cell subsets. The flasks (MICROCELLECTOR™ T-25 Cell Culture Flasks) contain immobilized stimulants, i.e., mitogens, such as PHA. The immobilization process for the stimulants is as described by the manufacturer for immobilizing various substances for panning procedures, i.e., separating cells, in the flasks. Alternatively, the lymphocytes are exposed to stimulants, e.g., PHA, for 2-4 hours and then washed three times.

The cells are incubated for 24-48 hours in X VIVO-10 media with 80 µg/ml ciprofloxacin (Miles Lab) at 37° C. in a $CO_2$/air incubator. Alternatively, RPMI 1640 media could be used (Webb et al. 1973). HSA (human serum albumin) may be added to stabilize further the interleukins if HSA-free media is used for generations. Generally, HSA is used at 0.1 to 0.5% (weight by volume). Following incubation, the supernatants are poured off and collected. The supernatants are stored at 4° C. to −70° C.

Example 2

Local perilymphatic injections in the neck with NCM in addition to treatment with low dose CY (at 300 mg/m$^2$), INDO (25 mg orally three times daily), and zinc (65 mg elemental zinc as the sulfate orally once a day) have induced clinical regressions in a high percentage of patients with squamous cell head and neck cancer (H&NSCC) (Hadden, 1994; Meneses, 1998; Barrera, 2000; Hadden, 2003; Menesis, 2003) with evidence of improved, recurrence free survival. Overall, including minor responses (25%-50%), tumor shrinkage and reduction of tumor in pathological specimens, over 90% responded and the majority had greater than 50% tumor reduction.

These responses are speculated to be mediated by immune regression since both B and T lymphocytes were observed infiltrating the tumors. The therapy was not associated with significant toxicity. Treatment of lymphocytopenic cancer patients with the combination of NCM has resulted in marked lymphocyte mobilization; where analyzed, these patients showed increases in CD45RA positive T cells (i.e., naive T cells (see Table I below)). Further, intratumoral or peritumoral injection of NCM in patients with H&NSCC resulted in either reversing immunotherapy-induced tumor regression or in progression of the tumor. The tumor is thus not the site of immunization. Rather, analysis of regional lymph nodes revealed that the regional lymph node is the site of immunization to postulated tumor antigens (Meneses, 2003; see FIGS. 1-5). None of these patients treated with NCM developed metastasis which would have been expected in 15% of the patients clinically and up to 50% pathologically. These results indicate that systemic immunity rather than merely local immunity had been induced. Patients were pretested with a skin test to 0.1 ml of NCM prior to treatment and more than 90% of those with a positive skin test (>0.3 mm at 24 hours) had robust clinical and pathological responses. Patients with negative skin tests had weak or no responses. Thus, skin testing selects good responders.

Major increases were observed in T lymphocyte counts (CD3) 752->1020 in these T lymphocytopenic patients (T cell counts 752 vs. 1600 (normal)). Importantly, there was a corresponding increase in "naive" CD45RA positive T cells (532->782). As previously mentioned, these increases are generally not thought to occur in adults particularly with a pharmacological therapy like NCM. These cells presumably are recent thymic emigres and could be considered a major new capacity for responding to new antigens like tumor antigens. The preexisting CD45RA positive cells were not responding to the tumor antigens and may have been incapable of doing so due to tumor-induced immune suppression (anergy).

TABLE I

Treatment of Lymphocytopenic Patients with H&NSCC with NCM Increases in Naïve T cells in Blood (#/mm)

| PATIENT # | NAÏVE T CELL MARKER | | | PAN T CELL MARKER | | |
|---|---|---|---|---|---|---|
| | PRE | POST | INCREASE | PRE | POST | INCREASE |
| 1 | 479 | 778 | +299 | 704 | 1171 | +467 |
| 2 | 938 | 1309 | +371 | 1364 | 1249 | −115 |
| 3 | 98 | 139 | +41 | 146 | 178 | +32 |
| 4 | 341 | 438 | +97 | 655 | 590 | −65 |
| 5 | 567 | 652 | +97 | 453 | 643 | +190 |
| 6 | 658 | 1058 | +400 | 1118 | 1714 | +569 |
| 7 | 642 | 1101 | +459 | 822 | 1601 | +779 |
| MEAN | 532 | 782 | +250 | 752 | 1020 | +269 |

The literature (Hadden J W, Int'l J Immunopharmacol 11/12:629-644, 1997; Hadden J W, Int'l J Immunopharmacol 21:79-101, 1999) indicates that for both SCC and adenocarcinomas, the two major types of cancer, regional lymph nodes reflect abnormalities related to the tumor, including sinus histiocytosis, lymphoid depletion and often the presence of tumor-associated lymphocytes capable of reacting to tumor cells (with IL-2). With metastasis, lymphoid depletion and depressed function occur. An unpublished analysis of uninvolved cervical lymph nodes in 10H&NSCC patients showed reduction in average lymph node size and an increase in sinus histiocytosis associated with H&NSCC (see controls of FIGS. 1-4A and B of the present application).

Following treatment with one cycle of the NCM protocol (Hadden, 1994; Meneses, 1998; Barrera, 2000), the uninvolved cervical lymph nodes showed the changes indicated in FIGS. 1-4. Compared to the regional lymph nodes of patients with H&NSCC not treated with NCM, these nodes showed a significant increase in size, T cell area and density, and decreases in sinus histiocytosis and congestion. The lymph nodes of treated patients were all stimulated and were larger than control nodes with increased T cell area and density. These nodes were thus not only restored to normal but showed evidence of T cell predominance, a known positive correlate with survival in H&NSCC (Hadden, 1997).

Figure 5:
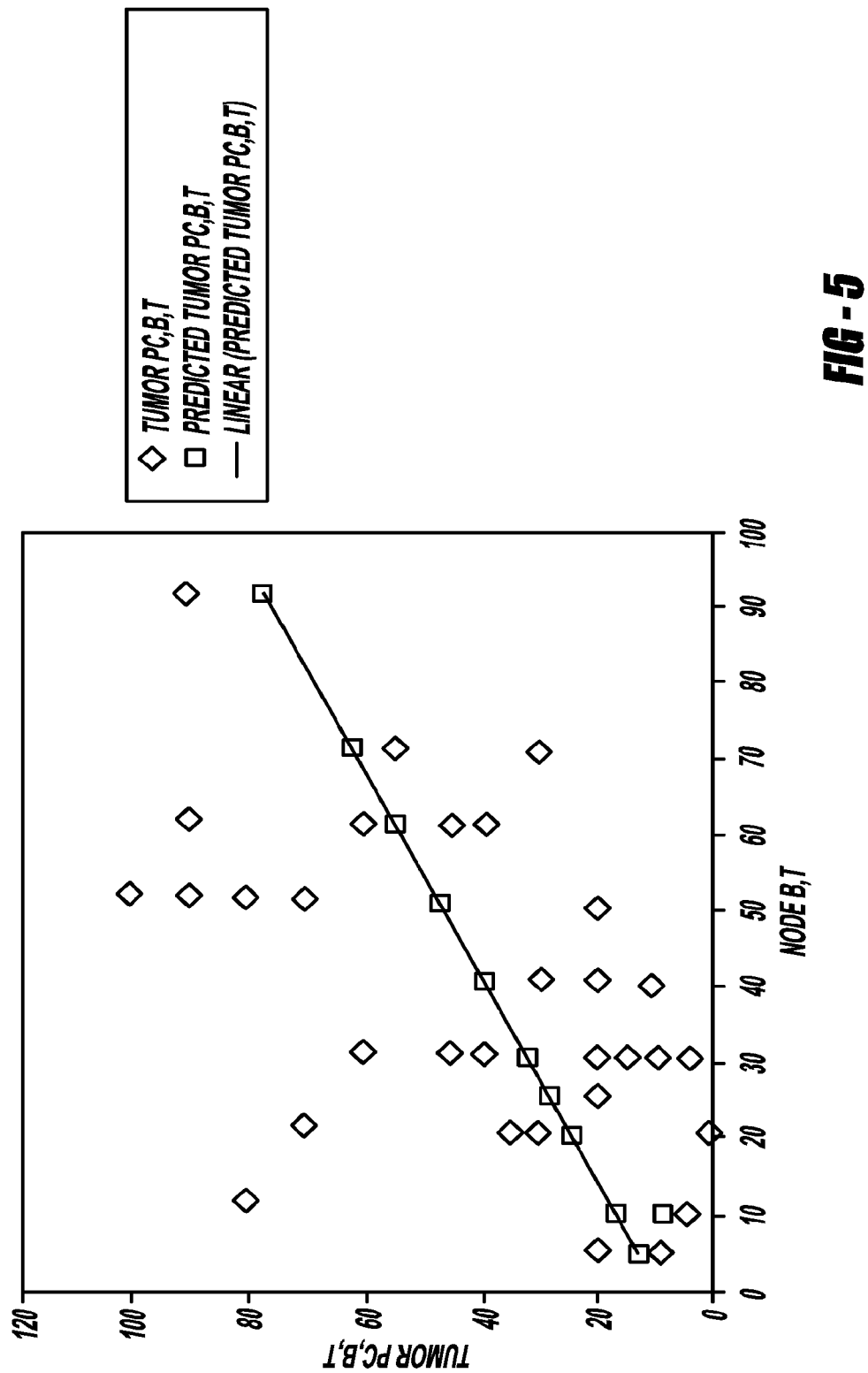
FIG. 5 is a graph showing a Node B&T (B cell and T cell) and Tumor B&T fit plot.

Importantly, when the lymph node changes related to B and T cell areas were correlated with the changes in their tumors reflecting T and B cell infiltration, a high degree of correlation was obtained for T cells (p.<0.01) and B cells (<0.01) and overall lymphoid presence (p.<0.001) (FIG. 5). In turn, these changes correlated with tumor reduction by pathological and clinical criteria. These findings indicate that the tumor reactions are directly and positively correlated with lymph node changes and that the tumor reaction reflects the lymph node changes as the dependent variable. These findings, taken in conjunction with knowledge about how the immune system works in general (Roitt, 1989), and following tumor transfection with a cytokine gene (Maass, 1995), indicate that the NCM protocol immunizes these patients to endogenous tumor antigens at the level of the lymph nodes. No one has previously presented evidence for lymph node changes reflecting immunization with autologous tumor antigens. This confirms that the present invention can induce immunization with previously ineffective or poorly effective tumor antigens in an effect to yield regression of distant metastases.

Example 3

Figure 6:
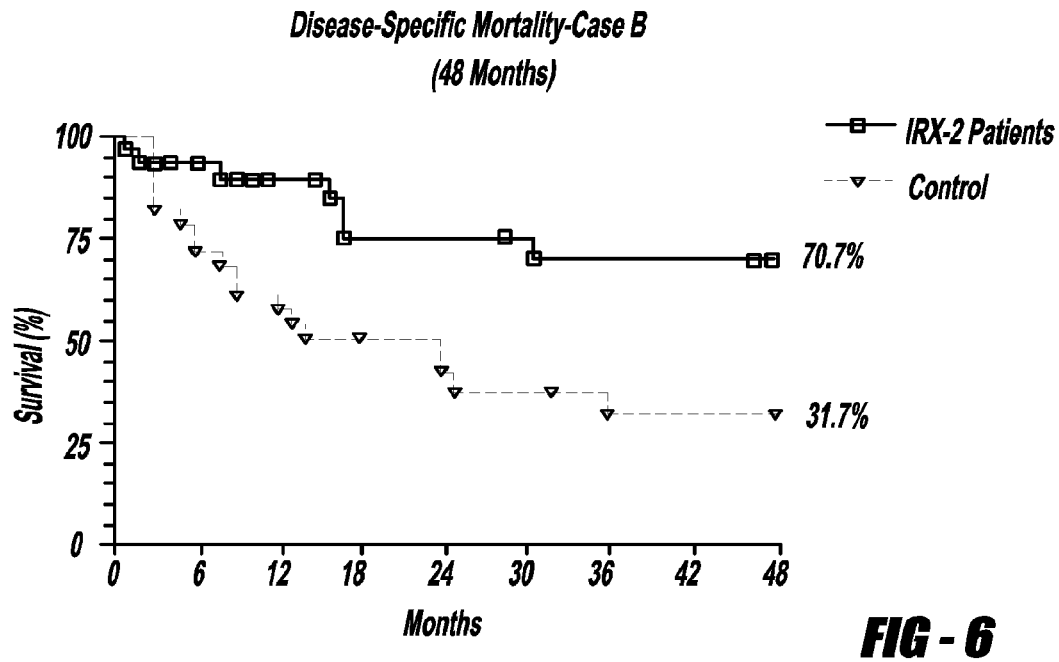
FIG. 6 is a graph illustrating the survival percentage of treated patients at forty-eight months.
Figure 7:
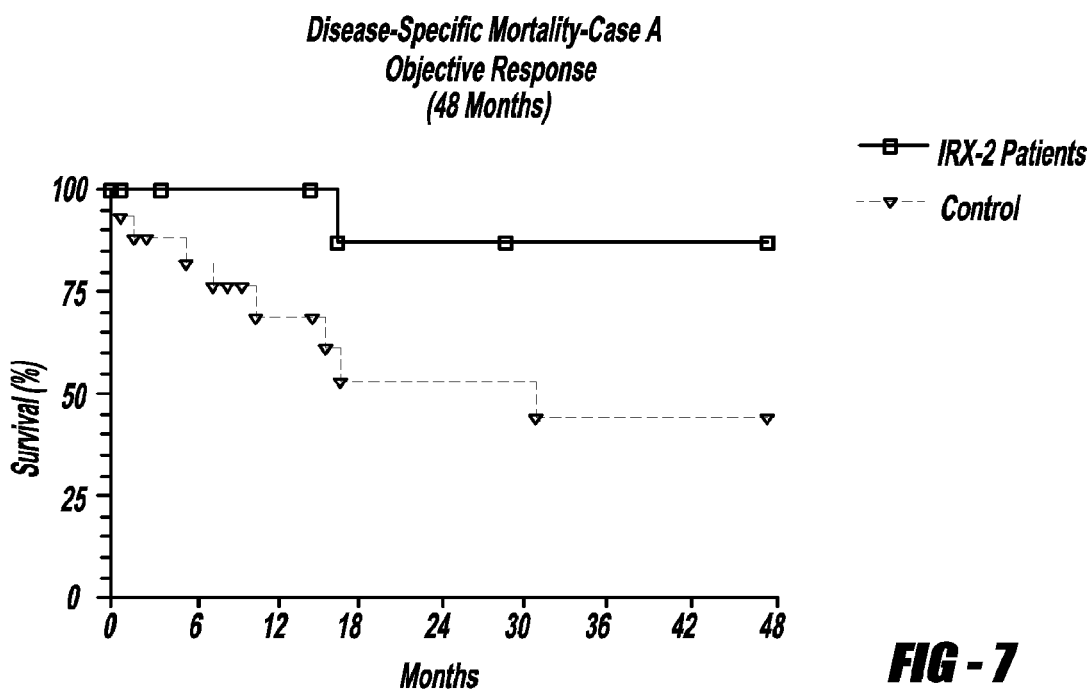
FIG. 7 is a graph illustrating the survival of complete and partial responders compared to minor and non-responders.
Figure 8:
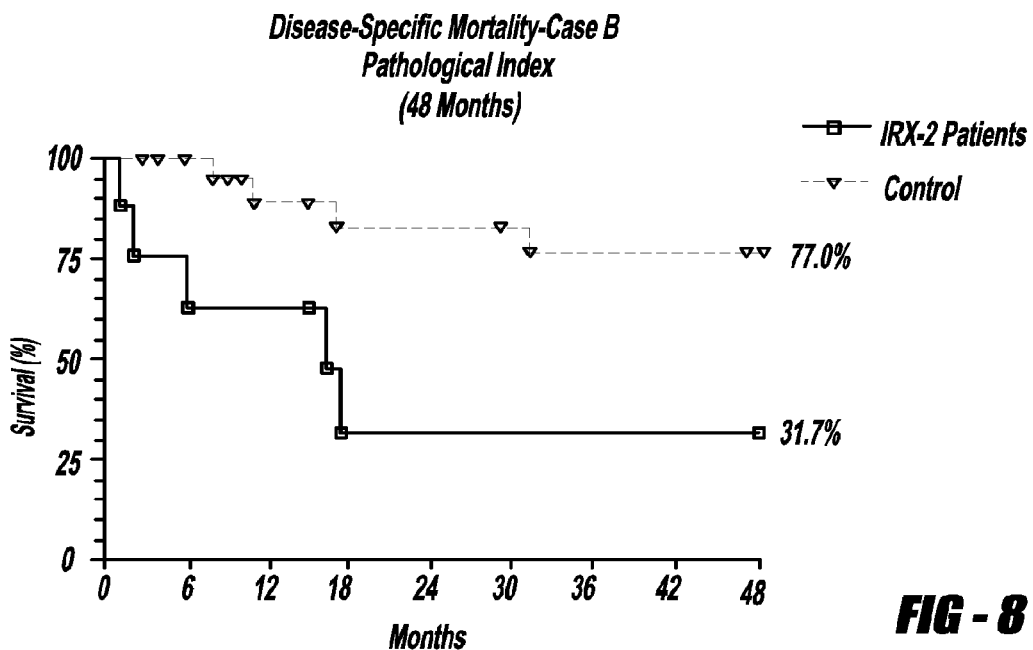
FIG. 8 is graph illustrating the relation of the pathology index to survival.
Figure 9:
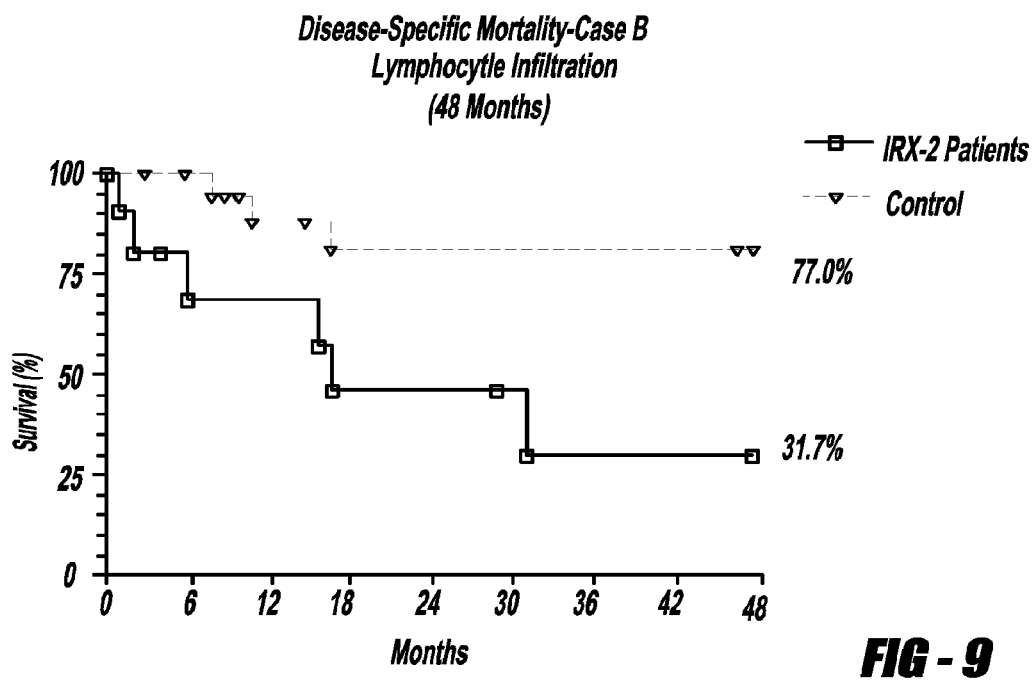
FIG. 9 is a graph showing the relationship of lymphocyte infiltration to survival.

Further analysis of the clinical, pathological and survival data of the aforementioned clinical trial study offer more insights into the nature of the invention as it relates to immunization of cancer patients to their own autologous tumor antigens and the resulting immune regression of their tumors. FIG. 6 shows that the treatment with the NCM (IRX-2) protocol is associated with increased survival at 48 months (p<0.01). FIG. 7 shows that positive clinical responses correlate with survival, i.e., patients with complete responses (CR) or partial responses (PR) (>50% tumor reduction) have a better survival than those with minor responses (MR) (<50%, but >25% tumor reduction) or no response (NR) (<25%) (p<0.01). FIG. 8 shows that patients with stronger pathological responses (index of 6-9) have a better survival than those with weaker pathological responses (<6) (p<0.02). FIG. 9 shows that lymphoid infiltration into the tumor as a single variable predicts survival (p<0.01). Chi Square analysis of the relationship of clinical response to the pathological response shows a highly significant relationship (p<0.01) indicating that the two correlate with each other as well as to survival, thus providing a statistical triangulation of the data interrelating clinical responses, immune regression parameters, and survival. Such relationships have never been shown for immunotherapy of a human cancer.

Figure 10:
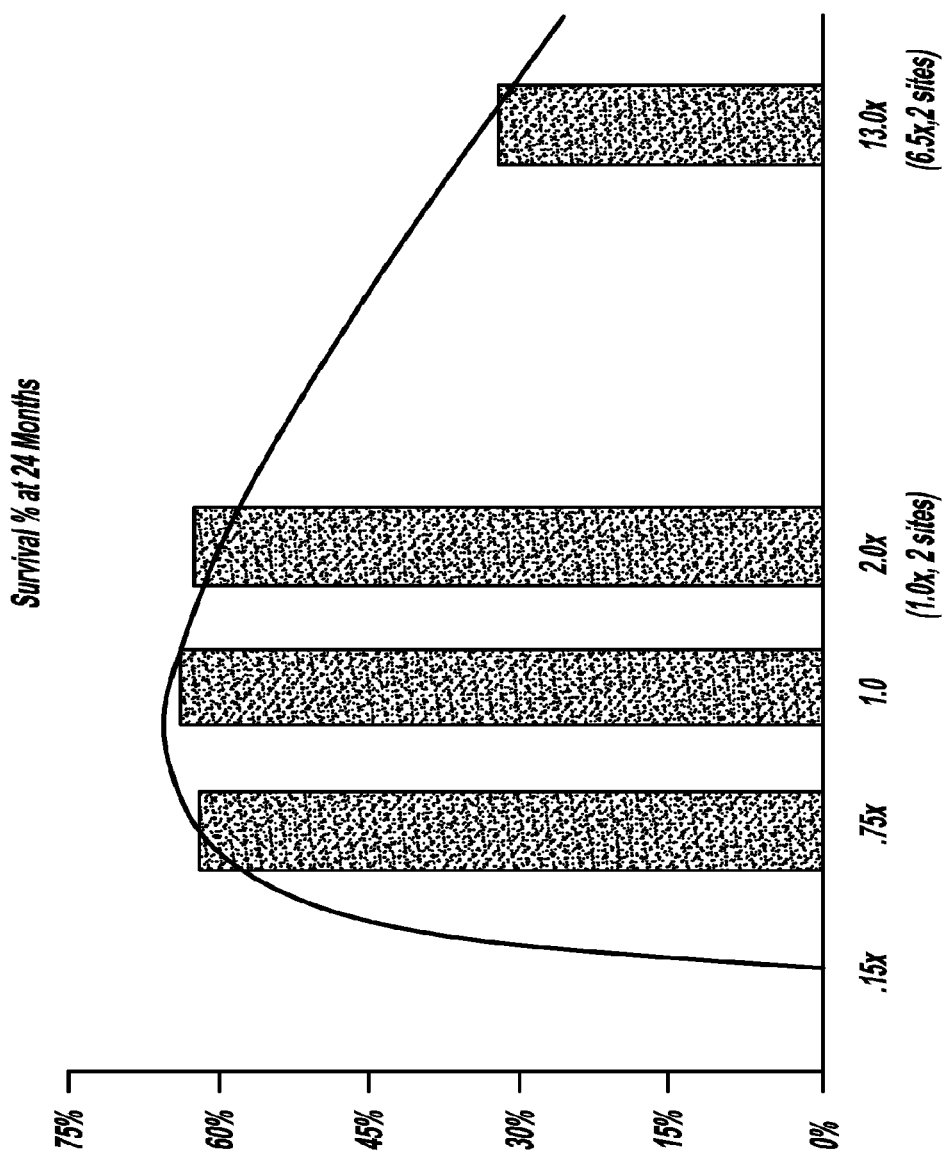
FIG. 10 is a graph illustrating the survival percentage (dose response) of treated patients at twenty-four months, wherein "x" is equal to about 100 IU/ml of IL-2.

Finally, FIG. 10 presents a dose response curve for the NCM of the present invention, relating dose to overall survival at twenty-four months. NCM treatment has an optimal impact on survival at about 100-233 international units of IL-2 equivalence.

Example 4

Two patients with lymphoma of the head and neck were treated according to the protocol as described above. The following scheme was followed.

Before treatment, the patients were skin-tested with NCM at 0.1 ml injected subcutaneously in the forearm, the region was marked, and 24 hours later, the test was read. The test was considered positive if the induction and erythema was equal or larger than 3 mm.

Case 1:

The patient was a 23-year-old male who presented with a prior history of a three month presence of a tumor on the left submaxillary region, with no other symptoms. In the emergency room, he was found to have lymph adenopathy of the left submaxillary triangle of approximately 6.5 cm in diameter of a hard consistency, partially fixed at deep levels. The rest of the physical exam was normal. The incisional biopsy showed Hodgkin's lymphoma. The lesion was staged ECIIA. A one-cycle treatment of NCM was given, obtaining a minor response, as the adenopathy reduced in size by 1 cm in diameter. The biopsy report obtained after NCM treatment showed 60% of the lesion showed normal lymphocytic infiltration, and the rest of the neoplasia (40%) showed necrosis. No viable tumor cells were found.

Following this, the patient received radiation treatment in the neck of 3600 rads. The patient was free of disease at two years.

Case 2:

The patient is an 82-year-old male, who presented with a two-month history of a painful mid-neck tumor mass, as well as a 10 kg loss of weight. On physical exam, the patient presented with tumor on the right palatine tonsil, which was enlarged to approximately 4×3 cm, with an ulcer in the center of the tonsil. On the neck, a right submaxillary lymph node measured approximately 2×2 cm and a lymph node mass at level II and III of approximately 5×5 cm. The rest of the exam was normal. The incisional biopsy of the tonsil and one of the neck lymph nodes demonstrated defined non-Hodgkin's lymphoma mixed, of intermediate grade.

The patient was subjected to two cycles of NCM at the end of which a 1 cm reduction in the diameter of the tonsil and neck adenopathy was observed. The pathological report post-NCM treatment showed 20% live tumor, 30% tumor fragmentation and necrosis, and 50% normal lymphocyte infiltration.

The patient was given chemotherapy (CHOP) for 6 cycles and later external radiotherapy (RT) at a total dose of 4600 rads. He recurred at eight months post RT with adenomegaly at the occipital level. The patient died three months later with evidence of neck disease.

Example 5

Ten patients with untreated early stage cervical cancer, clinically staged IB1, IB2 and IIA, were treated with local perilymphatic injections of NCM (10 daily injections) followed by radical hysterectomy at day 21. One day before starting the NCM treatment, patients received a single IV dose of CY at 300 mg/m. Oral INDO or ibuprofen and zinc sulfate were administered from days 1 to 21. The clinical and pathological response, toxicity and disease-free survival were evaluated.

All patients completed NCM treatment and were evaluated for response and toxicity. Clinical response was seen in 50% of patients (3 partial response (PR), 2 minor response (MR) (>25%<50% reduction)). Seven patients underwent surgery. Pathologically, tumor reduction associated with tumor fragmentation was found in five cases. There was a heterogeneous pattern of cell types infiltrating the tumor, which included lymphocytes, plasma cells, neutrophils, macrophages and eosinophils. Treatment was well-tolerated except for mild pain and minor bleeding during injection and gastric intolerance to INDO. At 24 months of follow-up, nine patients were disease-free.

This study shows that NCM treatment induces immune-mediated tumor response in early stage untreated cervical carcinoma.

Example 6

Two patients with liver metastasis from primary hepatocellular carcinoma were treated with intrasplenic NCM (1 or 3 injections). The protocol was as previously described for the H&NSCC, cervical, or lymphoma cases. One patient with advanced hepatocellular carcinoma had a partial response confirmed by tomography. The other had a partial response confirmed by surgery. Histological exam showed tumor reduction, fragmentation, and lymphoid infiltration.

Example 7

Four patients with squamous cell carcinoma of the penis (human papiloma virus associated) were treated with the NCM protocol as described above; all four had partial responses clinically and the surgical specimens showed tumor reduction and fragmentation and lymphoid infiltration characteristic of the H&N SCC cancer patients.

Example 8

Correction by NCM of T Lymphocytopenia

The objective of the following experiment was to assess the effect of a 10-daily injection treatment of NCM containing the six cytokines of IL-1, IL-2, IL-6, IL-8, IFN-γ, and TNF-α (115 units IL-2 equivalence/day) on lymphocyte counts (LC) of lymphocytopenic patients. These patients had recovered from prior surgery and radiotherapy for head and neck cancer, and had persistent lymphocytopenia with mean counts of 441 cells/1 mm$^3$. Normal levels of LC are 2000 cells/mm$^3$. The patients were free of cancer at the time of treatment. LC were obtained at day 0 and day 13. T lymphocytes (CD3+) and T cell subsets (CD4+ or CD8+) were assessed by cytofluorometry. Table II presents the data for five responding patients. Significant increases were observed for LC, CD3+, and CD4+ T cells.

TABLE II

| Pt. Number | TLC* | CD3* | CD4* | CD8* |
|---|---|---|---|---|
| 1 | 100 | 83 | 28 | 40 |
| 2 | 136 | 62 | 52 | 55 |
| 3 | 100 | 63 | 24 | 3 |
| 4 | 100 | 74 | 331 | −20 |
| 5 | 100 | 166 | 173 | −16 |
| Mean ± SEM | 107 ± 7 | 90 ± 19 | 122 ± 59 | 12 ± 15 |

*Changes in number of cells per mm$^3$ from day 0 to day 13.

These changes compare favorably to those achieved by much higher doses of pegylated interleukin 2 (3×10$^6$ units of recombinant IL-2) in lymphocytopenic AIDS patients (T. Merigan, personal communication) but with less toxicity. They are less than those achieved with 8-day infusions of >10×10$^6$ units/day of IL-2 in AIDS patients; however, the latter required great expense, inconvenience, and had significant toxicity (Kovaks, 1997). These results with NCM were obtained in the absence of INDO and CY and thus show that the effect of the regimen on LC is that of the NCM composition of the invention.

Example 9

NCM Stimulates Dendritic Cell Maturation and Activation

Figure 11:
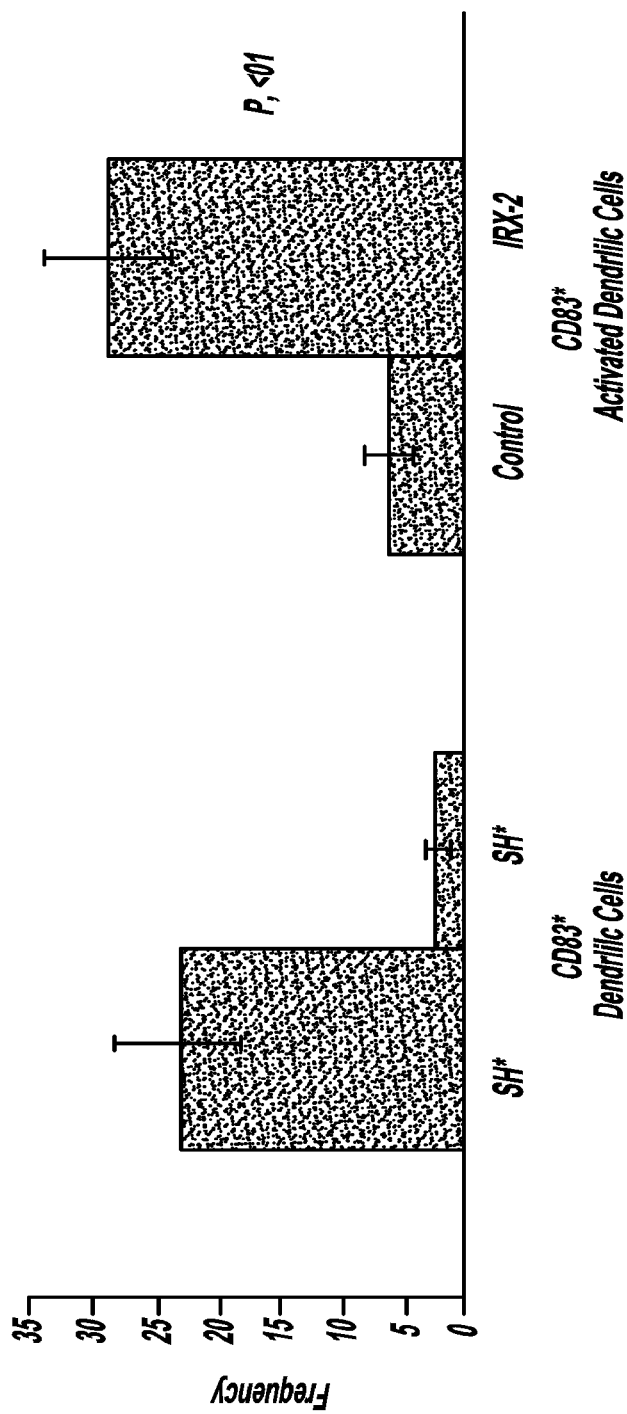
FIG. 11A is a bar graph illustrating the accumulation of partially mature CD83+ dendritic cells (DCs) in the lymph nodes of SH+ cancer patients.
FIG. 11B is a bar graph showing an increase in the number of CD86+ activated DCs upon treatment with NCM (IRX-2)

In previous experiments, lymph nodes from five NCM-treated H&NSCC patients and five untreated H&NSCC control patients were isolated and cellular constituents analyzed by flow cytometry using a panel of cell surface markers for dendritic cells (i.e., CD83+, CD86+, and CD68+). As noted above, sinus histiocytosis is a lymph node pathology seen in some cancer patients which is characterized by the accumulation in the lymph nodes of large histiocytes which represent immature dendritic cells. As demonstrated in FIG. 11A, patients with SH(SH+) have an accumulation of CD68+, CD83+, CD86− DCs in their lymph nodes, while those without noticeable SH have few CD83+ cells. However, NCM treatment resulted in a five-times increase in the number of CD86+ (concomitant with CD68+, CD83+) DCs compared to non-treated cancer controls, indicating a conversion to an "activated" DC phenotype. Controls are untreated H&NSCC patients compared to NCM-treated cancer patients (see FIG. 11B).

Since sinus histiocytosis represents an accumulation of partially matured DCs presumed to be bearing endogenous tumor peptides, full maturation and activation with expression of the co-stimulatory receptor CD86 reflects use of the NCM of the present invention to correct this defect on maturation and to allow effective antigen presentation to T cells. The NCM of the present invention thus reverses sinus histiocytosis and leads to effective immunization of naive T cells.

The data described above and subsequent data contained in Meneses et al. (2003) showed that the treatment of patients with H&NSCC using perilymphatic NCM, low dose CY, and INDO reversed the sinus histiocytosis frequently evident in the lymph nodes in this and other cancers. However, it was not apparent from this data which of the above agents, NCM, CY, and/or INDO, corrected this defect.

The following data present evidence that NCM containing the six cytokines of IL-1, IL-2, IL-6, IL-8, IFN-γ, and TNF-α induces DC maturation and activation in the absence of CY and/or INDO. The NCM (IRX-2) used in these experiments contains the six cytokines listed above or as shown in Table III below. For the purposes of these experiments, NCM (IRX-2) concentrations are expressed as the concentration of TNF-α contained in IRX-2. The cytokine concentration in IRX-2, including TNF-α, was measured by ELISA and the recombinant TNF-α purity is >95%. For all experiments, except titrations, NCM was used at a concentration of 1 ng/ml.

TABLE III

Cytokine levels in IRX-2 formulation Lot 041304 (ng/ml)

| IL-1β | IL-2 | IFN-γ | TNF-α | IL-8 | IL-6 | IL-10 | G-CSF | GM-CSF |
|---|---|---|---|---|---|---|---|---|
| 0.3 | 4.2 | 2.2 | 1.0 | 25.2 | 0.7 | 0.03 | 0.06 | 0.4 |

The medium used was RPMI 1640, supplemented with 2 mM L-glutamine, 50 μg/ml streptomycin, 50 U/ml penicillin and 10% FBS (all reagents purchased from Celigro, Herndon, Va.). GM-CSF, TNF-α and VEGF$_{165}$ were purchased from Peprotech (Rocky Hill, N.J.). X-VIVO 10 was purchased from BioWhittaker (Walkersville$_1$ MD). LPS was purchased from Sigma (St. Louis, Mo.). All reagents were tested for endotoxin contamination with the sensitive *Limulus amebocyte* lysate assay (LAL assay; BioWhittaker) according to the manufacturer's instructions and were found to be negative. All solutions were found to contain less than 0.06 EU/ml, the lowest detection limit. Additionally, all plastic ware was pyrogen-free.

PBMCs used in these experiments were obtained from 30 ml of leukocyte enriched buffy coat of healthy donors by centrifugation with Ficoll-Hypaque centrifugation (Celigro, Herndon, Va.), and the light density fraction from the 42.5-50% interface was recovered. The cells were resuspended in culture medium and allowed to adhere to 6-well plates (Costar, Cambridge, Mass.). After 2 hours at 37° C., nonadherent cells were removed by washing and adherent cells (.about.90% CD14$^+$ cells, i.e., monocytes) were cultured in 3 ml of medium supplemented with 50 ng/ml GM-CSF (500 U/ml) and 50 ng/ml IL4 (500 U/ml).

For surface marker analysis, the following fluorochrome-conjugated mAbs (all from BD Pharmingen, San Diego, Calif.) were used: CD86-PE, CD80-FITC, CD54-APC, CD83-PE, HLA-DR-FITC, CD1a-APC, CD40-FITC and appropriate isotype controls. Immunophenotypic analysis was performed using FACS. Cells (0.25×10$^6$) were washed in PBS supplemented with 2% FBS and 0.1% NaN$_3$ (FACS wash buffer) and incubated for 30 min at room temperature with APC-, PE-, or FITC-conjugated mAbs or with the corresponding isotype-matched mAb. Excess mAb was removed by washing in FACS wash buffer. Results were expressed as either mean fluorescence intensity or percentage of cells expressing the specified antigen, Fluorescence analysis was performed on a FACSCalibur flow cytometer (BD Biosciences, Rockville, Md.) after acquisition of 10,000 events and analyzed with BD Biosciences CellQuest software (Rockville, Md.).

Figure 12:
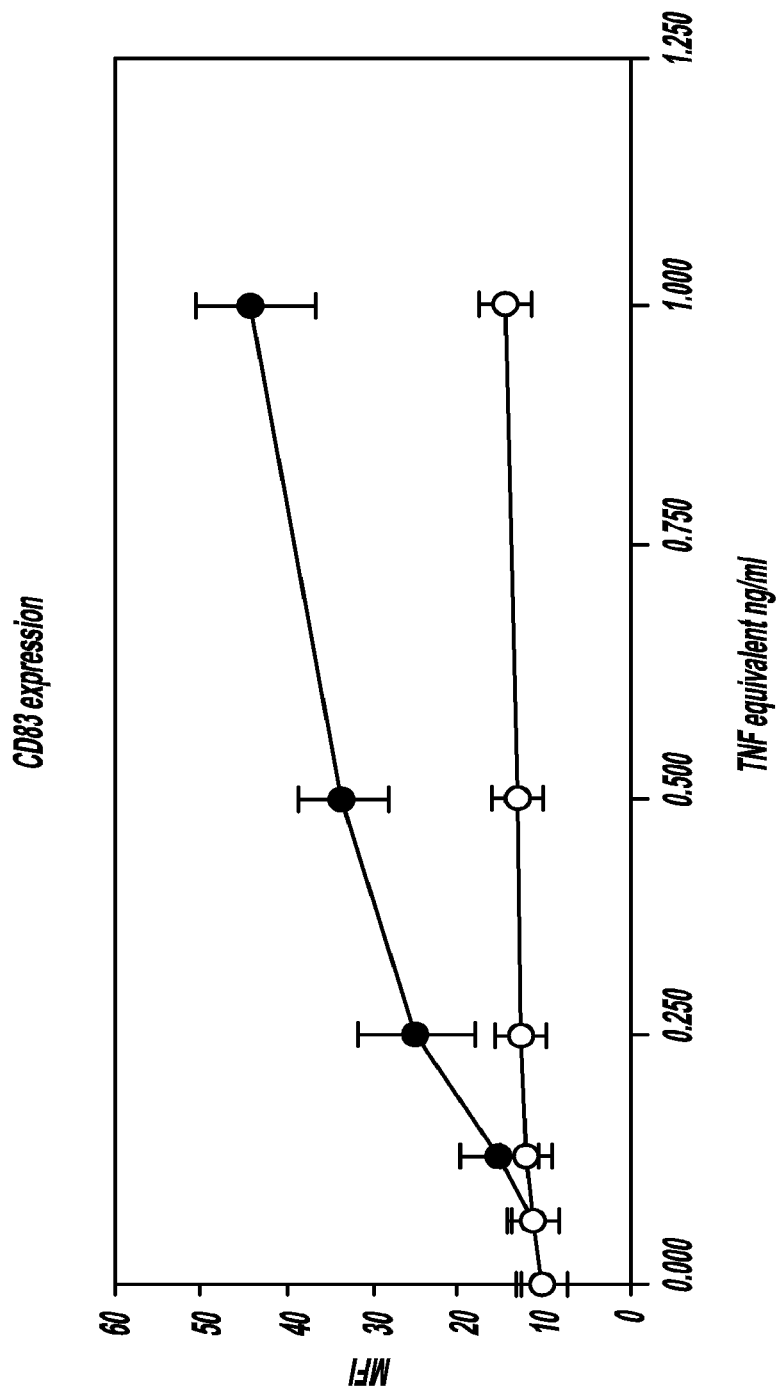
FIG. 12 is a graph showing that NCM (IRX-2) induces DC maturation as detected by increased CD83 expression on DCs.

As demonstrated in FIG. 12, the NCM composition of the invention increased the number of DCs bearing the CD83 antigen, a key marker of DC maturation. More specifically, adherent PBMCs were cultured for 7 days in the presence of GM-CSF and IL4 as described above and then stimulated with increasing amounts of either recombinant TNF-α (PeproTech) or NCM (IRX-2). After 48 hrs, the cells were washed and analyzed for CD83 expression by flow cytometry. FIG. 12 indicates that NCM is active at inducing DC maturation, as evidenced by an increase in CD83+ cells. Moreover, NCM was more active at inducing DC maturation than an equivalent dose of TNF-α alone. The data in FIG. 12 are represented as the mean of 5 individual experiments −/+SEM ($p<0.0001$, by ANOVA).

These data indicate that NCM promotes the maturation of DCs and does so in a way that cannot be accounted for by any single cytokine contained in the NCM mixture that is known to act on DC maturation. For example, normal in vitro differentiation of PBMCs requires the presence of 100-500 U/ml GM-CSF (approximately 10-50 ng/ml) and 500-1000 U/ml IL-4 (50-100 ng/ml). This generates a population of cells committed to the DC lineage but in a relatively immature state (low/moderate CD86, CD40, HLA-DR expression, null for CD83). Undiluted NCM has undetectable quantities of IL-4 and contains 10 to 50-fold lower concentrations of GM-CSF (approximately 1.1 ng/ml) than is required for in vitro differentiation of DCs. Thus, the individual IL-4 and GM-CSF cytokines in the NCM cannot account for the CD83+ cells produced in the cultures of FIG. 12.

TNF-α can induce such cells but at concentrations well above those contained in the NCM of the invention (see FIG. 12). For example, after initial commitment to the dendritic cell lineage (by several days of GM-CSF+IL-4 in vitro), subsequent addition of a "danger signal" such as that derived from a pathogen (e.g., LPS) induces a fully mature dendritic cell phenotype including high/strong expression of CD86, CD40, HLA-DR, and the presence of CD83. TNF-α in the range of 20-50 ng/ml can largely mimic such a pathogen-derived danger signal resulting in upregulation of the same markers. However, the undiluted NCM mixture has only 2.8 ng/ml of TNF-α on average, far below the TNF-α concentrations required for full DC maturation. Thus, the results depicted in FIG. 12 clearly demonstrate that, at the TNF-α equivalent concentrations used in this experiment, the induction of the CD83 marker by NCM could not be due solely to the presence of the TNF-α in the NCM mixture.

Figure 13A:
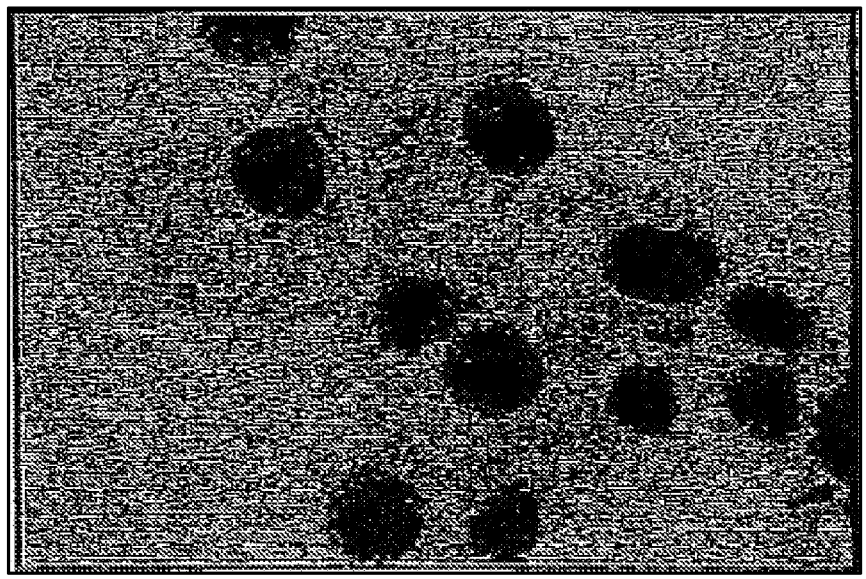
FIG. 13A and FIG. 13B depicts the effect of NCM on the morphology of monocyte-derived DCs in cytospin preparations. The cells treated with NCM (FIG. 13B) exhibited the morphological characteristics of mature DCs such as cellular projections and large irregular shaped nuclei.
Figure 13B:
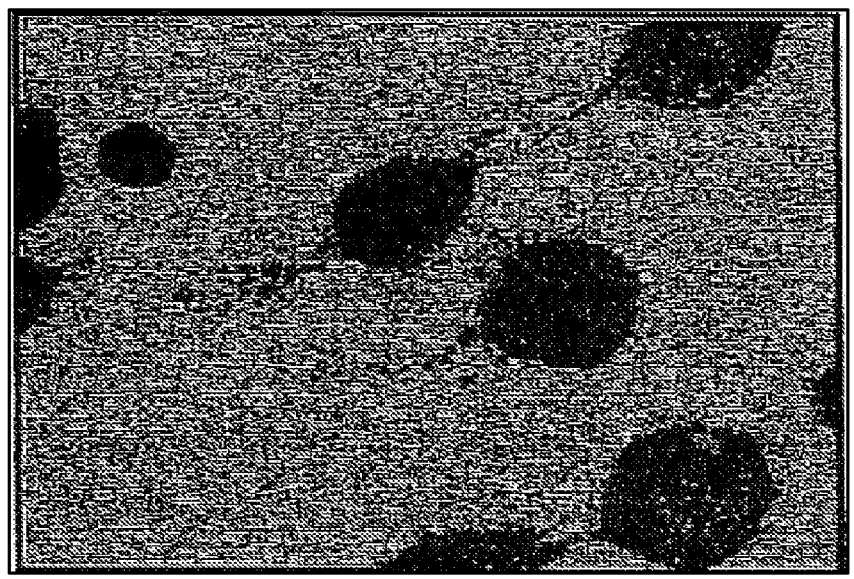

Since it is known that DCs undergo distinct morphological changes as they progress from immature to mature cells, immature DCs were treated with NCM to determine if NCM treatment changed the morphology of the cells. More specifically, adherent PBMCs were grown in the presence of GM-CSF (500 U/ml) and IL-4 (500 U/ml) for 4 days as described above (which treatment is known to yield immature DCs) and then were either treated with NCM (IRX-2) or left untreated as controls. After 3 days, the cells were visualized by Wright staining and microscopy. As shown in FIG. 13, the cells treated with NCM (FIG. 13B) exhibited the characteristic cellular projections and motility of mature DCs, and continually extended and retracted their cellular processes and veils. These cells had large irregular shaped nuclei, numerous vesicles, relatively few cytoplasmic granules, and noticeable and abundant cellular projections as compared to the untreated controls (FIG. 13A). Thus, NCM treatment resulted in DCs that possessed typical mature DC morphology.

In addition, it is known that the prototypical transition from immature to mature DCs results in well characterized increases and decreases in certain cell surface antigens. For example, immature DCs express high levels of CD1a, and upon encounter with stimuli such as cytokines or bacterial products, this marker is down-regulated. Thus, to determine if NCM treatment resulted in the gain or loss of cell surface markers associated with the activation and maturation of DCs, GM-CSF and IL-4-treated adherent PBMCs (monocytes) (as described above) were grown for 7 days and then incubated for 48 hrs with or without NCM (IRX-2). Expression of CD1a, HLA-DR, CD86, CD40 and CD54 was examined by flow cytometry and expressed as mean fluorescence intensity.

Figure 14:
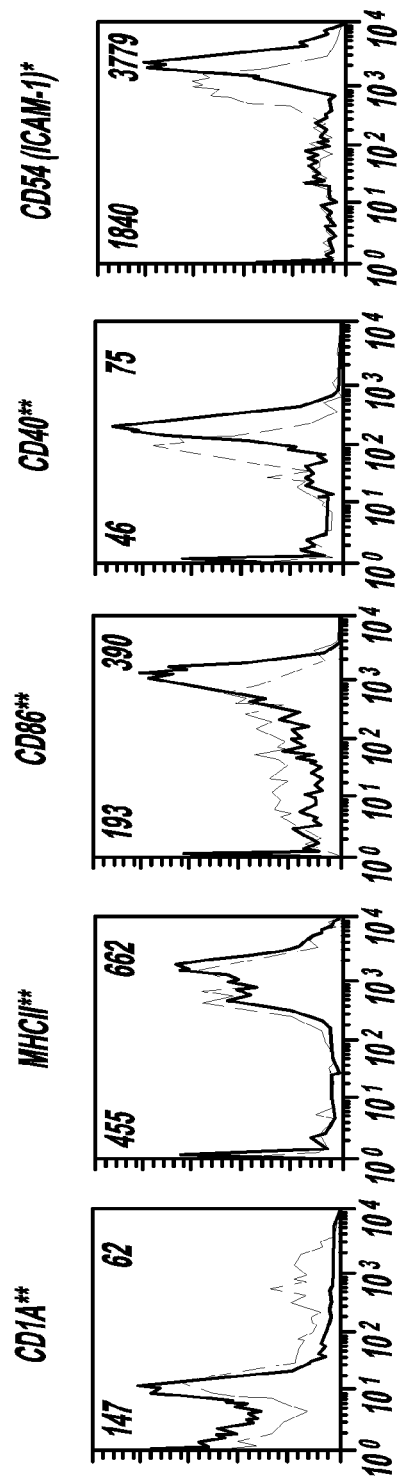
FIG. 14 contains histograms showing down-regulation of CD1a antigen and up-regulation of MHCII, CD86, CD40, and CD54 (ICAM-1) antigen expression by peripheral blood mononuclear cells (PBMCs) incubated with NCM (IRX-2). These changes indicate that NCM stimulates the maturation of DCs.

As demonstrated by the histograms of FIG. 14, NCM (IRX-2) treatment of immature DCs (indicated by solid lines in the histograms) resulted in the down-regulation of CD1a expression (147 vs. 62) as well as the up-regulation of MHCII expression (455 vs. 662). In addition, NCM treatment led to an increase in cell size and a decrease in granularity (data not shown). Untreated controls are indicated by dashed lines in each histogram. The mean values for untreated DCs are shown in the left upper corner of the panels; the respective values for DCs treated with NCM are shown in the upper right corner. Histograms shown are from a representative experiment and the values represent mean results from at least 10 individual experiments (*=$p<0.05$, =$p<0.002$, *=$p<0.00005$, paired Students t-test). As further indicated by FIG. 14, NCM (IRX-2) treatment enhanced the expression of co-stimulatory surface molecules CD86 (also known as B7-2) (193 vs. 390), CD40 (46 vs. 75), and CD54 (also known as intercellular adhesion molecule 1 or ICAM-1) (1840 vs. 3779). All of these changes in surface marker expression indicate that the NCM of the invention is a potent effector of DC activation.

Consistent with their role as antigen-presenting cells, immature DCs have a high endocytic activity and actively take up antigens. Upon maturation, this activity is down-regulated, whereupon the DC is engaged in antigen processing and presentation. Under physiological conditions, the down-regulation of APC endocytosis is associated with an increase in peptide/MHC complexes on the surface leading to enhanced stimulation of T cells. To test the influence of NCM (IRX-2) on endocytosis, DCs were incubated with increasing amounts of NCM (IRX-2) and the ability to internalize FITC-dextran was determined. More specifically, adherent PBMCs (monocytes) were treated with GM-CSF and IL-4 (as described above) for four days and then stimulated with TNF-α (at 1 μg/ml) or with increasing concentrations of NCM (IRX-2) up to the equivalent of 1 ng/ml TNF-α. After 18 hrs, the cells were incubated with FITC-Dextran (Sigma, St. Louis, Mo.), which was added to a final concentration of 1 mg/ml. The cells were cultured for 30 min at 37° C. After incubation, the cells were washed four times with ice-cold PBS and analyzed by flow cytometry as described above.

Figure 15:
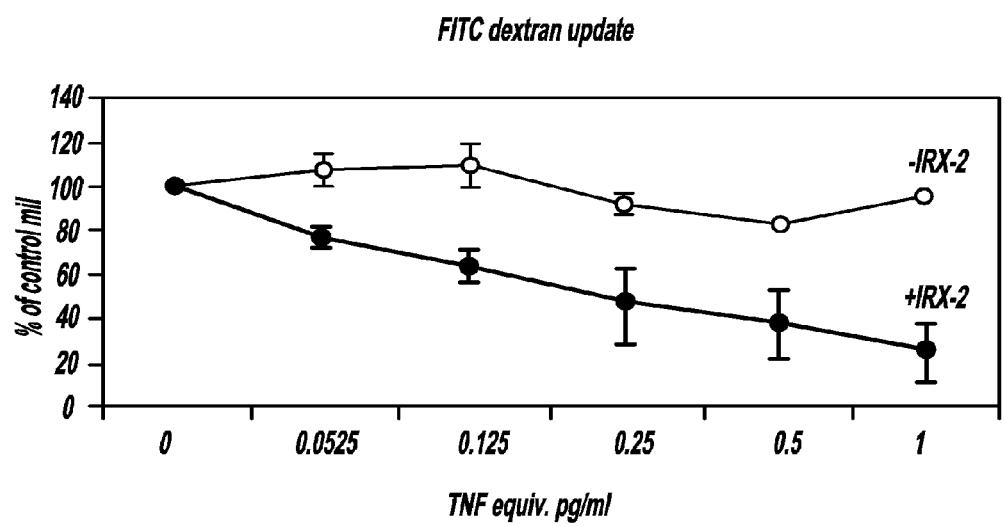
FIG. 15 is a graph showing that NCM (IRX-2) reduces the endocytic activity of immature DCs, which reduced activity is indicative of DC maturation.

As shown in FIG. 15, immature DCs incubated with NCM (IRX-2) (closed circles) down-regulated endocytosis in a dose-dependent manner. TNF-α treatment (open circles) at the corresponding dose found in the NCM had minimal effects. Treatment of immature DCs with higher amounts of TNF-α (10-25 ng/ml) did result in the down-regulation of endocytic activity as expected (data not shown). The data of FIG. 15 are shown as the percentage of mean fluorescence intensity of the stimulated versus the unstimulated DCs and are the mean of 4 independent experiments −/+SEM ($p<0.00001$, by ANOVA). These experiments indicate that the NCM of the invention down-regulates the endocytic activity of DCs, an indication of DC maturation.

Next, the ability of NCM to enhance the T cell stimulatory capacity of DCs was evaluated. Activated, mature DCs are potent stimulators of naive T cells. In order to show that NCM (IRX-2) treatment was translated into functional effects as well as the phenotypic and morphologic changes noted above, the influence of NCM (IRX-2) on the T cell stimulatory capacity of DCs was assessed in a mixed lymphocyte reaction (MLR) proliferation assay.

More specifically, adherent PBMCs (monocytes) were first treated with GM-CSF and IL-4 (as described above) for seven days and then stimulated with or without NCM (IRX-2). After 48 hrs, the NCM (IRX-2)-treated or untreated DCs were collected and assayed in an MLR as follows: purified DCs were co-cultured with $1 \times 10^5$ T cells from an unrelated donor at ratios of 1:5, 1:10, 1:30, and 1:100 DC:T cells. Allogeneic T-cells were prepared by running PBMCs purified from buffy coats by Ficoll-Hypaque gradient centrifugation over a nylon wool column. The assays were performed in triplicate in round-bottom 96-well plates. No NCM (IRX-2) was present during the MLR assay. After 5 days of DC-T cell co-culture, the wells were pulsed for 18 hours with BrDU. BrDU incorporation was measured using a colorimetric BrDU incorporation assay (Roche Diagnostics, Indianapolis, Ind.).

Figure 16:
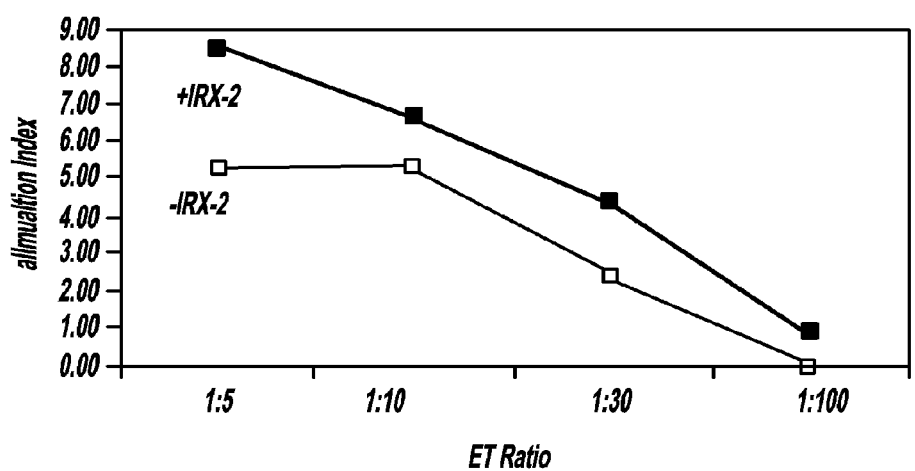
FIG. 16 is a graph showing that NCM (IRX-2) enhances the T cell stimulatory capacity of DCs, which enhancement is indicative of DC maturation and activation.

As shown in FIG. 16, DCs exposed to NCM (IRX-2) (closed squares) two days before co-culture were more potent in inducing a T cell proliferation response than untreated DCs (open circles), confirming that NCM-treated DCs are functionally competent. The data in FIG. 16 are expressed as stimulation index which is defined as ((o.d. DC stimulated T cell-o.d. DC alone)/o.d. resting T cell)−/+SEM and are the mean result of 4 individual experiments ($p<0.05$, by ANOVA).

It is important to note that there was no NCM in the co-cultures and the observed increase in T cell stimulation was due to the stimulatory effects of NCM on DCs, rather than a direct effect of the NCM on T cells. Thus, the NCM of the invention enhances the T cell stimulatory activity of DCs as shown by enhanced proliferation in allogenic MLR reactions. Moreover, NCM was shown above to increase the expression of ICAM-1 (CD54). This cell surface accessory ligand has been shown to be involved in signaling through LFA-1 and results in a bias towards a Th1 phenotype (Rogers, 2000). In a cancer setting, the functional consequence of these effects is that NCM-treated DCs would polarize the T cell response towards a Th1 phenotype and favor the activation of tumor-specific CTL activity, thus promoting tumor rejection.

Our data also demonstrate that NCM stimulates the production of IL-12 from DCs. IL-12 is a potent Th1 polarizing cytokine secreted by DCs in response to pathogens during infection. However, one of the most important roles of DCs in mediating tumor rejection is to effectively and efficiently stimulate Th1-biased anti-tumor T cell responses and one of the critical cytokines in directing this response is IL-12, IL-12 is produced by activated DCs and is an essential factor involved in the differentiation of naive $CD4^+$ helper T cells into Th1 cells. Th1 cells secrete IFN-γ and IL-2 and these cytokines along with IL-12 mediate the activation and proliferation of cellular and phagocytic components of the immune system, such as $CD8^+$ cytotoxic T lymphocytes (CTL).

To determine whether NCM can induce IL-12 production in DCs, GM-CSF/IL-4 cultured monocytes were stimulated with NCM (IRX-2) for 18 hours and assayed for intracellular IL-12 p70 production. More specifically, adherent PBMCs were grown for 4 days in GM-CSF and IL-4 (as described above) and then treated with or without NCM (IRX-2) or LPS for 18 hours. Brefeldin A (BFA; 10 µg/ml; Sigma, St. Louis, Mo.) was added during the last 4 hours to accumulate most of the cytokine in the Golgi complex. Cells were fixed and permeabilized using Fix and Perm (Caltag, Burlingame, Calif.), according to the manufacturer's instructions, and were then labeled with FITC-labeled mAb against IL-12 p70 (BD Pharmingen, San Diego, Calif.) or the appropriate isotype control (BD Pharmingen, San Diego, Calif.). Cells were analyzed by flow cytometry.

Figure 17A:
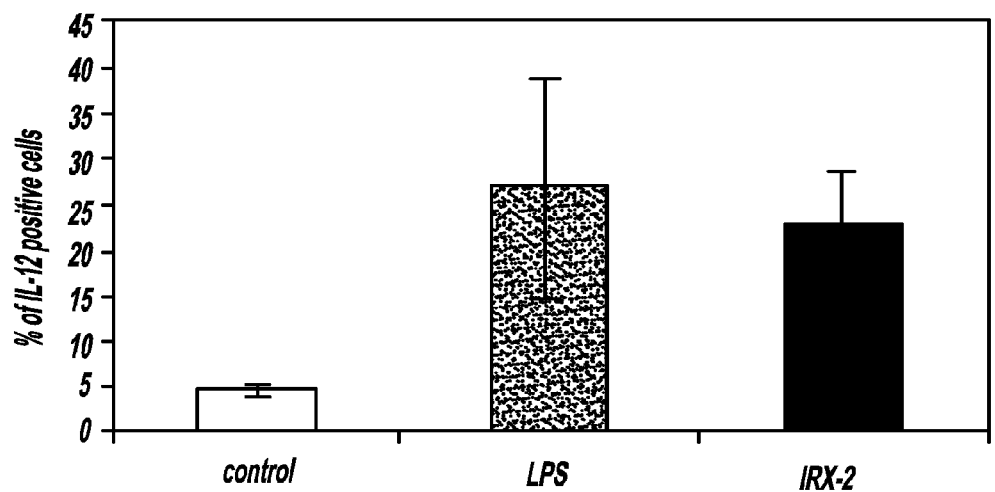
FIG. 17A is a bar graph showing that NCM (IRX-2) increases the number of DCs producing IL-12 intracellularly. IL-12 is a cytokine produced by mature activated DOCs.
Figure 17B:
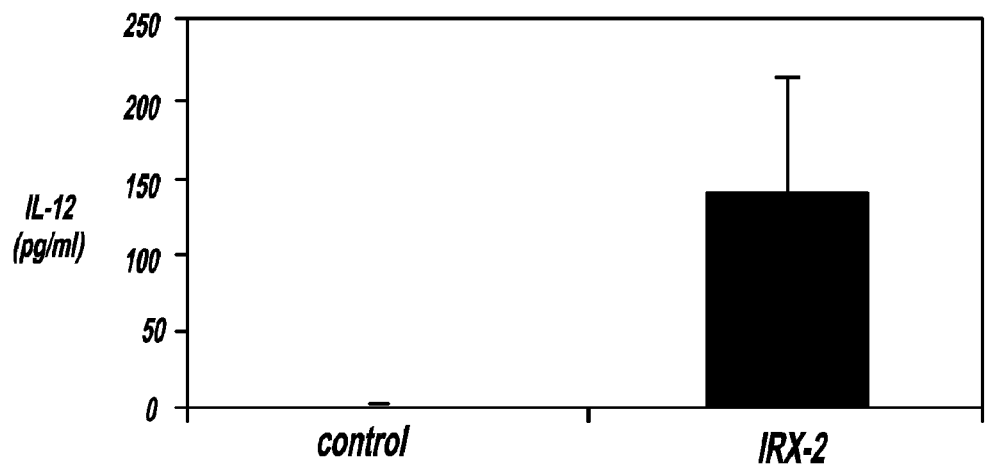
FIG. 17B is a bar graph showing that NCM (IRX-2) increases the total amount of bioactive IL-12 secreted by DCs.

As shown in FIG. 17A, NCM (IRX-2) increased the percentage of DCs producing IL-12 from 4.5% positive to 22.5% on average. LPS, a stimulator of IL-12 production in DCs, was used as a positive control and gave similar levels of induction relative to NCM (27%.+−0.11). The data of FIG. 17A are the mean of 4 independent experiments and are expressed as the percentage of cells staining positively for IL-12−/+SEM ($p<0.05$ Students t-test). To confirm that the increased intracellular production of IL-12 corresponded to increased secretion of bioactive IL-12, the concentration of bioactive IL-12 in the supernatant of NCM-treated DCs (cultured initially for 4 days with GM-CSF and IL-4 as described above and incubated with NCM for 48 hrs) was measured using a commercial ELISA kit (R&D Systems, Minneapolis, Minn.) that detects the bioactive p70 heterodimer. Thus, as shown in FIG. 17B, 48 hours after exposure to NCM, DC supernatants contained significantly more bioactive IL-12 than control-treated DCs. The data of FIG. 17B are the mean (−/+SEM) of 6 independent experiments ($p<0.05$, Students t-test).

Finally, our data indicated that NCM reduces VEGF-induced apoptosis in DCs. VEGF is an inhibitor of DC maturation and has been shown to increase apoptosis levels in maturing DCs. To determine if NCM was able to mitigate the effects of VEGF, DCs were treated with VEGF with or without IRX-2 and the level of apoptosis was determined by Annexin-FITC V binding. More specifically, adherent PBMCs were treated with GM-CSF and IL-4 for 7 days and then incubated in the presence or absence of VEGF (100 ng/ml) with or without NCM (IRX-2) (1:3) for 2 additional days. The cells were harvested and washed 2 times in ice-cold PBS and resuspended in Annexin binding buffer (BD Pharmingen, San Diego, Calif.). Annexin-V FITC (BD Pharmingen, San Diego, Calif.) and propidium iodide was added and the cells were incubated at 4° C. for 30 minutes. Cells were analyzed by flow cytometry.

Figure 18:
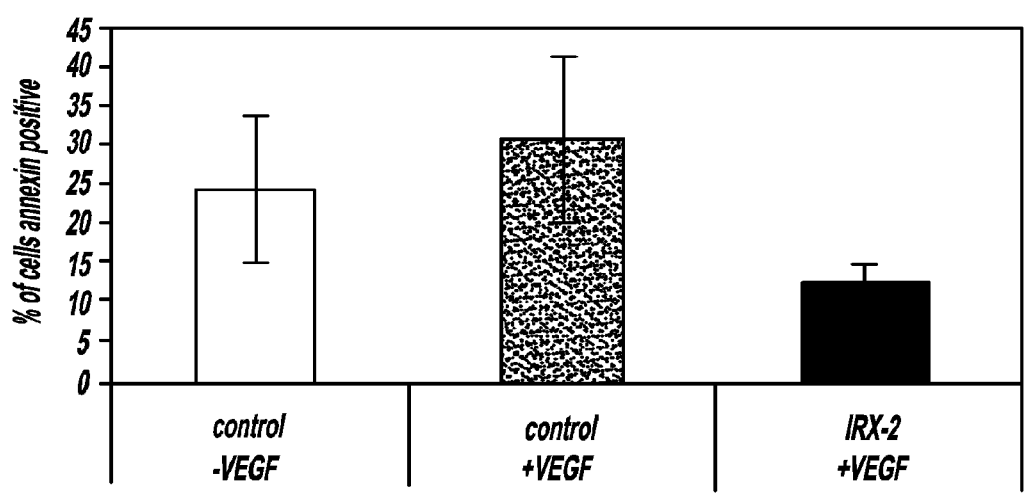
FIG. 18 is a bar graph showing that NCM (IRX-2) decreases VEGF-mediated apoptosis in DCs, indicating a protective effect of NCM on DC survival.

As shown in FIG. 18, apoptosis levels increased in VEGF-treated cells as compared to controls; however, NCM (IRX-2) reduced the level of apoptosis in VEGF-treated cells. The data of FIG. 18 are the result of 4 independent experiments and is expressed as the percentage of cells staining positively for Annexin V-FITC (−/+SEM). The data suggest that, in addition to its stimulatory capacity, NCM also has a protective effect on mature DCs. Moreover, defective DC function and number may be mediated in part by aberrant VEGF expression by the tumor (Gabrilovich, 1996b; Saito, 1999; Takahashi, 2004). VEGF production by tumors was shown to be a predictor for poor prognosis in several cancers including H&NSCC, lung cancer, gastric cancer, and osteosarcoma (Gallo, 2001; Kaya, 2000; Miyake, 1992; Saito, 1998; Smith, 2000). The data contained herein indicate that NCM can reverse VEGF-mediated apoptosis of DCs, thus promoting the survival of mature DCs within a tumor environment and allowing for prolonged antigen presentation and activation of tumor antigen-specific cytotoxic T lymphocytes.

Previous studies with DCs have employed natural cytokine mixtures such as monocyte-conditioned media (MCM) or mixtures of recombinant inflammatory cytokines containing TNF-α, IL-1.beta., IL-6, and PGE$_2$ to mature DCs for use in ex vivo generated DOC-based cancer vaccines (Romani, 1996; Bender, 1996; Sorg, 2003). A critical difference between NCM and the cytokine mixtures used in other studies is that the level of cytokines used in this study were 10-100 fold lower, suggesting a significant synergism between the unique cytokine components of NCM. In addition, there are significant problems involved in the use of DCs matured by these other mixtures. For example, DCs matured in the presence of TNF-α, IL-1.beta., IL-6, and PGE$_2$ have low or absent production of IL-12 and if improperly activated, may be tolerogenic (Steinman, 2002; Langenkamp, 2000). Additionally, there is a concern that fully mature DCs generated ex vivo might be "exhausted" and unable to efficiently prime an effective T cell response (Kalinski, 2001). The low levels of clinical responses seen in patients treated with DCs matured by the ex vivo method lends support to these concerns (Holtl, 2002; Schuler-Thurner, 2002; Thurner, 1999).

The evidence presented herein confirms that NCM is a potent activator of dendritic cells. This data combined with the known effects of NCM on T cells (Hadden, 1995b) suggests that NCM is able to overcome the APC and T cell defects found in cancer patients and provides a mechanistic explanation for the successful clinical outcomes seen in Applicant's clinical trials. While DCs are now recognized as central players in cancer-directed immunotherapy, it is becoming increasingly clear that manipulating single elements of the immune system individually, e.g., tumor-specific T cell vaccination strategies or reintroduction of tumor-antigen pulsed DCs alone, is failing to produce significant clinical improvements for patients (Ridgway, 2003; Rosenberg, 2004). A more beneficial treatment plan may be to enhance the activities of several coordinating cell types concomitantly, e.g., T cells and DCs, allowing reinforcing interactions and a better likelihood that functional cascades are perpetuated rather than blocked by the tumor's various immunosuppressive strategies. In this setting, the NCM of the invention may be acting to stimulate both endogenous DCs loaded with tumor antigen and tumor antigen-specific cytotoxic T cells, resulting in an effective immune response and tumor rejection. Taken together, these results indicate that the cytokine composition of the present invention can be a powerful clinical tool for eliciting an immune response against endogenous tumor antigens or could be used in conjunction with exogenously added tumor antigens in a cancer vaccine setting.

Example 10

NCM Stimulates Monocyte/Macrophage Activation

Figure 19B:
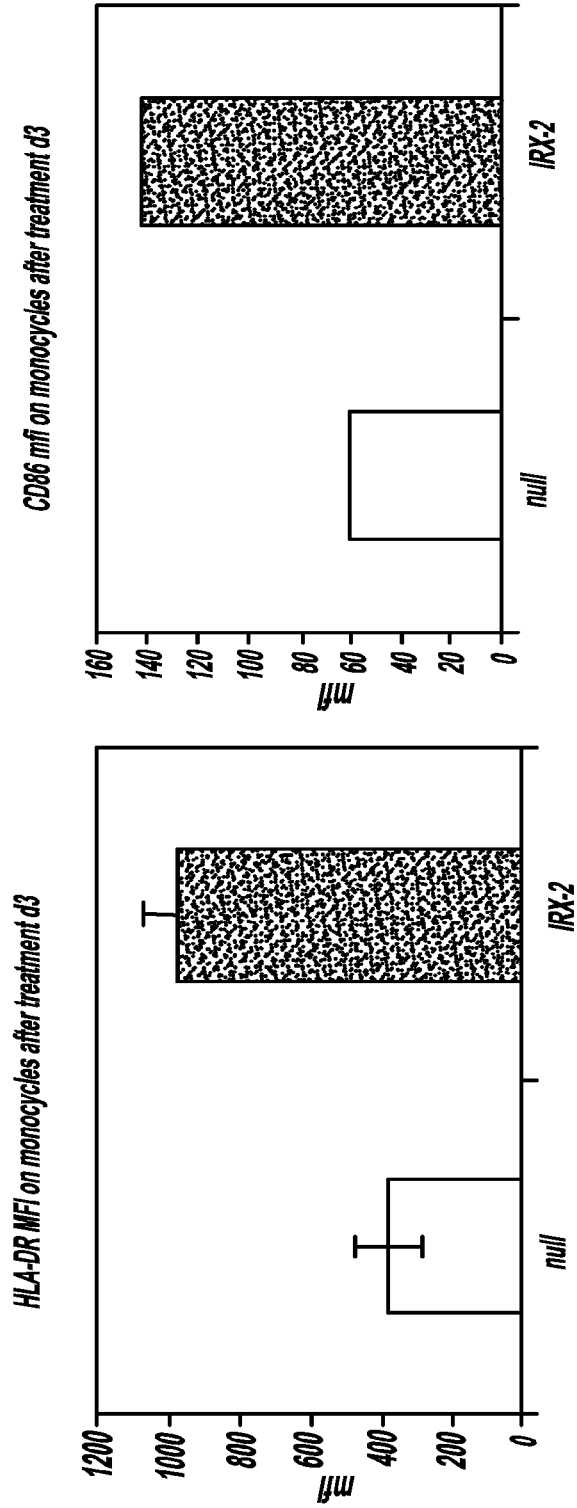
FIG. 19B is a series of bar graphs depicting the increase in mean fluorescence intensity (MFI) for the activation markers, CD86, HLA-DR, CD80 and CD40, after treatment of adherent PBMCs with NCM, as determined by flow cytometry.
Figure 19C:
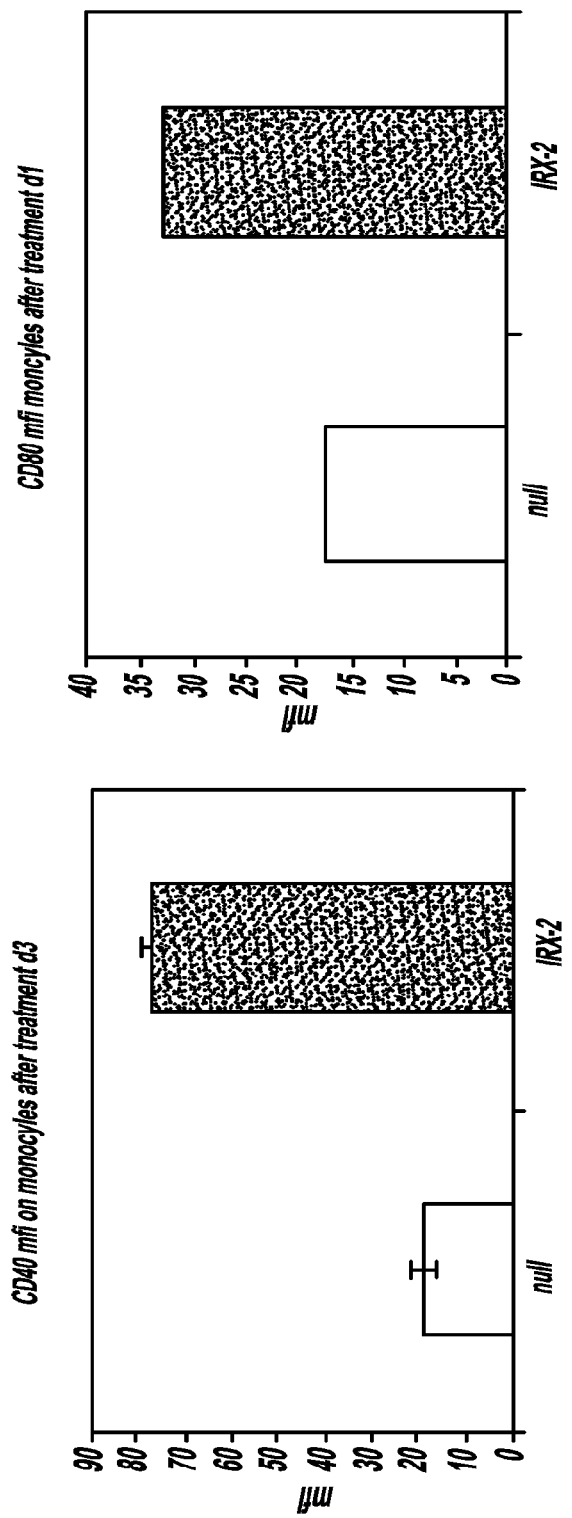
FIG. 19C contains two bar graphs showing CD40 mfi on monocytes after treatment d3 and CD80 mfi monocytes after treatment d1.

The NCM of the invention containing the cytokines IL-1, IL-2, IL-6, IL-8, IFN-γ, and TNF-α is also a potent activator of monocytes/macrophages. More specifically, adherent PBMCs (~90% monocytes) were grown overnight in X-VIVO 10 media (BioWhittaker Bioproducts), stimulated for 24 hr with NCM (IRX-2) (at a 1:3 final concentration) and assayed for the expression of various activation markers typically found on activated macrophages by flow cytometry. As a control, cells were incubated for 24 hr in media lacking NCM. As demonstrated in FIG. 19, the treatment of the cells with NCM versus no added cytokines produced a statistical increase in the percentage of cells staining positively (FIG. 19A) and an increase in mean fluorescence index (MFI) (FIG. 19B) for HLA-CR, CD86, CD40 and CD80, all activation markers of monocytes/macrophages (p<0.03). The data shown in FIG. 19 represent the mean value+/−SEM from three independent experiments/donors.

Figure 20:
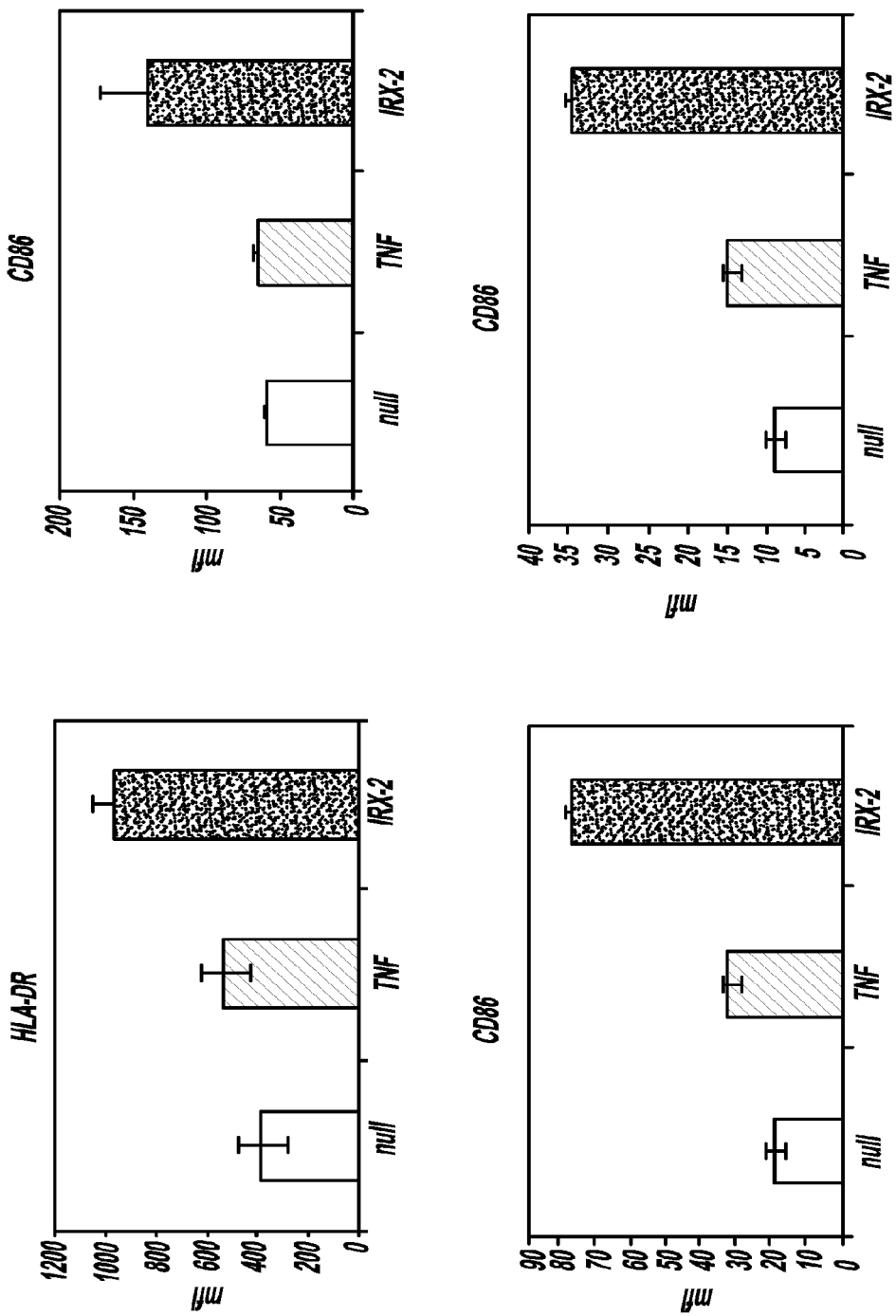
FIG. 20 contains bar graphs demonstrating that the NCM of the invention activates monocytes/macrophages, i.e., induces the expression of activation markers, CD86, HLA-DR, CD80 and CD40, to a greater degree than TNF-α.

In addition, it was found that the NCM of the invention activates monocytes to a greater degree than TNF-α. More specifically, adherent PBMCs were stimulated with either NCM (IRX-2) (at a 1:3 final concentration; approximately 1 ng/ml TNF-α) or TNF-α (10 ng/ml) and assayed for the expression of activation markers by flow cytometry. As shown in FIG. 20, NCM induced statistically greater expression of HLA-DR, CD86, CD40 and CD80 than TNF-α (p<0.03). The data shown in FIG. 20 represent the mean value+/−SEM from three independent experiments/donors.

Figure 21:
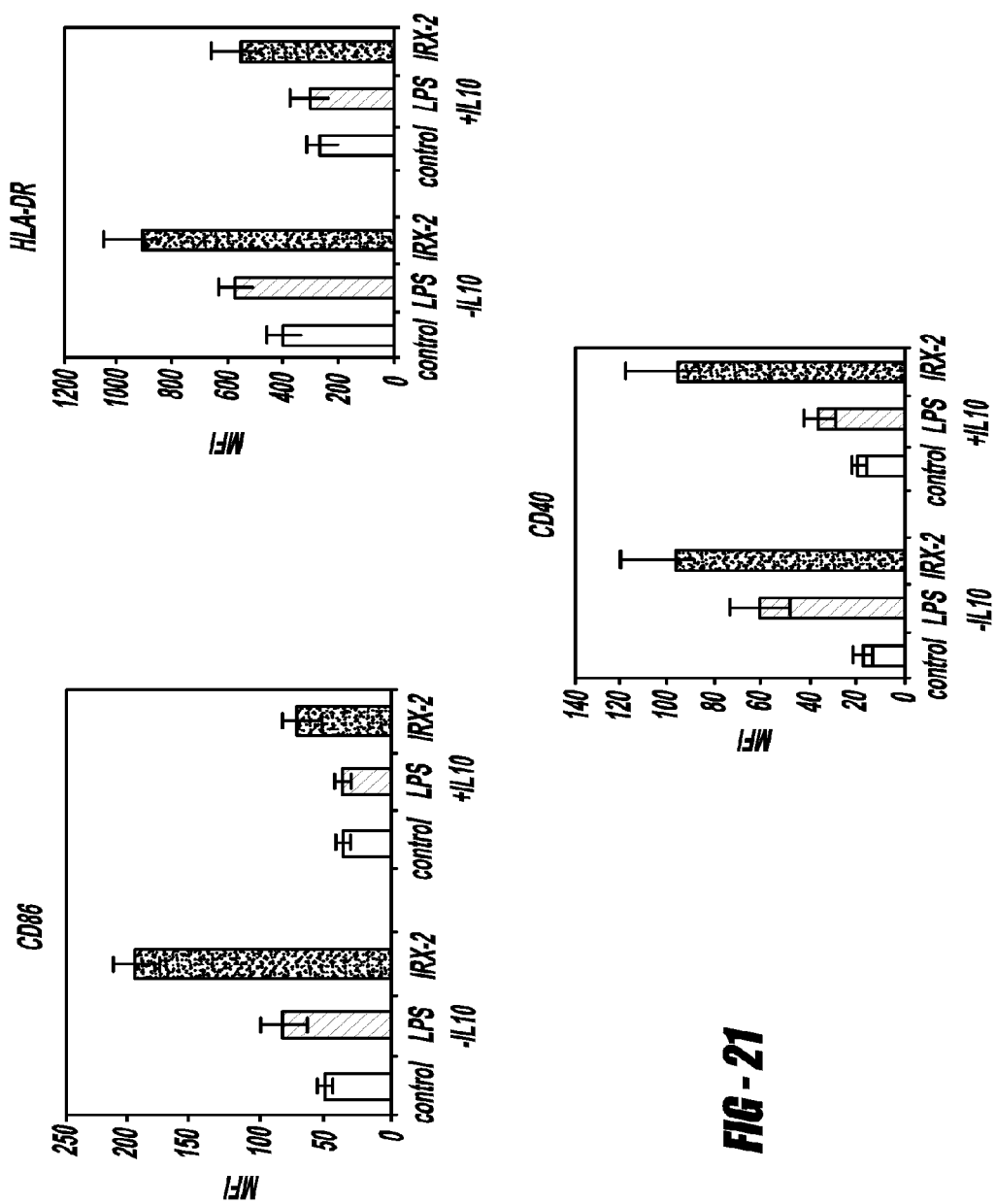
FIG. 21 contains bar graphs demonstrating that the NCM of the invention activates monocytes/macrophages, i.e., induces the activation markers, HLA-DR, CD86 and CD40, even in the presence of the immunosuppressing cytokine IL-10. The NCM is better at activating monocytes/macrophages than LPS, both in the presence and absence of IL-10.

Similarly, studies performed using LPS in modest doses (activating but not maximal) also indicated that NCM was a comparatively stronger activation signal. More specifically, adherent PBMCs were stimulated in the absence or presence of IL-10 (5 ng/ml) with either NCM (IRX-2) (at a 1:3 final concentration) or LPS (10 ng/ml) and assayed for the expression of activation markers by flow cytometry. As shown in FIG. 21, NCM caused a greater increase in the expression of the monocyte/macrophage maturation markers HLA-DR, CD86, and CD40 than LPS. Moreover, in the presence of the immunosuppressing cytokine, IL-10, the NCM was still able to stimulate the monocytes, whereas LPS failed to do so (p<0.02). The data shown in FIG. 21 represent the mean value+/−SEM from three independent experiments/donors.

Figure 22:
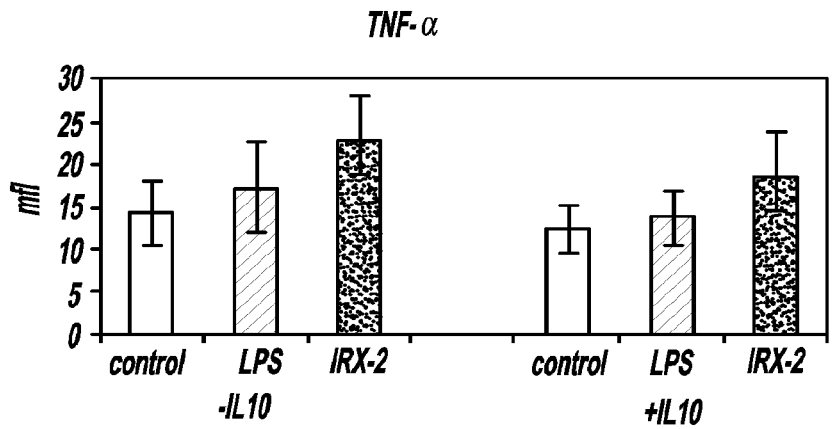
FIG. 22 is a bar graph demonstrating that the NCM of the invention stimulates the production of TNF-α from activated monocytes/macrophages and overcomes the immunosuppressive effects of IL-10. The NCM stimulated the production of TNF-α to a greater extent than LPS.

Finally, it is known that monocytes secrete TNF-α in response to activating signals, which secretion is associated with the non-specific killing activity of the monocytes/macrophages. The data shown in FIG. 22 demonstrate that the NCM of the invention stimulates the production of TNF-α from monocytes and overcomes the immunosuppressive effects of IL-10. More specifically, adherent PBMCs were stimulated in the absence or presence of IL-10 (5 ng/ml) with either NCM (IRX-2) (at a 1:3 final concentration) or LPS (10 ng/ml) and assayed for TNF-α production by intracellular staining and flow cytometry. As shown in FIG. 22, NCM caused a greater increase in the production of TNF-α than LPS or controls. In the presence of IL-10, the NCM was still able to stimulate the monocytes to produce TNF-α, whereas LPS was no longer able to do so (p<0.05). The data shown in FIG. 22 represent the mean value+/−SEM from five independent experiments/donors.

Example 11

The experiments detailed below demonstrate the ability of the NCM composition of the invention to act in combination with exogenous antigens to elicit an improved immune response (both cellular and antibody-based) against the antigen in mice.

Administration of Exogenous Tumor Antigens

Mice:

The procedure was to immunize mice with prostate-specific membrane antigen (PSMA) peptides based on predicted T cell epitopes of PSMA (LLH & ALF) (100 μg@) were conjugated to either ovalbumin (OVA) or Keyhole Limpet Hemocyanin (KLH). Previous attempts with isolated unconjugated peptides were not successful in mice. NCM (0.1 ml) was given as a single immunization with both conjugated antigens, preceded by low dose CY (400

μg/mouse) and followed by 9 daily injections of NCM (0.1 ml) without antigens, while CpG, alum, or RIBI-Corixa adjuvants were a single primary immunization with the OVA conjugate. Two booster immunizations (conjugate plus adjuvant as above) were given at day 21 and 28 to each group of 5 mice. The DTH reaction to the T cell peptides was measured 9 days after the final boost and serum was taken at sacrifice on days 15-21.

Figure 23:
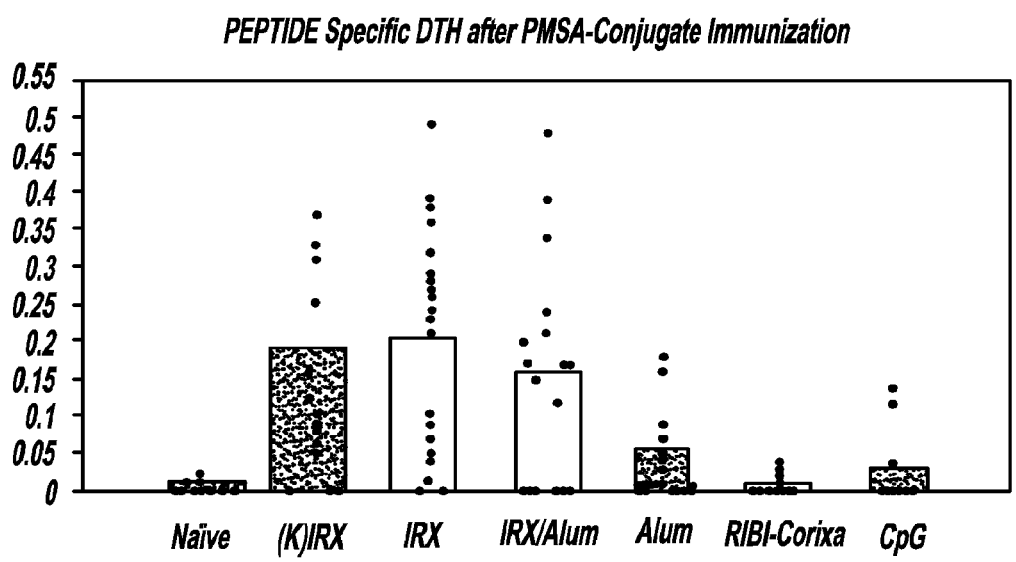
FIG. 23 is a chart illustrating the prostate-specific membrane antigen (PSMA) peptide-specific DTH response of mice immunized with various conjugates and adjuvants, including the NCM of the invention (IRX), wherein the response is indicated as swelling in mm for individual mice (dots) and for the average (bar), the adjuvant is listed on the x-axis, naive indicates mice not immunized, and all other mice are immunized with Ovalbumin-PSMA peptide conjugates except where indicated (KLH).

FIG. 23 shows the DTH results to skin testing of mice, using the individual ALF and LLH peptides (10 μg@), i.e., without conjugate, as the antigen challenge. As indicated by the Figure, NCM induces significant DTH responses to the antigens following immunization with both conjugates and also when given with alum for the OVA conjugate. Alum, RIBI-Corixa, and CpG showed negligible activity.

Serum Antibody Results:

Serum was diluted as indicated and added to the wells of a microplate coated with either peptide (ALF or LLH) or ovalbumin. Results are expressed as the average OD at 405 for 5 mice groups. Data are presented in Table IV below.

More specifically, mice immunized with the KLH conjugate in combination with NCM were negative for ovalbumin antibodies, but positive for the peptides. Mice immunized with the OVA conjugates and NCM were positive for antibodies for both OVA and the peptides, while those immunized with the OVA conjugate+CpG were positive for OVA only. These results indicate that NCM acts as an adjuvant in enhancing the ability of conjugated PSMA peptides to stimulate both DTH and IgG responses specific for the peptides, while other adjuvants like alum, RIBI-Corixa, and CpG were inactive or poorly active.

TABLE IV

| Dilution NCM | OVA-PSMA NCM | KLH-PSMA-NCM | OVA-PSMA-CpG |
|---|---|---|---|
| A: Serum IgG to ALF Peptide | | | |
| 1/200 | 0.929 | 0.692 | 0.241 |
| 1/400 | 0.989 | 0.518 | 0.208 |
| 1/800 | 0.695 | 0.351 | 0.144 |
| 1/1600 | 0.309 | 0.191 | 0.120 |
| B: Serum IgG to LLH Peptide | | | |
| 1/200 | 0.950 | 0.720 | 0.277 |
| 1/400 | 1.013 | 0.502 | 0.200 |
| 1/800 | 0.607 | 0.327 | 0.157 |
| 1/1600 | 0.316 | 0.201 | 0.125 |
| C: Serum IgG to Ovalbumin | | | |
| 1/500 | 0.920 | 0.269 | 1.050 |
| 1/1500 | 0.632 | 0.185 | 0.955 |
| 1/3000 | 0.457 | 0.146 | 0.813 |
| 1/0000 | 0.259 | 0.104 | 0.537 |

Additional experiments were performed to confirm the above results and to demonstrate that the NCM composition of the invention enhances T cell-specific immune responses in both young and old mice. In the experiments described below, the following methods and materials were used:

Reagents:

Prostate-Specific Membrane Antigen Peptides (Peptide 1: Leu-Leu-His-Glu-Thr-Asp-Ser-Ala-Val (SEQ ID NO: 1); Peptide 2: Ala-Leu-Phe-Asp-Ile-Glu-Ser-Lys-Val (SEQ ID NO: 2)) were synthesized by BioSynthesis Inc. (Lewisville, Tex.). Ovalbumin and cyclophosphamide were obtained from Sigma and KLH from Pierce Biochemicals. The RIBI adjuvant system (R700), also termed RAS, was purchased from Corixa and alum (40 mg/ml each of aluminum hydroxide and magnesium hydroxide) was purchased from Pierce Chemicals. RAS consisted of Monophosphoryl Lipid A (0.5 mg) and synthetic Trehalose Dicorynomycolate (0.5 mg), and 44 μl Squalene and Tween-80. CpG oligonucleotides (mouse specific sequence) were synthesized by BioSynthesis. The CpG sequence was TCCATGACGTTCCT-GACGTT (SEQ ID NO: 3) and was the phosphothionate derivative. The bioactivity of the CpG in the mouse was confirmed by measuring proliferation of mouse spleen cells and production of TNF-α by mouse adherent cells (data not shown).

NCM (also referred to herein as IRX-2) is a defined mixture of cytokines produced over a 24 hr period following stimulation of human peripheral blood mononuclear cells by PHA and ciprofloxacin. The PHA is removed prior to collecting the supernatant containing the cytokines. Two virus removal steps are included in the subsequent processing (ion exchange and dual nanofiltration). Stringent QC testing that includes both bioassay and ELISA determination of cytokine levels assures the consistency of the NCM (IRX-2). Safety testing with respect to sterility, DNA, micoplasm, endotoxin and virus testing for CMV and EBV are also part of the process. Several lots of IRX-2 were used over the course of these studies. The level of a number of cytokines contained in the NCM (IRX-2) lots are listed in Table V below. In the table, * represents the mean cytokine level for the 5 lots of IRX-2 used in these studies and ** represents levels not measured in all lots but for the most recent lot only. Additional cytokines present in μg/ml ranges include G-CSF, IL-12, and IL-10. Not present are typical Th2-biasing cytokines such as IL-3, IL-4, IL-5, IL-7 and IFN-α. When two lots were tested in the same experiment, they were always similar in activity (data not shown).

TABLE V

| Cytokine Levels in IRX-2 | |
|---|---|
| Cytokine (pg/ml) | Mean* (n = 5) |
| IL-2 | 4.72 |
| IL-1 | 0.45 |
| IFN-γ | 1.28 |
| TNF-α | 1.5 |
| IL-8** | 53.5 |
| IL-6** | 1.1 |
| GM-CSF** | 0.58 |

Conjugation of Antigen Peptides:

Peptides 1 and 2 described above were conjugated to a carrier molecule such as ovalbumin or KLH carriers as described above. Both peptides were conjugated to each carrier, i.e., as a single agent. For example, the OVA-PSMA conjugate or KLH-PSMA conjugate used in these studies contained both peptides linked to the carrier molecule. The peptides were conjugated to the respective carriers using the carbodiimide method (ODC; Pierce EDC kit 77502, Rockford, Ill.). In early studies, gluteraldehyde (Sigma, St. Louis, Mo.) was utilized but there was no difference in immunogenicity between the two methods (data not shown), so the carbodiimide coupling was chosen for subsequent studies as the more controlled method. Conjugation was characterized by measuring OD 280 and 215 in fractions from a Sephadex purification column. The 280 OD peak from the columns represents the ovalbumin or KLH conjugate and was collected as the conjugate. Dosing was based on the carrier concentration as recovered from the column. Monitoring the 215 showed a tailing peak representing the free peptides and provided confirmation that excess peptide was present during the conjugation procedure.

Immunization:

Balb/c mice were purchased from either Charles River or Harlan and were under the care of the Cold Spring Harbor Animal Facility (CSHL). All procedures were approved by the ALAC committee of the CSHL. In several experiments, cyclophosphamide (400 or 2000 µg/100 µl, IP) was injected three days prior to IRX-2 treatment. Subsequent studies demonstrated that cyclophosphamide did not have a statistically significant effect on the NCM (IRX-2) enhancement of the response in mice (data not shown) Immunizations were performed as follows: 200 µl/mouse containing 100 µg of PSMA conjugate with 100 µl adjuvant, e.g., NCM or alum, or PBS were injected subcutaneously at the base of the tail to provide for rapid draining to the regional lymph nodes. Nine additional injections of NCM (100 µl=6-8 IU of IL-2 equivalence) always followed the primary immunization (on days 2, 3, 4, 5, 8, 9, 10, 11, and 12). Unlike alum or RIBI, even repeated injections of NCM (IRX-2) into the same site did not result in significant inflammation at the site (unpublished observation). Two booster immunizations with conjugate plus adjuvant (at day 14 and 28) were performed prior to assessing DTH activity. Additional NCM was not given at the booster immunizations.

In the comparative adjuvant studies in young mice, the RAS (R-700=MPL+TDM in squalene/Tween 80) was reconstituted with 1 ml of PBS (as per the recommended protocol) and then mixed with 1 ml conjugate (1 mg/ml). Alum was mixed 1:1 with antigen. CpG oligonucleotides were mixed with the conjugate as per the published protocols for mice (100 µg conjugate with 20 µg CpG per mouse).

DTH Assay:

The in vivo antigen challenge for the DTH assay was with either a mixture of the two PSMA peptides (without carrier) (100 µg in 20 µl) or carrier alone (ovalbumin or KLH) (50-100 µg in 20 µl). Mice received subcutaneous injections of the challenge antigen in the left footpad and PBS in the right footpad at 9 days after booster immunization. After 24 hrs, the right and left footpad thicknesses were measured using a digital readout caliper (Preisser DIGI-MET Model 18314, Stofiting Co., Wooddale, Ill.). The swelling response was calculated by subtracting the right footpad thickness (baseline) from the left footpad thickness (experimental response). The data were expressed as individual mice swelling as well as mean+/−standard error of the mean. Statistical analysis was via Student's t-test or ANOVA.

Antigen/Mitogen-induced Cytokine Production and Measurement:

For these studies, the spleens were harvested 14-21 days after the booster immunization and isolated via dispersing through a wire screen. Adherent cells were obtained by taking spleen cells and allowing them to adhere to plastic for 90 minutes. The isolated adherent cells were pooled prior to addition to the cultures to provide for additional antigen-presenting cells. Approximately $6 \times 10^5$ lymphocytes per well were supplemented with $2 \times 10^4$ adherent cells.

Cytokine release from antigen or mitogen-induced activation of lymphocytes was measured in supernatants using Duo-Sets ELISA reagents from R and D Systems (Minn., Minn.). The optimal day for harvesting supernatants from antigen-stimulated cells was day 6 (for IFN-γ), while the PHA-stimulated IL-2 production was optimal at day 3 (data not shown).

Serum Antibodies to Ovalbumin and Peptides:

Serum at sacrifice was frozen for later use in ELISA assays. ELISA plates (Immunolon-4, Nunc, Denmark) were coated with the antigen of interest (ovalbumin, KLH, conjugate or individual peptides) overnight. Dilutions of serum were added to the blocked and washed wells and incubated overnight. Anti-mouse biotin and biotin-alkaline phosphatase (Southern BioTech, Birmingham, Ala.) were added sequentially and following addition of pNPP substrate, OD was measured and plotted vs. dilution of serum.

The results of these studies as detailed below demonstrate that the NCM of the invention stimulates tumor antigen-specific immune responses in both young and old mice in vivo. More specifically, in the experiments described below, the in vivo DTH (delayed type hypersensitivity) assay was utilized as an indicator of T cell activation. The DTH response to cancer antigens correlates well with elimination of tumor in animal models and clinical trials, and thus provides a useful in vivo correlate of T cell immune responses (see, e.g., Stuart, 1987; Sweat, 1998). As demonstrated by the present experiments, the NCM composition of the invention acts as an adjuvant with prostate-specific tumor antigens in stimulating T cell immune responses in young mice in vivo. Moreover, the present experiments demonstrate that NCM not only increases the immune response to T cell peptides in young mice but also restores T cell immune responses in T cell-impaired old mice. Thus, in the experiments detailed below, old mice were used as a model of immune dysfunction, an age-related decline in immune function that occurs in both mice and men. Furthermore, it is believed that this immune dysfunction is a major reason for the increased cancer incidence that occurs with increasing age in humans.

NCM Enhancement of Peptide-Specific DTH Response in Young Mice:

Young mice were immunized with either NCM (or PBS as a negative control) in combination with an OVA-PSMA or KLH-PSMA conjugate as described above (e.g., 200 µl/mouse, containing 100 µg of conjugate with 100 µl NCM or PBS) Immunizations were administered as subcutaneous injections at the base of the tail to provide for rapid draining to a regional lymph node. The mice were later challenged in a DTH assay as described above, using either the PSMA peptides (FIG. 24A) or the carrier used in the respective conjugate immunizations (FIG. 24B) as the challenge antigen.

Figure 24A:
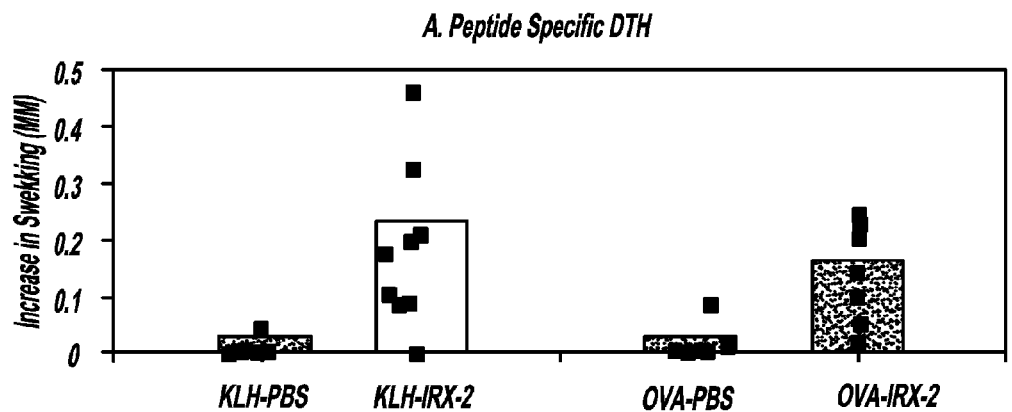
FIG. 24A depicts the enhanced peptide-specific DTH immune response in mice immunized with the NCM of the invention (IRX-2) in combination with either an OVA-PSMA or a KLH-PSMA conjugate and then challenged with the PSMA peptides (used for generating the conjugate) in a DTH assay. The increase in swelling for individual mice is represented by the data points, with the average increase in swelling being represented by the shaded boxes.
Figure 24B:
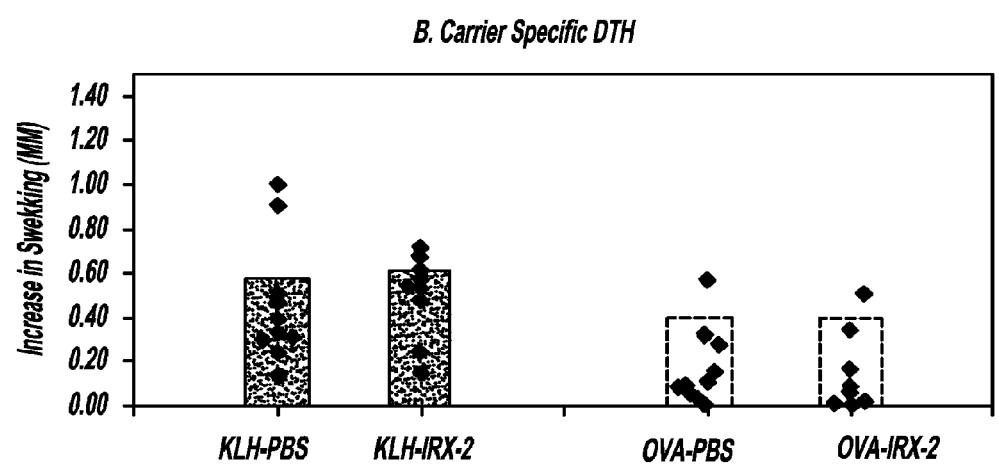
FIG. 24B depicts the DTH response to challenge with only the carrier used in the conjugate immunization.

As demonstrated in FIG. 24A, immunization of young mice (6-8 weeks old) with NCM (IRX-2) in combination with an OVA-PSMA or KLH-PSMA conjugate enhanced the peptide-specific DTH response, regardless of the carrier. When the peptides were co-administered with NCM but without conjugation, no peptide-specific DTH response was measured (data not shown). The DTH response to the carriers (either ovalbumin or KLH) was stronger than to the peptide, and administration with NCM did not enhance the DTH activity (FIG. 24B). Addition of alum to the NCM-peptide conjugate immunization did not modify the positive peptide-specific DTH response (data not shown).

The initial studies used NCM (IRX-2) in combination with a single pretreatment with cyclophosphamide three days before immunization. More specifically, mice were immunized with the OVA-PSMA conjugate and NCM (IRX-2) either with or without the administration of cyclophosphamide (either 400 µg/mouse or 2 mg/mouse) 3 days prior to the primary immunization. After two boosts (at day 14 and 28), a DTH assay was performed as described above.

Figure 25:
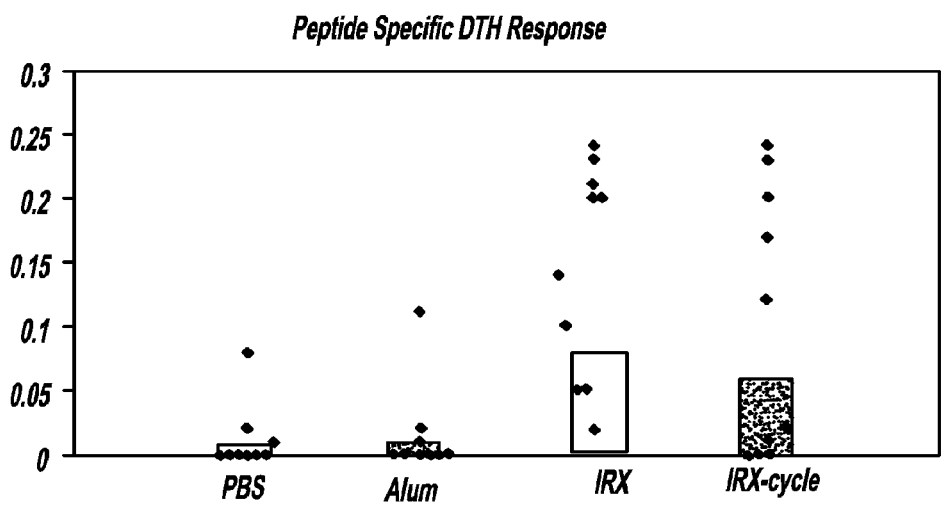
FIG. 25 depicts the influence of cyclophosphamide treatment on the peptide-specific DTH response in mice immunized with the OVA-PSMA conjugate and NCM. Cyclophosphamide treatment had no effect on the DTH response.

As shown in FIG. 25, the pretreatment with cyclophosphamide was not required for the peptide-specific response and it was not used in subsequent experiments. Moreover, this experiment confirmed that NCM treatment in combination with the peptide-conjugate enhanced the peptide-specific DTH response to a significantly greater extent (p<0.05)

than the use of alum or PBS, regardless of whether the mice were pre-treated with cyclophosphamide or not. The results of this assay were expressed as average swelling (bars in FIG. 25) and as the swelling for individual mice (diamond data points in FIG. 25). In addition, all of the results of these mouse studies utilized 9 days of additional NCM (IRX-2) injections after the primary immunization, although 4 additional treatments was not statistically different from 9 (data not shown).

Further, the ability of NCM to stimulate a peptide-specific immune response to the PSMA conjugates was compared to that of three other adjuvants: alum, the RIBI Adjuvant System (or RAS), and CpG. More specifically, mice were immunized with the OVA-peptide conjugate in combination with these different adjuvants. After two boosts (on day 14 and 28), a DTH assay was performed as described above (on day 9 post-boost). The results of this study are indicated in FIG. 26 and are expressed as the average swelling (bars) and as the swelling for individual mice (diamond data points).

Figure 26:
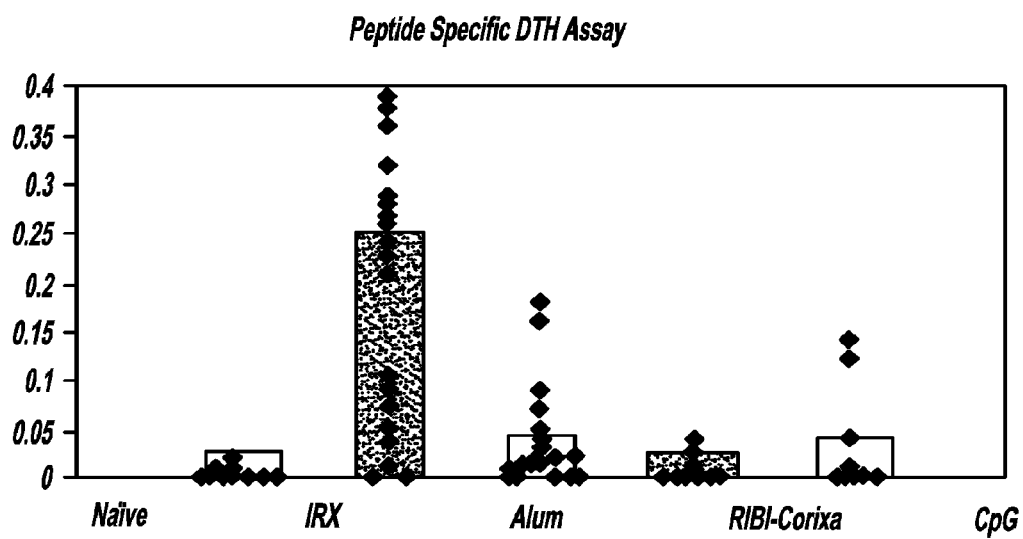
FIG. 26 depicts a comparison of the effects of various adjuvants, including the NCM of the invention (IRX), on the peptide-specific DTH response in mice immunized with a PSMA conjugate in combination with the respective adjuvants. The adjuvant effect of NCM was greater than the other adjuvants tested. Naive mice, i.e., non-immunized mice, represent a negative control.

As depicted in FIG. 26, the adjuvant effect of NCM (IRX-2) was greater than those of the other adjuvants tested ($p<0.001$). Although all of the adjuvants enhanced the response to the carrier protein compared to naive mice (data not shown), only NCM (IRX-2) enhanced the tumor peptide-specific immune response.

NCM Enhancement of Peptide-Specific Immune Response in Aging Mice

We first confirmed that the T cell immune response in old mice (>18 months old) was deficient as compared to the response in young mice (8-16 weeks old) by demonstrating that spleen cells from old mice stimulated with mitogen (PHA) were impaired with respect to secretion of two primary T cell cytokines, IL-2 and IFN-γ, as compared to the response from young mice (IL-2: 285 vs. 75 μg/ml and IFN-γ: 1535 vs. 128 μg/ml).

We then tested the DTH response in old versus young mice that had been immunized with PSMA conjugates and either NCM or alum as adjuvant, followed by antigen challenge using the DTH assay described above. More specifically, old mice (18-20 months at the start of the study) and young mice (6-8 weeks at the start of the study) were immunized with the PSMA conjugate, OVA-PSMA, in combination with NCM or alum as adjuvant, as described above. The mice were then challenged with antigen according to the DTH assay described above.

Figure 27A:
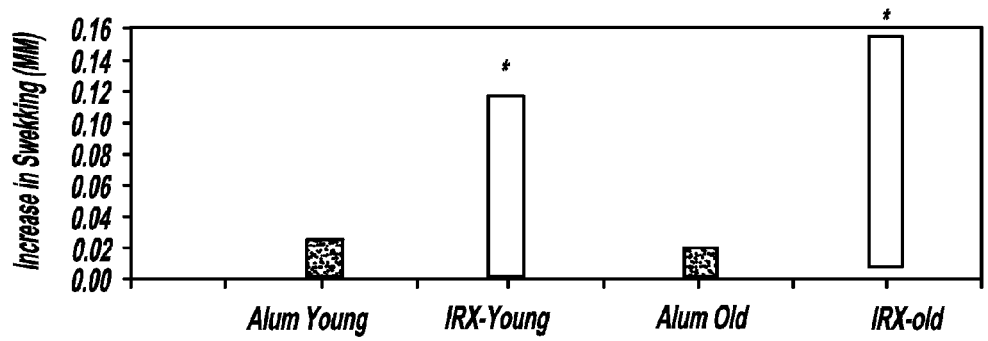
FIG. 27A depicts the peptide-specific DTH response of old versus young mice immunized with an OVA-PSMA conjugate in combination with either NCM (IRX) or alum as adjuvant. The NCM of the invention stimulated a greater peptide-specific DTH response in both old and young mice as compared to alum.

As indicated by FIG. 27A, NCM (IRX-2) restored the immune activity of old mice to that of young mice with respect to the peptide-specific DTH response. The results are expressed as difference in swelling between a PBS-injected paw and an antigen-injected paw for the mean of 9-15 mice per group. The average swelling for the NCM-treated old and young groups was not statistically different with respect to the peptide-specific response. However, the DTH responses of both the NCM-young and NCM-old groups were significantly greater than that seen from the alum-treated mice (* $p<0.005$, Student's t-test).

Figure 27B:
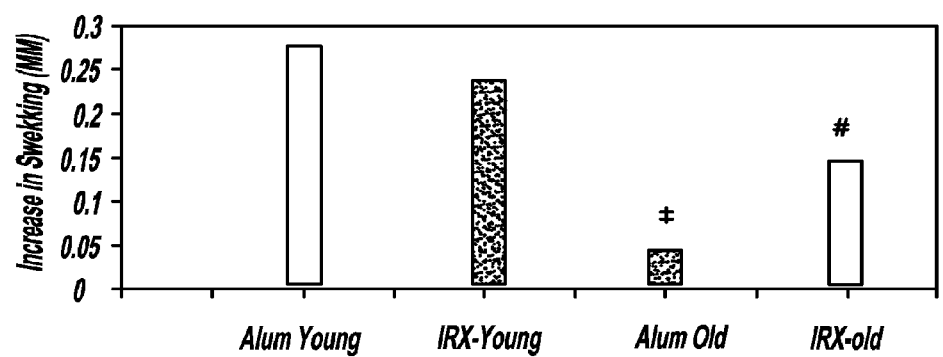
FIG. 27B depicts the carrier-specific DTH response of old versus young mice immunized with a PSMA conjugate in combination with either NCM (IRX) or alum as adjuvant. The NCM of the invention restored the carrier-specific DTI response in the old mice to that observed in the young mice.

With respect to the OVA carrier-specific DTH response, FIG. 27B demonstrates that the old mice were deficient compared to the young mice for this response (t $p<0.05$) but NCM treatment restored the ovalbumin-specific DTH response in the old mice (FIG. 27B). The response of young mice to ovalbumin was optimal in alum and was therefore not improved by NCM.

These experiments demonstrated the adjuvant effect of the NCM composition of the invention in stimulating specific anti-tumor antigen T cell immune responses in both old and young mice in vivo. In fact, the NCM of the invention provided a greater tumor antigen-specific T cell immune response compared to other adjuvants tested.

Further experiments, as described below, were carried out to measure the effect of NCM treatment on the production of the T cell cytokine, IFN-γ, which production is another indicator of immune stimulation.

Effect of NCM on the Spleen T Cell Ex Vivo Response

Figure 28:
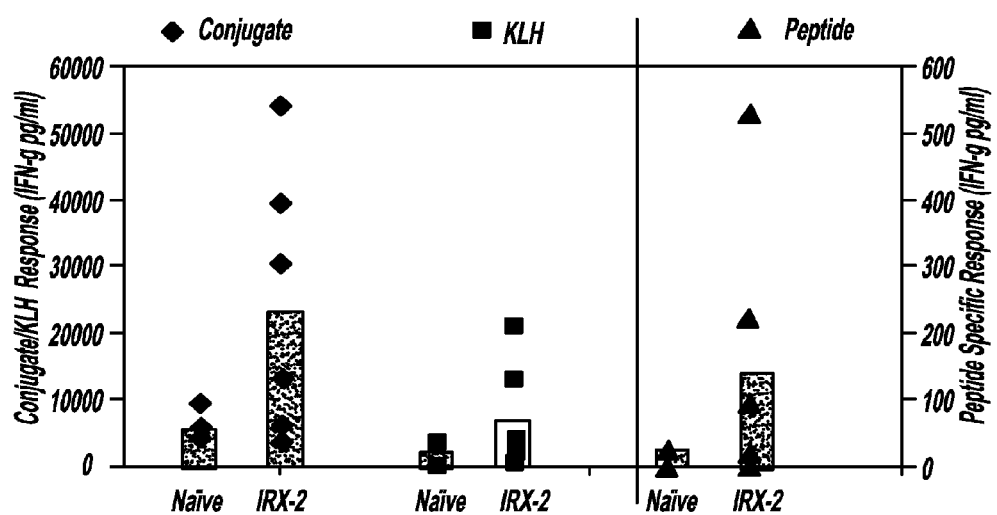
FIG. 28 depicts the enhanced T cell response in the form of IFNγ secreted by spleen cells from mice immunized with a KLH-PSMA conjugate and the NCM of the invention (IRX-2). The results are expressed for individual mice (data point markers) as well as the average response (shaded bars). All increases in IFN-γ secreted were statistically significant compared to naive controls.

Thus, the adjuvant effect of NCM treatment on mice immunized with NCM and a PSMA conjugate was determined by measuring the secretion of IFN-γ by spleen cells from the immunized mice. More specifically, spleen cells from mice immunized with the KLH-PSMA conjugate (as described above) and NCM (IRX-2) were harvested and incubated ex vivo with the conjugate (KLH-PSMA), the carrier (KLH) or the peptides (PSMA). The supernatants from the spleen cells were collected after 6 days of culture and measured for IFN-γ secretion as described in the methods and materials section above. As shown in FIG. 28, the T cell response, in the form of production of IFN-γ (in pg/mil), was greater for all three antigens in mice immunized with the conjugate and NCM as compared to naive mice.

Effect of Adjuvants on the Serum Antibody Titer

Figure 29A:
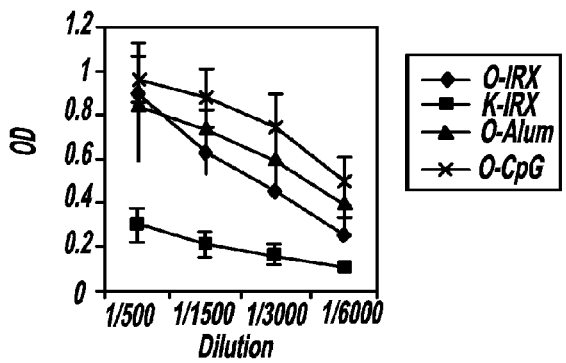
FIG. 29A-29C depicts serum antibody responses observed in mice immunized with the PSMA conjugates in combination with the NCM of the invention compared to other adjuvants, i.e., alum and CpG.
Figure 29B:
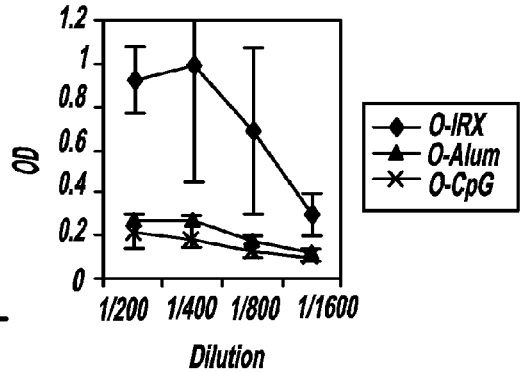
Figure 29C:
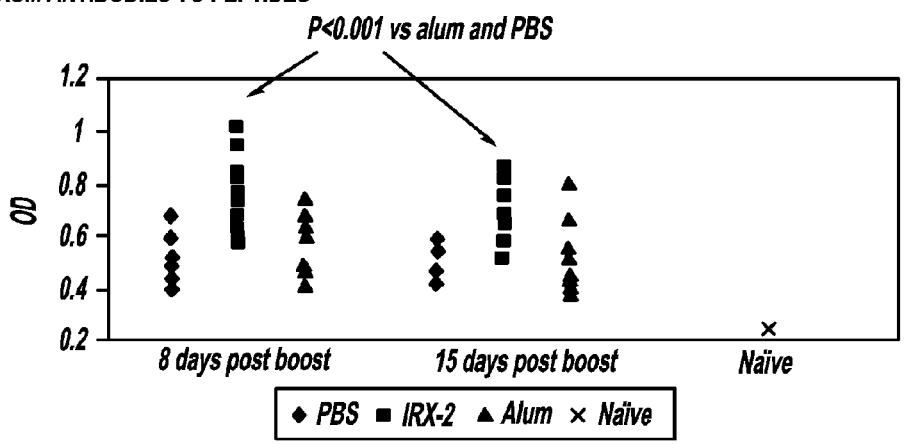

In addition, experiments were performed to determine whether NCM treatment had an adjuvant effect on antibody production in viva. More specifically, mice were immunized with the PSMA-conjugates as described above and the following adjuvants: NCM, alum or CpG. PBS was used as a negative control for adjuvant. Serum from the mice was obtained at sacrifice, either at 15 days after the third immunization (data depicted in FIGS. 29A and B) or at 8 and 15 days after the third boost (data of FIG. 29C)). Serum was assayed for antibodies by ELISA and the results expressed as dilution vs. optical density (FIGS. 29A and B) or as optical density at the optimal dilution, 1/400 (FIG. 29C).

Serum antibody titers to the carrier (whether ovalbumin or KLH) were measured and indicated that NCM (IRX-2), alum and CpG induced similar titers to ovalbumin, with the response being: CpG>alum>NCM (IRX-2) (FIG. 29A and data not shown). Mice immunized with the KLH conjugate, as predicted, did not generate titers to ovalbumin, confirming the specificity of the ELISA assay (see, e.g., FIG. 29A). However, as to the peptide-specific antibody response as depicted in FIG. 29B, NCM in combination with the OVA-PSMA peptide conjugate induced serum antibodies to both peptides, in contrast to alum and CpG. The data in FIG. 29B are for the ALF peptide with a $p<0.05$ by ANOVA for NCM vs. alum and CpG Similar responses were measured for the LLH peptide (data not shown). As depicted in FIG. 29C, when KLH was used in the conjugate as the carrier for the peptides, NCM (IRX-2) induced a higher peptide antibody response than no adjuvant (PBS) or alum ($p<0.001$ for NCM vs. alum and PBS). The markers in FIG. 29C indicate individual mice. The antibody response was measured on an ELISA plate coated with both peptides in the assay method as described above.

The studies described above indicate that the NCM of the invention enhances the T cell peptide-specific DTH response in vivo and the T cell response of spleen cells ex vivo in a prototype prostate peptide vaccine model. The critical nature of the mixture of cytokines (as opposed to the activity of just a few) is confirmed by the observation that preparations made from cell cultures lacking monocytes and therefore deficient in monocyte-derived cytokines failed to enhance the peptide-specific DTH response or the in vitro T cell response of spleen cells. The novel nature of the NCM was further demonstrated by comparing it to other adjuvants selected to represent various mechanisms of action. For example, CpG is a TLR agonist for APCs and is representative of TLR activating adjuvants, whereas the RAS system is representative of adjuvants with oil and bacterial components and is a safer alternative to Freund's adjuvant in mouse models. Alum is the adjuvant utilized in the majority of FDA-approved vaccines. In the present studies, NCM enhanced the peptide-specific DTH response but alum, CpG and RAS did not. Moreover, the NCM enhancement of the in vivo T cell peptide-specific DTH response correlated with an enhanced T cell response by spleen cells ex vivo as defined by antigen-specific secretion of IFN-γ. Finally, while all of the adjuvants enhanced the antibody response to the carrier (as compared to PBS), only NCM enhanced the antibody response to the peptides conjugated to the carrier.

The mechanism(s) through which the cytokines in NCM act to enhance the peptide-specific immune response as defined by the DTH assay is most likely complex since the recruitment, engulfment, proliferation, activation, maturation and migration of APCs and recruitment, proliferation, differentiation and maturation of T cells are all influenced by cytokines. However, the peptide-specific nature of the DTH response observed in these studies is believed to be a result of the influence of NCM on antigen presentation as well as subsequent T cell proliferation and migration to the periphery. It is also believed that the cytokines of the NCM shift the DC tolerance or T regulatory balance towards activation of the response to T cell epitopes. NCM may also be enhancing the T cell helper epitopes in the carrier providing additional stimulation of the development of an effective T cell immune response. As demonstrated herein (see Examples 9 and 10), the NCM of the invention stimulates the maturation and activation of dendritic cells, which promotes antigen presentation and the secretion of IL-12 (by the dendritic cells), IL-12 being a potent Th1 polarizing cytokine. The NCM is also a potent activator of monocytes and macrophages.

The NCM has further effects on T cells based on the known influence of the cytokines present in the NCM. As demonstrated in Examples 2 and 8 above, the NCM of the invention increases T lymphocyte counts in lymphocytopenic patients, including the production of naive T cells. In addition, it is known that IL-1 (present in the NCM) is a chemoattractant for lymphocytes as well as a stimulator of the production of other cytokines. Known activities include increase in the proliferation and activation of resting T cells by inducing IL-2 secretion and, more importantly for the activity of NCM, up regulation of IL-2 receptor. In addition, TNF-α (also present in NCM) enhances the activity of IL-1 as do other cytokines such as IL-8 and the CSFs. IL-8 also acts as a chemoattractant for multiple cells including T cells, basophils and neutrophils. IL-2 acts to enhance proliferation of activated cells by not just stimulating through the receptor but also by up-regulating additional IL-2 receptors as well as receptors for additional cytokines. Thus, the cytokines of the NCM compositions of the invention are pleotropic, influencing monocytes, dendritic cells and T cells.

The site of activity for the cytokines, present in physiological levels in the NCM of the invention, is local and includes both the injection site as well as the lymph nodes associated with the injection site. Since the NCM can be administered daily, elevated local levels of all the cytokines can be maintained. The peptide-specific nature of the DTH response using the NCM of the invention as an adjuvant argues for the use of the NCM in future T cell vaccines.

In addition, the present studies indicate that the NCM of the invention corrects a T cell cytokine deficit in aging mice. It is important to note that cancer more often occurs in older individuals who are known to have a declining immune system. Moreover, many of the current therapies for tumors (irradiation and chemotherapy) may themselves be immune suppressive, further reducing the immune competence of the patient. Thus, a cancer vaccine for many patients may benefit from an agent with the potential to restore the immune deficiency associated with aging, cancer treatments and cancer defense mechanisms. Given this potential obstacle to the use of a vaccine in the elderly, NCM was evaluated in the present studies for efficacy in aging as well as young immune competent mice. Spleen cells from old mice were first ascertained to be deficient in cytokine production of both IL-2 and IFN-γ when compared to young mice. The DTH response was also impaired with respect to ovalbumin Not only was NCM composition of the invention capable of restoring the weak response to the carrier, it was also effective in restoring the peptide-specific response to levels similar to that of young mice.

The protocol for the use of NCM in a vaccine model is based on phase I/II clinical studies using the NCM (IRX-2) in patients with head and neck cancer and the known kinetics of the immune response (see, e.g., Meneses 2003; Hillman, 1995). In clinical trials, targeting the tumor draining lymph node combined with a pre-injection of low dose cyclophosphamide and a 10 day NCM (IRX-2) administration results in enhancement of lymphocyte infiltration of the tumor, fragmentation of the tumor architecture and reduction in tumor size (see Examples 2-7 above). As described above, in the vaccine model in mice, initial studies used a pre-injection with cyclophosphamide but subsequent studies confirmed that this was not necessary in healthy non-tumor bearing mice (FIG. 25). Moreover, the daily administration of NCM after the primary immunization (for 4-9 days) appears to be important because it assures that the site of the injection and subsequently the draining lymph nodes have sufficient cytokine levels for optimal stimulation of the T cell immune response during the activation to memory transition period. Since the levels of the cytokines are low, there is no overt inflammatory response at the site of injection. This is in contrast to both alum and the RIBI Adjuvant System where swelling and inflammation were noted at the injection site (unpublished observation).

The proposed peptide-carrier vaccine described herein has significant clinical promise as a therapeutic vaccine based on data reported for Phase I/II studies using the PSMA peptides without conjugation to a carrier (Toja, 2000; O'Hagan, 2001; Katsuyuki, 2000; and Naylor, 1991). The two peptides are T cell epitopes based on both computer modeling and the response of lymphocytes from prostate cancer patients. When patients were treated with peptides alone or with peptide-pulsed dendritic cells, improved clinical and T cell responses were seen in the Phase I/II trials. In the phase I trials, however, the peptides without an adjuvant were less effective than the peptide-pulsed dendritic cells. Given the enhanced peptide-specific response observed when NCM was administered with the peptide-conjugate and the safety of KLH-conjugates in a wide variety of clinical trials, clinical trials with the peptides and NCM (IRX-2) are warranted.

The studies presented herein using a cancer peptide vaccine mouse model and the human clinical data showing a vigorous anti-tumor response to endogenous antigens using the NCM of the invention, support the use of the NCM composition of the invention in a tumor vaccine for the generation of an immune response sufficient to mediate tumor-specific destruction. In addition, since NCM acts to enhance T cell-specific responses in both young and old mice, NCM is a candidate for inclusion in any cancer vaccine, especially for elderly cancer patients, that has as its goal the enhancement of T cell immune responses.

Humans:

Three patients with advanced prostate cancer received unconjugated ALF & LLH peptides (100 μg @) with NCM (1 ml-100 units IL-2 equivalence) preceded by low dose CY (300 mg/m$^2$) and daily INDO (25 mg tid) plus 9 additional injections of NCM (1 ml). On day 15, a booster of NCM plus peptides was given. An additional patient (#4) received OVA-conjugated peptides in this regimen. Delayed hypersensitivity reactions (DTH) were measured with NCM (0.1 ml), ALF or LLH (10 μg) by intradermal skin test read at 24 hours in centimeters of erythema and in duration. The results are presented in Table VI.

TABLE VI

DTH to PSMA peptides & NCM

|  |  | Time 0 | 1 month |
|---|---|---|---|
| NCM | 1) | 0 | 0.5 |
|  | 2) | 1.0 | 1.0 |
|  | 3) | 0.5 | 1.0 |
|  | 4) | 0.3 | 0.3 |
| ALF Peptide | 1) | 0 | 0.5 |
|  | 2) | 0 | 0.1 |
|  | 3) | 1.0 | 1.0 |
|  | 4) | 0 | 0.4 |
| LHH peptide | 1) | 0 | 0.5 |
|  | 2) | 0 | 0.3 |
|  | 3) | 1.5 | 2.0 |
|  | 4) | 0 | 0.5 |

These data indicate that the NCM regimen is effective in inducing DTH reactions to unconjugated and conjugated PSMA peptides in humans with advanced prostate cancer. This result is different from results of most prior attempts that have failed with isolated peptides.

Further experiments demonstrated the ability of the NCM of the invention to act as an adjuvant with PSMA peptide antigens, resulting in the stabilization of disease. More specifically, three HLA-A2 positive males with advanced prostate cancer were treated with NCM (IRX-2) (115 units IL-2 equivalence) and the two PSMA peptides described above (100 μg each). The initial immunization was via injection in the neck, followed by nine injections of NCM (IRX-2) (plus low dose cyclophosphamide, indomethacin and zinc as in the protocol of Example 2 above), and then followed by five monthly boosters of NCM plus the two peptides.

Table VII summarizes briefly the clinical history (Hx) and responses to therapy (Rx). All three patients had received prostatectomy and orchiectomy 4 to 10 years before (in addition to other meds) and had relapsed. All were in a doubling phase of the rise in PSA ranging from 4 to an estimated 6 months. Two were symptomatic with bone pain. The immunization with NCM plus peptides and follow up booster injections induced no symptoms.

he two patients with bone pain had a clearing of pain. All three patients were stable clinically (except that patient #2 suffered a fracture of the femur with a transient exacerbation). All three developed transient dermal reactivity to skin tests with the isolated PSMA peptides (A and B; 10 μg each). All three showed increased reactivity to skin tests with NCM or PHA. These results indicate that the NCM of the invention immunized these patients to the PSMA peptides and stabilized disease during the period of immunization and boosting. See also FIG. 30, which depicts the stabilization of PSA antigen levels in these three patients over a six month period. The additional patient #4 described above showed transient PSA and clinical stabilization but clinical information is incomplete. A further additional patient with an early recurrence of PSA level (7) showed reversion to a normal level which has persisted for two years of follow-up without additional therapy (a complete response).

TABLE VII

|  | Prostate Rx | PSA Hx | IRX-4 Rx | Clinical Response |
|---|---|---|---|---|
| Patient 1 | Prostatectomy 1999 Orchiectomy 2002 Bone metastases | 2x increase in last 6 months (est.) Last PSA 24 | 2003 | PSA stable 5 months; 29 at end IRX-2 skin test 0.4 1.0 cm Peptide A 0→0.2 cm Peptide B 0→0.1 cm Stable clinically 6 months |
| Patient 2 | Prostatectomy 1998 Orchiectomy 1998 Anti-androgens 1999 | 4x increase in last 12 months Last PSA 160 | 2003 | PSA stable 7 months; 131 at end IRX-2 skin test 1.0 1.0 cm Peptide A 0→0.2 cm Peptide B 0→1.0 cm Stable clinically 6 months |
| Patient 3 | Prostatectomy 1993 Orchiectomy 1993 | 15x in last 20 months 2x in last 4 months Last PSA 35 | 2003 | PSA stable 7 months; 44 at end IRX-2 skin test 0.0 0.5 cm Peptide A 0→0.5 cm Peptide B 0→0.5 cm Stable clinically 6 months |

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

U.S. Pat. Nos.
U.S. Pat. No. 4,439,196
U.S. Pat. No. 4,447,233
U.S. Pat. No. 4,447,224
U.S. Pat. No. 4,475,196
U.S. Pat. No. 4,486,194
U.S. Pat. No. 4,487,603
U.S. Pat. No. 4,738,927
U.S. Pat. No. 4,925,678
U.S. Pat. No. 4,959,217
U.S. Pat. No. 4,992,367
U.S. Pat. No. 5,100,664
U.S. Pat. No. 5,167,616
U.S. Pat. No. 5,169,383
U.S. Pat. No. 5,503,841
U.S. Pat. No. 5,225,182
U.S. Pat. No. 5,632,983
U.S. Pat. No. 5,643,565
U.S. Pat. No. 5,698,194
U.S. Pat. No. 5,800,810
U.S. Pat. No. 6,060,068
U.S. Patent Application Publications
US 2004/0136952 A1
Publications Barrera J, Verastegui E, Meneses A, de la Garza J, Zinser J & Hadden J W. Neoadjuvant immunological treatment with IRX-2 in patients with advanced oral cavity squamous cell carcinoma of the head and neck induces clinical and histological responses. In First World Congress on Head and Neck Oncology. J J Alvarez Vicent, Ed. Monduzzi, Bologna, Italy; 1998; pp 1017-1019.

Barrera J, Verastegui E, Meneses A, Zinser J, de la Garza J, Hadden J W. Combination immunotherapy of squamous cell head and neck cancer: A phase 11 trial. Arch Otolaryngol Head Neck Surg 126:345-351 (2000).

Bellone, et al, Immunology Today, 20 (No. 10), p 457-462 (1998). Borysiewickz L K, Fiander A. Nimako M. A recombinant vaccine virus encoding human papilomavirus type 16 and 18, E6 and E7 proteins as immunotherapy for cervical cancer. Lancet 347:1524-1527 (1996).

Bender A, Sapp M, Schuler G, Steinamn R, and Bhardwaj N. Improved methods for the generation of dendritic cells from nonproliferating progenitors in human blood. Journal of Immunological Methods, 196:121-135 (1996).

Gabrilovich D, Chen H, Girgis K, Cunningham T, Meny G, Nadaf S, Kavanaugh D, and Carbone D P. Production of vascular endothelial growth factor by human tumors inhibits the functional maturation of dendritic cells. Nature Medicine, 2:1096-1103 (1996b).

Gabrilovich D, Corak J, Ciernik I F, Kavanaugh D, and Carbone D P. Decreased antigen presentation by dendritic cells in patients with breast cancer. Clinical Cancer Research, 3:483 (1997).

Gabrilovich D, Ishida T, Oyama T, Ran S, Kravtsov V, Nadaf S, and Carbone D P. Vascular endothelial growth factor inhibits the development of dendritic cells and dramatically affects the differentiation of multiple hematopoietic lineages in vivo. Blood, 92:41504156 (1998).

Gallo O, Franchi A, Magnelli L, Sardi I, Vannacci A, Boddi V, Chiarugi V, and Masini E. Cyclooxygenase-2 Pathway Correlates with VEGF Expression in Head and Neck Cancer. Implications for Tumor Angiogenesis and Metastasis. Neoplasia, 3:53-61 (2001).

Hadden J W, Endicot J, Baekey P, Skipper P, Hadden E M. Interleukins and contrasuppression induce immune regression of head and neck cancer. Arch Otolaryngol Head Neck Surg. 120:395-403 (1994).

Hadden J W, Saha A R, Sosa M, Hadden E M Immunotherapy with natural interleukins and/or Thymosin a 1 potently augments T lymphocyte responses of hydrocortisone-treated aged mice Int'l J Immunopharmacol 17:821-828 (1995).

Hadden J W, Verastegui E, Barrera J L, Kurman M, Meneses A, Zinser J W, de la Garza J, and Hadden E. A trial of IRX-2 in patients with squamous cell carcinomas of the head and neck. International Journal of Immunopharmacology, 3:1073-1081 (2003).

Hadden J W, Verastegui E, Barrera J, Meneses A, and de la Garza J. Lymph Node Histology in Head and Neck Cancer: Impact of IRX-2 Immunotherapy. Abstract #294 presented at 2004

Annual Meeting of the American Head and Neck Society, Combined Otolaryngology Spring Meetings (COSM), Washington D.C. (2004).

Hadden J W. The immunology of head and neck cancer: prospects for immunotherapy. Clinical Immunotherapy, 3:362-385 (1995a).

Hadden J W. Immunology and immunotherapy of breast cancer: An update: Int'l J Immunopharmacol 21:79-101 (1999).

Hadden J W. The immunopharmacology of head and neck cancer: An update. Intl J Immunopharmacol 11/12:629-644 (1997).

Hadden J W. The treatment of zinc deficiency is an immunotherapy. Int'l J Immunopharmacol 17:696-701 (1995).

Hadden J, Verastegui E, Barrera J L, Kurman M, Meneses A, Zinser J W, de la Garza J, and Hadden E, "A trial of IRX-2 in patients with squamous cell carcinomas of the head and neck," International Immunopharmacology 3; 1073-1081 (2003).

Hillman G G, Hass G P. Role of Cytokines in Lymphocyte Function. Aggarwal B B, Puri R K, eds. IN: Human Cytokines: Their Role in Disease and Therapy. Cambridge, Mass. Blackwell Sciences, Inc.; p 37-54 (1995).

Hold L, Zelle-Rieser C, Gander H. Papesh C, Ramoner R, Bartsch G, Rogatsch H, Barsoum A L, Coggin J H Jr., and Thurnher M Immunotherapy of Metastatic Renal Cell Carcinoma with Tumor Lysate-pulsed Autologous Dendritic Cells. Clinical Cancer Research, 8:3369-3376 (2002).

Kalinski P, Schuitemaker J, de Jong E, and Kapsenberg M. Prostagiandin E(2) is a selective inducer of interleukin-12 p40 (IL-12p40) production and an inhibitor of bioactive IL-12p70 heterodimer. Blood, 97:3466-3469 (2001).

Katsuyuki K, Nishisaka N, Jones R F, Wang C Y, Hass G P. Clinical trials of immunotherapy for advanced prostate cancer. Urologic Oncology 5: 265-273 (2000).

Kavanaugh D Y, Carbone D P. Immunologic dysfunction in cancer. Hematol-Oncol Clinics of North Amer 10(4):927-951 (1996).

Kaya M, Wada T, Akatsuka T, Kawaguchi S, Nagoya S, Shindoh M, Higashino F, Mezawa F, Okada F, and Ishii S. Vascular endothelial growth factor expression in untreated osteocarcoma is predictive of pulmonary metastasis and poor prognosis. Clinical Cancer Research, 6:572-578 (2000).

Langenkamp A, Messi M, Lanzavecchia A, and Sallusto F. Kinetics of dendritic cell activation: impact on priming of TH1, TH2 and nonpolarized T cells. Nature Immunology, 1:311-316 (2000).

Maclean G D, Miles D W, Rubens R D, Reddish M A, Longenecker bone marrow. Enhancing the effect of Theratope STn-KLH cancer vaccine in patients with metastatic breast cancer by pretreatment with low-dose intravenous cyclophosphamide J Immunother Emphasis Tumor Immunol 19(4):309-316 (1996).

Maass G, Schmidt W, Berger M, et al. Priming of tumor-specific T-cells in the draining lymph nodes after immunization with interleukin 2-secreting tumor cells: three consecutive stages may be required for successful tumor vaccination. Proc Natl Acad Sci USA, 92:5540-5542 (1995).

Mastrangelo M J, et al Seminars in Oncology 23(6): 773-781 (1996).

Mehvar, R. Modulation of the Pharmacokinetics and Pharmacodynamics of Proteins by Polyethylene Glycol Conjugation, J Pharm Pharmaceut Sci 3 (1): 125-136 (2000).

Meneses A, Verastegui E, Barrera J L, Zinser J, de la Garza J, Hadden J W. Histological findings in patients with head and neck squamous cell carcinoma receiving perilymphatic natural cytokine mixture prior to surgery. Arch Pathol Lab Med 122:447-454 (1998).

Meneses A, Verastegui E, Barrera J L, de la Garza J, and Hadden J W, Lymph node histology in head and neck cancer: impact of immunotherapy with IRX-2. International Immunopharmacology, 3; 1083-1091 (2003).

Mishell and Shiigi. Selected Methods in Cellular Immunology (1981).

Miyake M, Taki T, Hitomi S, and Hakomori S. Correlation of expression of H/Le(y)/Le(b) antigens with survival in patients with carcinoma of the lung. New England Journal of Medicine, 327:14-19 (1992).

Murphy G P, Tjoa B A, Simmons S J. Infusion of Dendritic Cells Pulsed With HLA-A2-Specific Prostate-Specific Membrane Antigen Peptides: A Phase II Prostate Cancer Vaccine Trial Involving Patients With Hormone-Refractory Metastatic Disease. The prostate. 38:43-78 (1999).

Naylor P H, et al. Preclinical and Clinical Studies on immunogenicity and Safety of the HIV-1 p17-Based Synthetic Peptide AIDS Vaccine—HGP-30-KLH. Int. J. Immunopharmac. 13 (Suppl. 1): 117-127 (1991).

Naylor P H, Hadden J W. T cell targeted immune enhancement yields effective T cell adjuvants. International Immunopharmacology 3: 1205-1215 (2003).

O'Hagan D T, MacKichan M L, Singh M. Recent developments in adjuvants for vaccines against infectious diseases. Biomolecular Engineering 18: 69-85 (2001).

Ridgway D. The First 1000 Dendritic Cell Vaccines. Cancer Investigation, 21:873-886 (2003).

Rogers P, and Croft M. CD28, Ox40, LFA-1 and CD4 modulation of Th1/Th2 differentiation is directly dependent on the dose of the antigen. The Journal of Immunology, 164:2955-2963 (2000).

Roitt I, Brostoff J, Male D. Immunology, JB Lippincott Co, Phila, Pa., (1989).

Romani N, Reider D, Heuer M, Ebner S, Kampgen E, Eibl B, Niederwieser D, and Schuler G. Generation of mature dendritic cells from blood. An improved method with regard to clinical applicability. Journal of Immunological Methods, 196:137-151 (1996).

Rosenberg S A, Yang J C, and Restifo N P. Cancer immunotherapy: moving beyond current vaccines. Natural Medicine, 10:909-915 (2004).

Sahin U, Tureci O, Pfreundschuh. Serological identification of human tumor antigens. Curr Opin Immunol 9:709-715 (1997).

Saito H, Tsujitani S, Ikeguchi M, Maeta M, and Kaibara N. Relationship between the expression of vascular endothelial growth factor and the density of dendritic cells in gastric adenocarcinoma tissue. British Journal of Cancer, 78:1573-1579 (1998).

Saito T, Kuss I, Dworacki G, Gooding W, Johnson J, and Whiteside T. Spontaneous ex Vivi Apoptosis of Peripheral Blood Mononuclear Cells in Patients with Head and Neck Cancer. Clinical Cancer Research, 5:1263-1273 (1999).

Sanda M G, Smith D C, Charles L G. Recombinant vaccinia-PSA (Prostvac) can include a prostate-specific immune response in androgen-modulated human prostate cancer. Urology 53: 260-266 (1999).

Schuler-Thurner B, Schultz E S, Berger T G, Weinlich G, Ebner S, Woerl P, Bender A, Feuerstein B, Fritsch P 0, Romani N, and Schuler G. Rapid Induction of Tumor-specific Type 1 T Helper Cells in Metastatic Melanoma Patients by Vaccination with Mature, Cryopreserved, Peptide-loaded Monocyte-derived Dendritic Cells. J. Exp. Med., 195:1279-1288 (2002).

Smith B, Smith G, Carter D, Sasaki C, and Haffty B. Prognostic Significance of Vascular Endothelial Growth Factor Protein Levels in Oral and Oropharyngeal Squamous Cell Carcinoma. Journal of Clinical Oncology, 18:2048-2052 (2000).

Sorg R, Ozcan Z, Brefort T, Fischer J, Ackermann R, Muller M, and Wernet P. Clinical-Scale Generation of Dendritic Cells in a Closed System. Journal of Immunotherapy, 26:374-384 (2003).

Steinman R M. The dendritic cell system and its role in immunogenicity. Annual Review of Immunology, 9:271-296 (1991).

Steinman R, and Nussenzweig M. Avoiding horro autotoxicus: The importance of dendritic cells in peripheral T cell tolerance. Proceedings of the National Academy of Science USA, 99:351-358 (2002).

Stuart P M, Iannaccone P M, Miller S D, Jenkins M K, del Muro F A, Melvold R W. In vitro and in vivo correlates of hybrid tumor resistance. J Natl Cancer Institute 78: 1159-1168 (1987).

Sweat S C, Pacelli A, Murphy G P, Bostwick D G. Prostate-specific membrane antigen (PSMA) expression is greatest in prostate adenocarcinoma and lymph node metastases. Urology 52: 637-640 (1998).

Takahashi A, Kono K, Ichihara F, Sugai H, Fujii H, and Matsumoto Y. Vascular Endothelial Growth Factor Inhibits Maturation of Dendritic Cells Induced by Lipopolysaccharide, but not by Proinflammatory Cytokines. Cancer Immunology and Immunotherapy, 53:543-550 (2004).

Thurnher M, Radmayr C, Ramoner R, Ebner S, Bock G, Klocker H, Romani N, and Bartsch G. Human renal-cell carcinoma tissue contains dendritic cells. International Journal of Cancer, 68:1-7 (1996).

Thurnher B, Haendle I, Roder C, Dieckmann D, Keikavoussi P, Jonuleit H, Bender A, Maczek C, Schreiner D, von den Driesch P, Brocker E B, Steinman R M, Enk A, Kampgen E, and Schuler G. Vaccination with Mage-3A1 Peptide-pulsed Mature, Monocyte-derived Dendritic Cells Expands Specific Cytotoxic T Cells and Induces Regression of Some Metastases in Advanced Stage 1V Melanoma. Journal of Experimental Medicine, 190:1669-1678 (1999).

Tjoa B A, Simmons S J, Bowe V A, Ragde H, Rogers M, Elgamal A, Kenny G M. Evaluation of phase I/II clinical trials in prostate cancer with dendritic cells and PSMA peptides. Prostate 36: 39-44 (1998).

Tjoa, B A, Murphy G P. Development of dendritic-cell based prostate cancer vaccine. Immuno. Letters 74: 87-93 (2000).

Van der Eynde B, Van der Bruggen, T cell defined tumor antigens. Curr Opin Immunol 9:684-693 (1997).

Wang R F, Rosenberg S A. Human tumor antigens for cancer vaccine development. Immunologic Reviews 170:85-100 (1999).

Weber J. Tumor vaccines. Medscape Anthology 3:2 (2000).

Whiteside, et al, Cancer Res. 53:5654-5662, (1993).

Whiteside T, Stanson J, Shurin M, and Ferrone S. Antigen-Processing Machinery in Human Dendritic Cells Up-Regulation by Maturation and Down-Regulation by Tumor Cells. The Journal of immunology, 173:1526-1534 (2004).

Whiteside T. Immunobiology and immunotherapy of head and neck cancer. Current Oncology Report, 2001:346-355 (2001).

What is claimed is:

1. A method for treating a patient having advanced prostate cancer, the method comprising:
   (a) administering to the patient having advanced prostate cancer an effective amount of a composition comprising a natural cytokine mixture (NCM), the NCM comprising IL-1, IL-2, IL-6, IL-8, IFN-gamma, and TNF-alpha; and
   (b) administering to the patient an effective amount of at least one exogenous tumor antigen,
   wherein the cytokines act as an adjuvant with the at least one exogenous tumor antigen and stimulate an immune response to the at least one exogenous tumor antigen in the patient;
   wherein the immune response is effective to alleviate or eliminate symptoms and effects of the advanced prostate cancer in the patient;
   wherein the patient has previously received surgery, radiotherapy, chemotherapy, or combinations thereof; and
   wherein after the surgery, radiotherapy, chemotherapy, or combinations thereof the patient has tumor recurrence, a rise in PSA antigen levels, or a combination thereof.

2. The method of claim 1, wherein the method comprises administering the composition and the at least one exogenous tumor antigen at the same time.

3. The method of claim 1, wherein the at least one exogenous tumor antigen is a protein or peptide.

4. The method of claim 1, wherein the at least one exogenous tumor antigen comprises one or more prostate-specific membrane antigen (PSMA) peptides.

5. The method of claim 1, wherein the effective amount is an amount sufficient to alleviate bone pain in the patient.

6. The method of claim 1, wherein the effective amount is an amount sufficient to stabilize PSA antigen levels in the patient.

7. The method of claim 1, wherein the patient has previously received surgery, and wherein the surgery comprises a prostatectomy and/or an orchiectomy.

8. The method of claim 1, wherein the patient is HLA-A2 positive.

9. The method of claim 1, wherein the patient has tumor recurrence.

10. The method of claim 1, wherein the method further comprises administering to the patient a non-steroidal anti-inflammatory drug (NSAID) and cyclophosphamide.

11. The method of claim 10, wherein the NSAID is indomethacin.

12. The method of claim 1, wherein the method further comprises administering to the patient a non-steroidal anti-inflammatory drug (NSAID), cyclophosphamide, and zinc.

13. The method of claim 12, wherein the NSAID is indomethacin.

14. The method of claim 1, wherein the composition is formulated as a sterile, injectable solution.

15. The method of claim 1, wherein the composition is administered to the patient via local perilymphatic injections.

16. The method of claim 1, wherein the method further comprises administering the composition and the exogenous tumor antigen more than once to the patient.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide 1

<400> SEQUENCE: 1

Leu Leu His Glu Thr Asp Ser Ala Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide 2

<400> SEQUENCE: 2

Ala Leu Phe Asp Ile Glu Ser Lys Val
1               5

<210> SEQ ID NO 3
<211> LENGTH: 20
<212> TYPE: DNA
<213> ORGANISM: Artificial Sequence
<220> FEATURE:
<223> OTHER INFORMATION: CpG sequence

<400> SEQUENCE: 3
tccatgacgt tcctgacgtt                                                 20
```